US011396540B1

(12) United States Patent
Puchacz

(10) Patent No.: US 11,396,540 B1
(45) Date of Patent: *Jul. 26, 2022

(54) METHODS FOR MAKING RECOMBINANT PROTEINS

(71) Applicant: Coherus Biosciences, Inc., Redwood City, CA (US)

(72) Inventor: Elzbieta Wiktoria Puchacz, Pleasanton, CA (US)

(73) Assignee: Coherus Biosciences, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/564,642

(22) Filed: Sep. 9, 2019

Related U.S. Application Data

(63) Continuation of application No. 14/845,440, filed on Sep. 4, 2015, now Pat. No. 10,435,464.

(60) Provisional application No. 62/046,496, filed on Sep. 5, 2014.

(51) Int. Cl.
| | |
|---|---|
| *C07K 16/24* | (2006.01) |
| *C12P 21/02* | (2006.01) |
| *C12N 5/02* | (2006.01) |
| *A61K 39/395* | (2006.01) |
| *C12N 5/00* | (2006.01) |
| *C12P 21/00* | (2006.01) |

(52) U.S. Cl.
CPC .......... *C07K 16/241* (2013.01); *A61K 39/395* (2013.01); *C12N 5/0018* (2013.01); *C12P 21/00* (2013.01); *C07K 2317/14* (2013.01); *C07K 2317/41* (2013.01); *C12N 2330/50* (2013.01); *C12N 2500/32* (2013.01); *C12N 2500/34* (2013.01); *C12N 2501/105* (2013.01)

(58) Field of Classification Search
None
See application file for complete search history.

(56) References Cited

U.S. PATENT DOCUMENTS

| | | | |
|---|---|---|---|
| 6,090,382 A | 7/2000 | Salfeld et al. | |
| 6,210,924 B1 | 4/2001 | Hu et al. | |
| 6,258,562 B1 | 7/2001 | Salfeld et al. | |
| 6,509,015 B1 | 1/2003 | Salfeld et al. | |
| 8,664,945 B2 | 3/2014 | Laville et al. | |
| 10,435,464 B1 | 10/2019 | Puchacz | |
| 2005/0272124 A1 | 12/2005 | Chen et al. | |
| 2012/0077213 A1 | 3/2012 | Pla et al. | |
| 2013/0089928 A1* | 4/2013 | An ....................... | C12N 5/0037 435/406 |

OTHER PUBLICATIONS

Mohamed et al, African Journal of Biotechnology; 2011; vol. 10, No. 81, pp. 18716-18721.*
Chiang et al., "Optimizing parameters for clinical-scale production of high IL-12 secreting dendritic cells pulsed with oxidized whole tumor cell lysate," *J. Transl. Med.* 9:198, 2011.
Craven et al., "Glucose concentration control of a fed-batch mammalian cell bioprocess using a nonlinear model predictive controller," *J. Process Control* 24:344-357, 2014.
Saraswat et al., "Preparative Purification of Recombinant Proteins: Current Status and Future Trends," *Biomed Res. Int.*, Article ID 312709, 2013, 18 pages.
Taniyama et al., "Therapeutic option of plasmid-DNA based gene transfer," *Curr. Top Med. Chem.* 12(15):1630-1637, 2012.
Miesegaes et al., "Analysis of Viral Clearance Unit Operations for Monoclonal Antibodies", Biotechnology and Bioengineering, vol. 106, No. 2, pp. 238-246, 2010.
Miesegaes et al., "Viral Clearance by Traditional Operations With Significant Knowledge Gaps (Session II): Cation Exchange Chromatography (CEX) and Detergent Inactivation", PDA Journal of Pharmaceutical Sciences and Technology, vol. 68, pp. 30-37, 2014.
Strauss et al., "Strategies for Developing Design Spaces for Viral Clearance by Anion Exchange Chromatography During Monoclonal Antibody Production", Biotechnology Progress., vol. 26, No. 3, pp. 750-755, 2010.

* cited by examiner

*Primary Examiner* — Bridget E Bunner
*Assistant Examiner* — Fozia M Hamud
(74) *Attorney, Agent, or Firm* — Fish & Richardson P.C.

(57) ABSTRACT

The present invention provides methods and compositions for making proteins, preferably antibodies, more preferably anti-tumor necrosis factor alpha antibodies, and most preferably adalimumab. The present invention further provides methods and compositions for mammalian cell culture, preferably Chinese Hamster Ovary cells.

20 Claims, 15 Drawing Sheets

METHODS FOR MAKING RECOMBINANT PROTEINS

RELATED APPLICATION

This application is a continuation of U.S. application Ser. No. 14/845,440, filed Sep. 4, 2015 (issued as U.S. Pat. No. 10,435,464), which claims priority to U.S. Provisional Application Ser. No. 62/046,496, filed Sep. 5, 2014, the entire contents of which are herein incorporated by reference in its entirety.

BACKGROUND OF THE INVENTION

Auto-immune diseases affect nearly 24 million people in the United States (roughly 8% of the population) alone making it one of the most prevalent diseases. By comparison, heart disease affects 22 million and cancer 9 million. Many auto-immune diseases are correlated with elevated levels of a naturally occurring protein in the body known as tumor necrosis factor ("TNFα"). TNFα is a cytokine capable of inducing fever, cell death and inflammation among other illnesses. TNFα works by binding to and activating cell surface receptors which lead to the activation of genes involved in inflammation.

Adalimumab is an anti-inflammatory drug targeted to inhibiting TNFα from binding to these cell surface receptors. Adalimumab is the first fully human monoclonal antibody approved by the United States Food and Drug Administration ("FDA") and is sold by AbbVie Biotechnology LTD under the trademark Humira® (Humira is a registered trademark of AbbVie Biotechnology LTD). Humira® has been approved by the FDA for several auto-immune diseases including rheumatoid arthritis, psoriatic arthritis, ankylosing spondylitis, Crohn's disease, ulcerative colitis, moderate to severe chronic psoriasis and juvenile idiopathic arthritis.

Methotrexate is also approved by the FDA for the treatment of various auto-immune diseases. Adalimumab has been shown to be more effective than methotrexate for the treatment of certain auto-immune diseases. The combination of adalimumab and methotrexate shows an even greater improvement in symptoms of auto-immune disease over the use of either one alone. One problem facing patients suffering from auto-immune diseases that could benefit from adalimumab or a combination therapy is the cost. Adalimumab can cost from $2,500 to $5,000 per month whereas methotrexate can cost as little as $30 per month. One reason that adalimumab has a higher cost is that it is a recombinant protein which must be produced by and harvested from cell culture. Improvements in the cell culture and protein production process can reduce the costs associated with the manufacture of adalimumab (HUMIRA®) and other antibodies including biosimilars, thereby allowing those cost savings to be passed on to patients.

Biosimilar molecules must also exhibit glycosylation patterns similar to the reference molecule. It has surprisingly been found that using a reduced amount of glucose in the cell culture media, together with alternate energy sources, will produce a biosimilar molecule having a glycosylation profile similar to the reference product.

Mammalian cells are routinely cultured in commercially available cell culture media including Dulbecco's Modified Eagle's Medium (DMEM) and Roswell Park Memorial Institute Medium (RPMI). However, for purposes of protein production, these media and the methods by which they are employed can be further modified to increase production. These modifications can be protein specific. Even small improvements in protein production or methods by which those proteins are produced can have a substantial economic impact on the cost of therapeutic recombinant proteins such as adalimumab. Thus, there remains a need in the art for improved methods and compositions of making proteins, in particular anti-TNFα antibodies, via cell culture.

SUMMARY OF THE INVENTION

In one embodiment, the present invention is directed to a method of producing an anti-TNFα antibody in a mammalian cell culture comprising:
(a) combining a culture medium that comprises 0.1 g/L to about 0.9 g/L added glucose with recombinant mammalian cells comprising nucleic acid encoding the anti-TNFα antibody under conditions sufficient to produce the anti-TNFα antibody, wherein the combining results in a recombinant anti-TNFα antibody production medium;
(b) culturing the mammalian cells in the recombinant protein production medium under conditions sufficient to produce the anti-TNFα antibody, wherein glucose is added to the production culture medium to maintain a glucose concentration of about 0.1 g/L to about 0.9 g/L, such that the anti-TNFα antibody is produced.

In another embodiment, the present invention is directed to a method of producing adalimumab in a mammalian cell culture comprising:
a growth phase comprising:
i) inoculating a perfusion bioreactor, containing a cell culture growth medium, with mammalian cells comprising a nucleic acid encoding adalimumab or a fragment thereof wherein the mammalian cells are at a concentration from about 0.1 million to about 5 million cells/milliliter; and
ii) allowing the mammalian cells to propagate resulting in an inoculum comprising from about 1 to about 50 million cells/milliliter, wherein the growth medium comprises glucose at a concentration from about 0.1 to about 20 grams/liter and at least one other hexose selected from the group consisting of galactose, mannose, fructose or a combination thereof at a concentration from about 0.1 to about 20 grams/liter; and
b) a production phase comprising:
i) inoculating a fed-batch bioreactor, containing a cell culture production medium, with the inoculum comprising from about 3 million to about 20 million cells/milliliter;
ii) maintaining the glucose in the production medium at a concentration from about 0.1 to about 0.9 grams/liter;
iii) optionally, maintaining the at least one other hexose in the production medium at a concentration from about 0.1 to about 20 grams/liter;
iv) optionally, supplementing the production medium with at least one additional feed absent glucose; and
v) harvesting the mammalian cell culture at a cell viability from about 20% to about 100%,
wherein the second growth medium comprises glucose at an initial concentration from about 0.1 to about 0.9 grams/liter and at least one other hexose selected from the group consisting of galactose, mannose, fructose or a combination thereof at an initial concentration from about 0.1 to about 20 grams/liter, such that adalimumab is produced.

Another embodiment of this invention is directed to a method of producing adalimumab in a mammalian cell culture comprising:
a) inoculating a fed-batch bioreactor containing a cell culture production medium with mammalian cells comprising a nucleic acid encoding adalimumab or a fragment thereof wherein the mammalian cells are at a concentration from about 0.1 million to about 2 million cells/milliliter;

b) maintaining the glucose in the production medium at a concentration from about 0.1 to about 0.9 grams/liter;

c) optionally, maintaining the at least one other hexose in the production medium at a concentration from about 0.1 to about 20 grams/liter;

d) optionally, supplementing the production medium with at least one additional feed absent glucose; and e) harvesting the mammalian cell culture at a cell viability from about 20% to about 100%;

wherein the production medium comprises glucose at an initial concentration from about 0.1 to about 0.9 grams/liter and at least one other hexose selected from the group consisting of galactose, mannose, fructose or a combination thereof at an initial concentration from about 0.1 to about 20 grams/liter, such that adalimumab is produced.

Another embodiment of this invention is a method of producing adalimumab in a mammalian cell culture comprising:

a) a first cycle comprising:
  i) inoculating a fed-batch bioreactor, containing a first cell culture production medium, with mammalian cells comprising a nucleic acid encoding adalimumab or a fragment thereof wherein the mammalian cells are at a concentration from about 0.1 million to about 2 million cells/milliliter;
  ii) maintaining the glucose in the first production medium at a concentration from about 0.1 to about 0.9 grams/liter;
  iii) optionally, maintaining the at least one other hexose in the first production medium at a concentration from about 0.1 to about 20 grams/liter;
  iv) optionally, supplementing the first production medium with at least one additional feed absent glucose; and
  v) harvesting 90% of the mammalian cell culture comprising a cell viability from about 80% to about 100%;

wherein the first production medium comprises glucose at an initial concentration from about 0.1 to about 0.9 grams/liter and at least one other hexose selected from the group consisting of galactose, mannose, fructose or a combination thereof at an initial concentration from about 0.1 to about 20 grams/liter; and b) a second cycle comprising:
  i) removing the first production medium from the remaining 10% of the mammalian cell culture;
  ii) adding a second production medium comprising glucose at an initial concentration from about 0.1 to about 0.9 grams/liter and at least one other hexose selected from the group consisting of galactose, mannose, fructose or a combination thereof at an initial concentration from about 0.1 to about 20 grams/liter;
  iii) maintaining the glucose in the second production medium at a concentration from about 0.1 to about 0.9 grams/liter;
  iv) optionally, maintaining the at least one other hexose in the second production medium at a concentration from about 0.1 to about 20 grams/liter;
  v) optionally, supplementing the second production medium with at least one additional feed absent glucose; and
  vi) harvesting 90% of the mammalian cell culture at a cell viability from about 80% to about 100%; and
c) optionally, repeating the first and second cycle;
such that adalimumab is produced.

Another embodiment of this invention is a method of producing adalimumab in a mammalian cell culture comprising:

a) a growth phase comprising:
  i) inoculating a perfusion bioreactor containing a cell culture growth medium with mammalian cells comprising a nucleic acid encoding adalimumab or a fragment thereof wherein the mammalian cells are at a concentration from about 0.1 million to about 5 million cells/milliliter; and
  ii) allowing the mammalian cells to propagate resulting in the mammalian cell culture comprising from about 10 to about 40 million cells/milliliter, wherein the growth medium comprises glucose at a concentration from about 0.1 to about 10 grams/liter and at least one other hexose selected from the group consisting of galactose, mannose, fructose or a combination thereof at a concentration from about 0.1 to about 20 grams/liter; and b) a production phase comprising:
  i) removing the growth medium;
  ii) adding a production medium comprising glucose at a concentration from about 0.1 to about 0.9 grams/liter and at least one other hexose selected from the group consisting of galactose, mannose, fructose or a combination thereof at a concentration from about 0.1 to about 20 grams/liter;
  iii) maintaining the glucose in the first production medium at a concentration from about 0.1 to about 0.9 grams/liter;
  iv) optionally, maintaining the at least one other hexose in the production medium at a concentration from about 0.1 to about 20 grams/liter;
  v) optionally, supplementing the production medium with at least one additional feed absent glucose; and
  vi) harvesting the mammalian cell culture at a cell viability from about 20% to about 100%,
such that adalimumab is produced.

In another aspect, the antibody an anti-TNFα antibody, more specifically the antibody is adalimumab.

In another aspect, the mammalian cells are Chinese Hamster Ovary ("CHO") cells.

In another aspect, this invention includes perfusion culturing or a fed-batch culturing.

Another aspect of this invention comprises a viral deactivation step comprising adding Triton X-100 detergent.

In another aspect, the anti-TNFα antibody is secreted into the culture medium.

In another aspect, the invention further comprises purifying the anti-TNFα from the production culture medium.

In another aspect, the purified anti-TNFα antibody is formulated into a pharmaceutical composition.

Another aspect is a pharmaceutical composition comprising an antibody produced by any of the methods of this invention.

Another aspect of this invention is a kit comprising the pharmaceutical composition of comprising an antibody produced by any of the methods of this invention.

In another aspect of this invention, the cell viability is from about 50% to about 80%.

DETAILED DESCRIPTION OF THE INVENTION

A. Definitions

Figure 1:
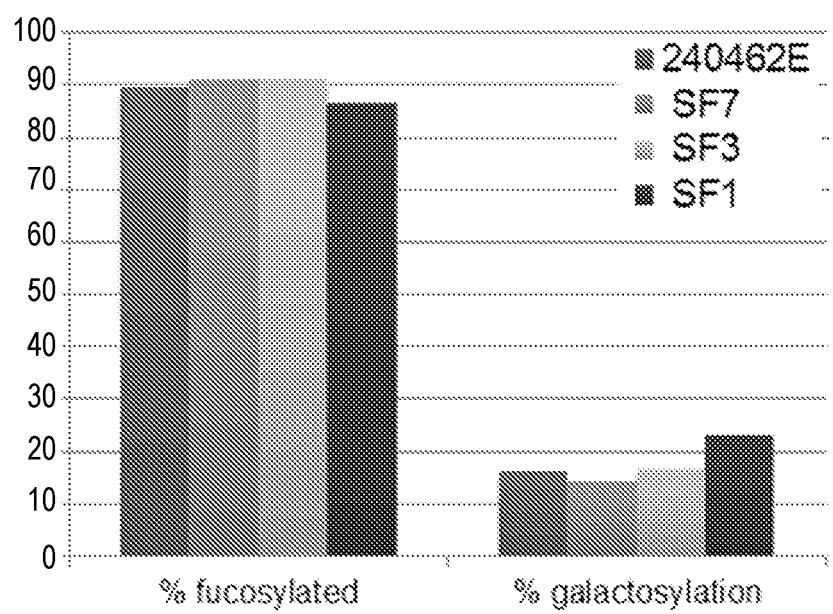
FIGS. 1 and 2 are graphs showing levels of certain glycans present on adalimumab produced using the low-glucose production method of Example 3, Experiment #1 and reference adalimumab in Humira® Lot #240462E.

Unless otherwise defined, all technical and scientific terms used herein have the same meaning as commonly understood by one of ordinary skill in the art to which this invention pertains. In the case of conflict, the present document, including definitions will control.

As used herein the term "optionally" refers to distinct methods or compositions one of which contains the subsequent step(s) or composition(s) and one of which does not.

As used herein the term "allowing" refers to any method of causing a result to occur including but not limited to taking no action.

As used herein the term "maintaining" refers to any method of causing a parameter to remain the same or similar including but not limited to adding or removing. Maintaining can include, e.g., monitoring a parameter in a cell culture, e.g., glucose concentration, and injecting a solution including glucose into the cell culture in order to increase or maintain the glucose concentration in the cell culture. In some examples, maintaining can include monitoring a parameter, e.g., glucose concentration, in a cell culture, and diluting the cell culture with glucose-free medium (e.g., any of the types of media described herein) in order to decrease or maintain the glucose concentration in the cell culture.

As used herein the term "combining" means adding a culture medium (e.g., a feed culture medium) to a cell culture and/or allowing the cells in the cell culture to catabolize the sugar present in a culture medium.

As used herein the term "harvesting" refers to any method of separating desired cells or their desired product from undesired components of a culture or medium (e.g., any of the different types of media described herein).

As used herein, the term "inoculation" or "inoculating" refers to the addition of cells to a medium (e.g., any of the types of culture medium described herein) to begin the culture.

As used herein, the term "cell viability" refers to the percentage of cells that are alive. Cell viability can be measured by trypan blue staining with a VI-CELL® (Vi-Cell is a registered trademark of Beckman Coulter, Inc.) cell viability analyzer.

As used herein the term "cell culture" refers to cells of a mammal that are maintained in vitro. As is known in the art, the term cell culture includes a culture medium (e.g., any of the types of culture media described herein).

As used herein, the term "cell culture growth phase" or "growth phase" refers to the period during which cultured cell concentration is increasing (e.g., exponentially increasing) in number. During growth phase, cells may be cultured in an environment intended to cause the highest possible rate of cell proliferation.

As used herein, the term "cell culture production phase" or "production phase" refers to a period during which cultured cells are producing maximal amounts of recombinant polypeptide or protein. During production phase, cells may be cultured in a medium intended to cause the highest possible rate of polypeptide or protein production.

As used herein the term "recombinant polypeptide" or "recombinant protein" refers to a polypeptide or protein resulting from the process of genetic engineering.

As used herein the term "genetic engineering" refers to altering a cell's DNA such that the cell expresses a particular polypeptide or protein. A cell's DNA can be altered by incorporation of a DNA sequence capable of causing the expression of a particular polypeptide or protein using methods of "genetic engineering," such as viral infection with a recombinant virus, transfection, transformation, electroporation, hydrodynamic, jet injection or gene gun methods. (See e.g., Taniyama Y, et al., Therapeutic option of plasmid-DNA based gene transfer, *Curr Top Med Chem*, 2012, 12(15), 1630-7). Methods for genetically engineering cells to express a protein of interest are well known to those skilled in the art. The polypeptide or protein may be normally produced by the host cell. In this case, an alternative promoter is incorporated near the endogenous DNA sequence such that expression of the gene is increased over normal levels. The polypeptide or protein may not be normally produced by the host cell. For example, the host cell can be a CHO cell or the mouse myeloma cell, NS0, cell that has been genetically engineered to produce a human polypeptide or protein.

The term "perfusion culturing" means culturing, in a container or vessel, a plurality of mammalian cells (e.g., recombinant mammalian cells capable of producing a desired protein) that have been contacted with a culture medium (as defined herein) to obtain a recombinant protein production medium (as defined herein), wherein the culturing includes periodic or continuous removal of a volume of the recombinant protein production medium from the container or vessel and at the same time or shortly after adding substantially the same volume of a culture medium to the container or vessel (e.g., a perfusion bioreactor). In some examples, there is an incremental change (e.g., increase or decrease) in the volume of the recombinant protein production medium removed and culture medium added over incremental periods (e.g., an about 24-hour period) during the culturing period (e.g., the culture medium refeed rate on a daily basis). The fraction of media removed and replaced each day can vary depending on the particular cells being cultured, the initial seeding density, and the cell density at a particular time.

The term "fed-batch culturing" is a term of art and means culturing a plurality of mammalian cells (e.g., recombinant mammalian cells capable of producing a desired protein) that have been contacted with a culture medium (as defined herein) to obtain a recombinant protein production medium (as defined herein), wherein the culturing of the cells present in a container (e.g., a fed-batch bioreactor) includes the periodic or continuous addition of a predetermined volume of culture medium to the container without substantial or significant removal from the container of the recombinant protein production medium. The culture medium added after initial preparation of a recombinant protein production medium (such as, e.g., later-added medium being understood in the art, and referred to herein, as a feed culture medium) can be the same as, or different from, the initial culture medium first contacted with recombinant cells to initially obtain the recombinant protein production medium. In some examples of fed-batch culture, the later added feed culture medium can be a concentrated form of the initial culture medium. In some examples of fed-batch culture, the later added culture medium is added as a dry powder. Skilled practitioners will appreciate that a bioreactor can be adapted to be used in fed-batch culturing (e.g., adapted to be a fed-batch bioreactor).

As used herein, the term "feed" refers to the addition of any component(s) made to a culture after inoculation.

As used herein the term "perfusion bioreactor" refers to a cell culture system in which the cell culture medium (e.g., a first cell culture medium, a second cell culture medium, a culture medium, a recombinant protein production medium, a cell culture growth medium, or a production medium) is continuously replaced with fresh media.

As used herein the term "fed-batch bioreactor" refers to a cell culture system in which the cell culture medium (e.g., a first cell culture medium, a second cell culture medium, a culture medium, a recombinant protein production medium, a cell culture growth medium, or a production medium) is supplied with additional nutrients.

As used herein, the term "mammalian cells" refers to any cell line derived from a mammal that is useful for in vitro protein production including CHO cells.

As used herein, the term "cell culture medium" or "culture medium" refer to a solution containing components necessary for the maintenance, growth, or proliferation of cells in vitro. Cell culture medium may be optimized for a specific cell culture use, including, for example, cell culture growth medium which is formulated to promote cell growth during the growth phase, or cell culture production medium which is formulated to promote recombinant polypeptide or protein production during the production phase.

As used herein, the term "cell culture growth medium" or "growth medium" refers to cell culture medium designed to supply cells with the necessary or beneficial nutrients during the growth phase of a cell culture. During growth phase, cells may be cultured in a medium intended to cause the highest possible rate of cell proliferation.

As used herein the term "cell culture production medium" or "production medium" refers to cell culture medium designed to supply cells with the necessary or beneficial nutrients during the production phase of a cell culture. During production phase, cells may be cultured in a medium intended to cause the highest possible rate of polypeptide or protein production.

The term "animal-derived component free liquid culture medium" means a liquid culture medium (e.g., a first cell culture medium, a second cell culture medium, a culture medium, a recombinant protein production medium, a cell culture growth medium, or a production medium) that does not contain any components (e.g., proteins or serum) derived from a mammal.

The term "serum-free liquid culture medium" means a liquid culture medium (e.g., a first cell culture medium, a second cell culture medium, a culture medium, a recombinant protein production medium, a cell culture growth medium, or a production medium) that does not contain a mammalian serum.

The term "serum-containing liquid culture medium" means a liquid culture medium (e.g., a first cell culture medium, a second cell culture medium, a culture medium, a recombinant protein production medium, a cell culture growth medium, or a production medium) that contains a mammalian serum.

The term "chemically-defined liquid culture medium" is a term of art and means a liquid culture medium (e.g., a first cell culture medium, a second cell culture medium, a culture medium, a recombinant protein production medium, a cell culture growth medium, or a production medium) in which all of the chemical components are known. For example, a chemically-defined liquid culture medium does not contain fetal bovine serum, bovine serum albumin, or human serum albumin, as these preparations typically contain a complex mix of albumins and lipids.

The term "protein-free liquid culture medium" means a liquid culture medium that does not contain any protein (e.g., any detectable protein).

The term "recombinant protein production medium" means a medium suitable for producing a recombinant protein obtained by contacting a culture medium (as defined herein) with cells (e.g., mammalian cells) comprising nucleic acid encoding the recombinant protein. For purposes herein, it should be understood that a "culture medium" (as defined herein, above) differs from a "recombinant protein production medium" in that the latter, for example, can contain products of cellular metabolism, as well as the recombinant protein being produced by the cells. Moreover, cellular metabolism occurring in the recombinant protein production medium consumes energy sources in the culture medium, and produces metabolites. Without intending to be bound to any particular theory, it may be possible that the recombinant protein production medium may contain detectable levels of glucose which are not due to exogenously added glucose.

The term "agitating" means stirring or otherwise moving a portion of culture medium (e.g., a first cell culture medium, a second cell culture medium, a culture medium, a recombinant protein production medium, a cell culture growth medium, or a production medium) in a bioreactor. Agitating is performed in order to, e.g., increase the dissolved O2 concentration in the culture medium in a bioreactor. Agitation can be performed using any art known method, e.g., an instrument or propeller. Exemplary devices and methods that can be used to perform agitation of a portion of the culture medium in a bioreactor are known in the art.

The term "capturing" means a step performed to partially purify or isolate and concentrate a recombinant protein from one or more other components present in a culture medium or a diluted culture medium (e.g., culture medium proteins or one or more other components (e.g., DNA, RNA, or other proteins) present in or secreted from a mammalian cell). Typically, capturing is performed using a resin that binds a recombinant protein (e.g., through the use of affinity chromatography). Non-limiting methods for capturing a recombinant protein from a culture medium or diluted culture medium are described herein and others are known in the art. A recombinant protein can be captured from a culture medium using at least one chromatography column (e.g., any of the chromatography columns described herein).

The term "purifying" means a step performed to isolate a recombinant protein from one or more other impurities (e.g., bulk impurities) or components present in a fluid containing a recombinant protein (e.g., culture medium proteins or one or more other components (e.g., DNA, RNA, other proteins, endotoxins, viruses, etc.) present in or secreted from a mammalian cell). Purification can be performed using a resin that binds either a recombinant protein or contaminants (e.g., through the use of affinity chromatography, hydrophobic interaction chromatography, anion or cation exchange chromatography, or molecular sieve chromatography). A recombinant protein can be purified from a fluid containing the recombinant protein using at least one chromatography column (e.g., any of the chromatography columns described herein).

The term "polishing" is a term of art and means a step performed to remove remaining trace or small amounts of contaminants or impurities from a fluid containing a recombinant protein that is close to a final desired purity. For example, polishing can be performed by passing a fluid containing the recombinant protein through a chromatographic column(s) or membrane absorber(s) that selectively binds to either the recombinant protein or small amounts of contaminants or impurities present in a fluid containing a recombinant protein. In such an example, the eluate/filtrate of the chromatographic column(s) or membrane absorber(s) contains the recombinant protein.

The term "filtering" means the removal of at least part of undesired biological contaminants (e.g., a mammalian cell, bacteria, yeast cells, viruses, or mycobacteria) and/or particulate matter (e.g., precipitated proteins) from a liquid (e.g., a culture medium or fluid).

The term "secreted protein" or "secreted recombinant protein" means a protein (e.g., a recombinant protein) that originally contained at least one secretion signal sequence when it is translated within a mammalian cell, and through, at least in part, enzymatic cleavage of the secretion signal sequence in the mammalian cell, is secreted at least partially into the extracellular space (e.g., a culture medium). Skilled practitioners will appreciate that a "secreted" protein need not dissociate entirely from the cell to be considered a secreted protein.

As used herein the term "hexose" refers to a monosaccharide with six carbon atoms and includes but is not limited to galactose, mannose and fructose.

As used herein "viral deactivation" or "viral inactivation" refers to the deactivation, inactivation or removal of virus from the cell culture. This may be done using, for example, Triton X-100 detergent (e.g., at a concentration of about 0.2% to about 1.5%, or about 0.2% to about 1.0% Triton X-100) with techniques known within the skill of the art.

B. Proteins Produced by the Present Invention

Generally, the methods and compositions of the present invention are useful for the production of recombinant proteins. Recombinant proteins are proteins produced by the process of genetic engineering. Preferred proteins for production according to the methods and compositions of the invention are protein-based therapeutics, also known as biologics. Preferably, the proteins are secreted as extracellular products such as antibodies. Production of recombinant DNA capable of coding for recombinant proteins including recombinant antibodies is well known in the art.

The term "antibody" or "antibodies", as used herein, is intended to refer to immunoglobulin molecules comprised of four polypeptide chains, two heavy (H) chains and two light (L) chains connected by disulfide bonds. Antibodies capable of being produced by the present invention include but are not limited to recombinant human antibodies including human monoclonal antibodies and 'fully' human monoclonal antibodies. Examples of antibodies which may be produced using the methods and compositions of the invention include tumor necrosis factor (TNF)-α antibodies (also referred to as anti-TNFα antibodies). TNFα antibodies which may be produced using the invention include adalimumab (adalimumab is sold under the trademark Humira® and is described in further detail in U.S. Pat. Nos. 6,090,382; 6,258,562; 6,509,015; and 8,664,945, each of which is incorporated herein by reference in its entirety), infliximab (infliximab is sold under the trademark REMICADE® Remicade is a registered trademark of Janssen Biotech, Inc.), certolizumab pegol (pegol is sold under the trademark CIMZIA®; Cimzia is a registered trademark of UCB Pharma, SA) and golimumab (golimumab is sold under the trademark SIMPONI®; Simponi is a registered trademark of Johnson & Johnson). Other antibodies that may be produced by the methods of this invention include natalizumab (natalizumab is sold under the trademark TYSABRI®; Tysabri is a registered trademark of Biogen Idec MA, Inc.), ranibizumab (ranibizumab is sold under the trademark LUCENTIS®; Lucentis is a registered trademark of Genentech, Inc.), bevicizumab (bevicizumab is sold under the trademark AVASTIN®; Avastin is a registered trademark of Genentech, Inc.), rituximab (rituximab is sold under the trademark RITUXAN®; Rituxan is a registered trademark of Biogen Idec, Inc.), eculizumab (eculizumab is sold under the trademark SOLIRIS®; Soliris is a registered trademark of Alexion Pharmaceuticals, Inc.), ustekinumab (ustekinumab is sold under the trademark STELARA®; Stelara is a registered trademark of Johnson & Johnson, Inc.), denosumab (denosumab is sold under the trademarks PROLIA®; Prolia is a registered trademark of Amgen, Inc. and XGEVA®; Xgeva is a registered trademark of Amgen, Inc.), tocilizumab (tocilizumab is sold under the trademark ACTEMRA®; Actemra is a registered trademark of Chugai Seiyaku Kabushiki Kaisha Corp.), ipilimumab (ipilimumab is sold under the trademark YERVOY®; Yervoy is a registered trademark of Bristol-Myers Squibb Comp.), omalizumab (omalizumab is sold under the trademark XOLAIR®; Xolair is a registered trademark of Novartis AG), ramucirumab (ramucirumab is sold under the trademark CYRAMZA®; Cyramza is a registered trademark of ImClone LLC), vedolizumab (vedolizumab is sold under the trademark ENTYVIO®; Entyvio is a registered trademark of Millennium Pharmaceuticals, Inc.), belimumab (belimumab is sold under the trademark BENLYSTA®; Benlysta is a registered trademark of GlaxoSmithKline Intellectual Property Limited), epratuzumab, nivolumab, secukinumab, gevokizumab and biosimilars thereof.

The term "biosimilar" or "biosimilars", as used herein, refers to a biological product designed to have active properties similar to an FDA-licensed biological product.

The invention may also be used to produce antibody fragments. The term "antibody fragment", as used herein, refers to one or more fragments of an antibody that retain the ability to specifically bind to an antigen ("antigen-binding portion"; e.g., hTNFα). Examples of antigen binding portions which may be produced by the methods of the invention are described in further detail in U.S. Pat. Nos. 6,090,382; 6,258,562; 6,509,015 and 8,664,945 each of which is incorporated herein by reference in its entirety. Production of antibody fragments or portions using the methods and compositions of the invention are also included within scope of the invention.

The methods and compositions of the present invention are also useful for the production of fusion proteins. Fusion proteins are proteins consisting of 2 or more protein domains derived from different genes. Production of recombinant DNA capable of coding for fusion proteins is well known in the art. Examples of fusion proteins include etanercept (etanercept is sold under the trademark Enbrel®; Enbrel is a registered trademark of Immunex) or a biosimilar thereof. Etanercept consists of the extracellular domain of the human p75 tumor necrosis factor-α receptor and the Fc domain of the human IgG1 antibody.

Cell Culture Media

Cell culture media of the present invention are exemplified by but are not limited to cell culture media meeting the following requirements. Cell culture media of the present invention include all cell culture media described in the specification. For example, a cell culture medium can be a chemically-defined liquid culture medium, an animal-derived component free liquid culture medium, a serum-free liquid culture medium, a serum-containing liquid culture medium, or a serum-free liquid culture medium.

In one embodiment the present invention provides cell culture media for use in mammalian cell culture for the production of recombinant proteins including antibodies or fragments thereof.

The various cell culture media described herein may be used separately or together for culturing cells.

In one embodiment, the glucose concentration in the first cell culture medium, the cell culture medium, or the cell culture growth medium) is from about 0.1 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, about 5.5 g/L, about 5 g/L, about 4.5 g/L, about 4.0 g/L, about 3.5 g/L, about 3.0 g/L, about 2.5 g/L, about 2.0 g/L, about 1.5 g/L, about 1.0 g/L, or about 0.5 g/L; about 0.5 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, about 5.5 g/L, about 5 g/L, about 4.5 g/L, about 4.0 g/L, about 3.5 g/L, about 3.0 g/L, about 2.5 g/L, about 2.0 g/L, about 1.5 g/L, or about 1.0 g/L; about 1.0 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, about 5.5 g/L, about 5 g/L, about 4.5 g/L, about 4.0 g/L, about 3.5 g/L, about 3.0 g/L, about 2.5 g/L, about 2.0 g/L, or about 1.5 g/L; about 1.5 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, about 5.5 g/L, about 5 g/L, about 4.5 g/L, about 4.0 g/L, about 3.5 g/L, about 3.0 g/L, about 2.5 g/L, or about 2.0 g/L; about 2.0 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, about 5.5 g/L, about 5 g/L, about 4.5 g/L, about 4.0 g/L, about 3.5 g/L, about 3.0 g/L, or about 2.5 g/L; about 2.5 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, about 5.5 g/L, about 5 g/L, about 4.5 g/L, about 4.0 g/L, about 3.5 g/L, or about 3.0 g/L; about 3.0 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, about 5.5 g/L, about 5 g/L, about 4.5 g/L, about 4.0 g/L, or about 3.5 g/L; about 3.5 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, about 5.5 g/L, about 5 g/L, about 4.5 g/L, or about 4.0 g/L; about 4.0 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, about 5.5 g/L, about 5 g/L, or about 4.5 g/L; about 4.5 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, about 5.5 g/L, or about 5 g/L; about 5.0 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, or about 5.5 g/L; about 5.5 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, or about 6 g/L; about 6.0 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, or 6.5 g/L; about 6.5 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, or about 7 g/L; about 7.0 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, or about 7.5 g/L; about 7.5 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, or about 8 g/L; about 8.0 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, or about 8.5 g/L; about 8.5 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, or about 9.0 g/L; about 9.0 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, or about 9.5 g/L; about 9.5 g/L to about 20 g/L, about 19 g/L, about 18 g/L, about 17 g/L, about 16 g/L, about 15 g/L, about 14 g/L, about 13 g/L, about 12 g/L, about 11 g/L, or about 10 g/L; about 10 g/L to about 20 g/L, about 19 g/L, about 18 g/L, about 17 g/L, about 16 g/L, about 15 g/L, about 14 g/L, about 13 g/L, about 12 g/L, or about 11 g/L; about 11 g/L to about 20 g/L, about 19 g/L, about 18 g/L, about 17 g/L, about 16 g/L, about 15 g/L, about 14 g/L, about 13 g/L, or about 12 g/L; about 12 g/L to about 20 g/L, about 19 g/L, about 18 g/L, about 17 g/L, about 16 g/L, about 15 g/L, about 14 g/L, or about 13 g/L; about 13 g/L to about 20 g/L, about 19 g/L, about 18 g/L, about 17 g/L, about 16 g/L, about 15 g/L, or about 14 g/L; about 14 g/L to about 20 g/L, about 19 g/L, about 18 g/L, about 17 g/L, about 16 g/L, or about 15 g/L; about 15 g/L to about 20 g/L, about 19 g/L, about 18 g/L, about 17 g/L, or about 16 g/L; about 16 g/L to about 20 g/L, about 19 g/L, about 18 g/L, or about 17 g/L; about 17 g/L to about 20 g/L, about 19 g/L, or about 18 g/L; about 18 g/L to about 20 g/L or 19 g/L; or about 19 g/L to about 20 g/L.

In one embodiment, the glucose concentration in the first cell culture medium, the cell growth culture medium, or the culture medium is from 0.1 g/L to 0.9 g/L, about 0.8 g/L, about 0.7 g/L, about 0.6 g/L, about 0.5 g/L, about 0.4 g/L, about 0.3 g/L, or about 0.1 g/L; about 0.2 g/L to about 0.9 g/L, about 0.8 g/L, about 0.7 g/L, about 0.6 g/L, about 0.5 g/L, about 0.4 g/L, or about 0.3 g/L; about 0.3 g/L to about 0.9 g/L, about 0.8 g/L, about 0.7 g/L, about 0.6 g/L, about 0.5 g/L, or about 0.4 g/L; about 0.4 g/L to about 0.9 g/L, about 0.8 g/L, about 0.7 g/L, about 0.6 g/L, or about 0.5 g/L; about 0.5 g/L to about 0.9 g/L, about 0.8 g/L, about 0.7 g/L, or about 0.6 g/L; about 0.6 g/L to about 0.9 g/L, about 0.8 g/L, or about 0.7 g/L; about 0.7 g/L to about 0.9 g/L or about 0.8 g/L; or about 0.8 g/L to about 0.9 g/L. In another embodiment the glucose concentration in the glucose concentration in the first cell culture medium, the cell growth culture medium, or the cell culture medium is from about 2.0 to about 4.0 g/L, about 3.8 g/L, about 3.6 g/L, about 3.4 g/L, about 3.2 g/L, about 3.0 g/L, about 2.8 g/L, about 2.6 g/L, about 2.4 g/L, or about 2.2 g/L; about 2.2 g/L to about 4.0 g/L, about 3.8 g/L, about 3.6 g/L, about 3.4 g/L, about 3.2 g/L, about 3.0 g/L, about 2.8 g/L, about 2.6 g/L, or about 2.4 g/L; about 2.4 g/L to about 4.0 g/L, about 3.8 g/L, about 3.6 g/L, about 3.4 g/L, about 3.2 g/L, about 3.0 g/L, about 2.8 g/L, about 2.6 g/L, or about 2.4 g/L; about 2.4 g/L to about 4.0 g/L, about 3.8 g/L, about 3.6 g/L, about 3.4 g/L, about 3.2 g/L, about 3.0 g/L, about 2.8 g/L, or about 2.6 g/L; about 2.6 g/L to about 4.0 g/L, about 3.8 g/L, about 3.6 g/L, about 3.4 g/L, about 3.2 g/L, about 3.0 g/L, or about 2.8 g/L; about 2.8 g/L to about 4.0 g/L, about 3.8 g/L, about 3.6 g/L, about 3.4 g/L, about 3.2 g/L, or about 3.0 g/L; about 3.0 g/L to about 4.0 g/L, about 3.8 g/L, about 3.6 g/L, 3.4 g/L, or about 3.2 g/L; about 3.2 g/L to about 4.0 g/L, about 3.8 g/L, about 3.6 g/L, or about 3.4 g/L; about 3.4 g/L to about 4.0 g/L, about 3.8 g/L, or about 3.6 g/L; about 3.6 g/L to about 4.0 g/L or about 3.8 g/L; or about 3.8 g/L to about 4.0 g/L. Methods for detecting the level of glucose in a culture medium are known in the art (e.g., using a glucose meter).

In one embodiment, the glucose concentration in the second cell culture medium, the cell culture production medium, or the recombinant protein production medium is from about 0.1 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, about 5.5 g/L, about 5 g/L, about 4.5 g/L, about 4.0 g/L, about 3.5 g/L, about 3.0 g/L, about 2.5 g/L, about 2.0 g/L, about 1.5 g/L, about 1.0 g/L, or about 0.5 g/L; about 0.5 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, about 5.5 g/L, about 5 g/L, about 4.5 g/L, about 4.0 g/L, about 3.5 g/L, about 3.0 g/L, about 2.5 g/L, about 2.0 g/L, about 1.5 g/L, or about 1.0 g/L; about 1.0 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, about 5.5 g/L, about 5 g/L, about 4.5 g/L, about 4.0 g/L, about 3.5 g/L, about 3.0 g/L, about 2.5 g/L, about 2.0 g/L, or about 1.5 g/L; about 1.5 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, about 5.5 g/L, about 5 g/L, about 4.5 g/L, about 4.0 g/L, about 3.5 g/L, about 3.0 g/L, about 2.5 g/L, or about 2.0 g/L; about 2.0 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, about 5.5 g/L, about 5 g/L, about 4.5 g/L, about 4.0 g/L, about 3.5 g/L, about 3.0 g/L, or about 2.5 g/L; about 2.5 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, about 5.5 g/L, about 5 g/L, about 4.5 g/L, about 4.0 g/L, about 3.5 g/L, or about 3.0 g/L; about 3.0 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, about 5.5 g/L, about 5 g/L, about 4.5 g/L, about 4.0 g/L, or about 3.5 g/L; about 3.5 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, about 5.5 g/L, about 5 g/L, about 4.5 g/L, or about 4.0 g/L; about 4.0 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, about 5.5 g/L, about 5 g/L, or about 4.5 g/L; about 4.5 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, about 5.5 g/L, or about 5 g/L; about 5.0 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, about 6 g/L, or about 5.5 g/L; about 5.5 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, about 6.5 g/L, or about 6 g/L; about 6.0 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, about 7 g/L, or 6.5 g/L; about 6.5 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, about 7.5 g/L, or about 7 g/L; about 7.0 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, about 8 g/L, or about 7.5 g/L; about 7.5 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, about 8.5 g/L, or about 8 g/L; about 8.0 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, about 9.0 g/L, or about 8.5 g/L; about 8.5 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, about 9.5 g/L, or about 9.0 g/L; about 9.0 g/L to about 20 g/L, about 19 g/L, about 18 g/L, about 17 g/L, about 16 g/L, about 15 g/L, about 14 g/L, about 13 g/L, about 12 g/L, about 11 g/L, about 10 g/L, or about 9.5 g/L; about 9.5 g/L to about 20 g/L, about 19 g/L, about 18 g/L, about 17 g/L, about 16 g/L, about 15 g/L, about 14 g/L, about 13 g/L, about 12 g/L, about 11 g/L, or about 10 g/L; about 10 g/L to about 20 g/L, about 19 g/L, about 18 g/L, about 17 g/L, about 16 g/L, about 15 g/L, about 14 g/L, about 13 g/L, about 12 g/L, or about 11 g/L; about 11 g/L to about 20 g/L, about 19 g/L, about 18 g/L, about 17 g/L, about 16 g/L, about 15 g/L, about 14 g/L, about 13 g/L, or about 12 g/L; about 12 g/L to about 20 g/L, about 19 g/L, about 18 g/L, about 17 g/L, about 16 g/L, about 15 g/L, about 14 g/L, or about 13 g/L; about 13 g/L to about 20 g/L, about 19 g/L, about 18 g/L, about 17 g/L, about 16 g/L, about 15 g/L, or about 14 g/L; about 14 g/L to about 20 g/L, about 19 g/L, about 18 g/L, about 17 g/L, about 16 g/L, or about 15 g/L; about 15 g/L to about 20 g/L, about 19 g/L, about 18 g/L, about 17 g/L, or about 16 g/L; about 16 g/L to about 20 g/L, about 19 g/L, about 18 g/L, or about 17 g/L; about 17 g/L to about 20 g/L, about 19 g/L, or about 18 g/L; about 18 g/L to about 20 g/L or 19 g/L; or about 19 g/L to about 20 g/L.

In one embodiment, the glucose concentration in the second cell culture medium, the cell culture production medium, or the recombinant protein production medium is from 0.1 g/L to 0.9 g/L, about 0.8 g/L, about 0.7 g/L, about 0.6 g/L, about 0.5 g/L, about 0.4 g/L, about 0.3 g/L, or about 0.1 g/L; about 0.2 g/L to about 0.9 g/L, about 0.8 g/L, about 0.7 g/L, about 0.6 g/L, about 0.5 g/L, about 0.4 g/L, or about 0.3 g/L; about 0.3 g/L to about 0.9 g/L, about 0.8 g/L, about 0.7 g/L, about 0.6 g/L, about 0.5 g/L, or about 0.4 g/L; about 0.4 g/L to about 0.9 g/L, about 0.8 g/L, about 0.7 g/L, about 0.6 g/L, or about 0.5 g/L; about 0.5 g/L to about 0.9 g/L, about 0.8 g/L, about 0.7 g/L, or about 0.6 g/L; about 0.6 g/L to about 0.9 g/L, about 0.8 g/L, or about 0.7 g/L; about 0.7 g/L to about 0.9 g/L or about 0.8 g/L; or about 0.8 g/L to about 0.9 g/L. In another embodiment the glucose concentration in the glucose concentration in the second cell culture medium, the cell culture production medium, or the recombinant protein production medium is about 2.0 g/L to about 4.0 g/L, about 3.8 g/L, about 3.6 g/L, about 3.4 g/L, about 3.2 g/L, about 3.0 g/L, about 2.8 g/L, about 2.6 g/L, about 2.4 g/L, or about 2.2 g/L; about 2.2 g/L to about 4.0 g/L, about 3.8 g/L, about 3.6 g/L, about 3.4 g/L, about 3.2 g/L, about 3.0 g/L, about 2.8 g/L, about 2.6 g/L, or about 2.4 g/L; about 2.4 g/L to about 4.0 g/L, about 3.8 g/L, about 3.6 g/L, about 3.4 g/L, about 3.2 g/L, about 3.0 g/L, about 2.8 g/L, about 2.6 g/L, or about 2.4 g/L; about 2.4 g/L to about 4.0 g/L, about 3.8 g/L, about 3.6 g/L, about 3.4 g/L, about 3.2 g/L, about 3.0 g/L, about 2.8 g/L, or about 2.6 g/L; about 2.6 g/L to about 4.0 g/L, about 3.8 g/L, about 3.6 g/L, about 3.4 g/L, about 3.2 g/L, about 3.0 g/L, or about 2.8 g/L; about 2.8 g/L to about 4.0 g/L, about 3.8 g/L, about 3.6 g/L, about 3.4 g/L, about 3.2 g/L, or about 3.0 g/L; about 3.0 g/L to about 4.0 g/L, about 3.8 g/L, about 3.6 g/L, 3.4 g/L, or about 3.2 g/L; about 3.2 g/L to about 4.0 g/L, about 3.8 g/L, about 3.6 g/L, or about 3.4 g/L; about 3.4 g/L to about 4.0 g/L, about 3.8 g/L, or about 3.6 g/L; about 3.6 g/L to about 4.0 g/L or about 3.8 g/L; or about 3.8 g/L to about 4.0 g/L.

In another embodiment, the glucose concentration is about 0.1 g/L to about 0.9 g/L (e.g., any of the exemplary subranges within about 0.1 g/L to about 0.9 g/L described herein) in the cell culture growth medium, the first culture medium, or the culture medium; and the glucose concentration is about 0.1 g/L to about 0.9 g/L (e.g., any of the exemplary subranges within about 0.1 g/L to about 0.9 g/L described herein) in the second culture medium, the cell culture production medium, or the recombinant protein culture medium.

In another embodiment the glucose concentration in about 2.0 g/L to about 4 g/L (e.g., any of the subranges within about 2.0 g/L to about 4.0 g/L described herein) in the cell culture growth medium, the first culture medium, or the culture medium; and the glucose concentration is 0.1 g/L to about 0.9 g/L (e.g., any of the subranges within about 0.1 g/L to about 0.9 g/L described herein) in the cell culture production medium, the second culture medium, or the recombinant protein culture medium.

In another embodiment, the cell culture media (e.g., any of the types of culture medium described herein) of the invention is serum-free, meaning that the medium contains no serum (e.g., fetal bovine serum (FBS), horse serum, goat serum, or any other animal-derived serum known to one skilled in the art In one embodiment, the present invention provides cell culture media including mammalian cells such as CHO cells or NS0 cells.

In another embodiment, the present invention provides cell culture media (e.g., any of the cell culture media described herein) optimized for the production of CHO cells which express anti-TNFα antibodies, more preferably fully human anti-TNFα antibodies, most preferably adalimumab.

In one embodiment, the cell culture production medium, the second medium, or the recombinant protein production medium has a pH ranging from about 6.8 to about 7.5, about 7.4, about 7.3, about 7.2, about 7.15, about 7.1, about 7.0, or about 6.9; about 6.9 to about 7.5, about 7.4, about 7.3, about 7.2, about 7.15, about 7.1, or about 7.0; about 7.0 to about 7.5, about 7.4, about 7.3, about 7.2, about 7.15, or about 7.1; about 7.1 to about 7.5, about 7.4, about 7.3, about 7.2, or about 7.15; about 7.15 to about 7.5, about 7.4, about 7.3, or about 7.2; about 7.2 to about 7.5, about 7.4, or about 7.3; about 7.3 to about 7.5 to about 7.4; or about 7.4 to about 7.5. For examples, the cell culture production medium can have a pH of about 6.8 to about 7.5, preferably from about 7.0 to about 7.3 and most preferably from about 7.1 to about 7.2. Numbers intermediate to the expressed ranges for pH (e.g., pH of 6.9 or 7.15) are also intended to be part of this invention.

Methods and Compositions for Protein Production

The present invention is directed toward mammalian cell culture. The introduction of DNA into mammalian host cells for purpose of expressing recombinant proteins is well known in the art. (See e.g., Taniyama, Y et al., Therapeutic option of plasmid-DNA based gene transfer, Curr Top Med Chem, 2012, 12(15), 1630-7). Selection of cells which have effectively incorporated the introduced DNA is well known in the art and is described in further detail in U.S. Pat. No. 6,210,924 which is incorporated in its entirety by reference.

Mammalian host cells suitable for the present invention include but are not limited to NS0, green monkey kidney epitheliVERO), baby hamster kidney fibroblast (BHK), human cervical cancer (HeLa), grivet kidney fibroblast (CV-1), dog kidney epithelium (MDCK), human embryonic kidney (HEK 293), mouse embryonic fibroblast (3T3), mouse myeloma (NS1), rat adrenal medulla (PC12), human lung fibroblast (WI38), PER.C6® (PER.C6 is a registered trademark of Crucell Holland, B.V.), and preferably CHO cells, including cell lines derived therefrom. CHO cells suitable for the present invention include but are not limited to the dihydrofolate reductase (DHFR)-deficient mutant cell lines, DXB1 and DG-44.

The methods of the present invention may be combined with cell culture methods known in the art. The methods of the present invention are useful to improve the production of recombinant polypeptides or proteins. Specifically, methods of the present invention include both single-phase and multiple-phase cell culture processes.

There are three types of cell culture processes generally used by those skilled in the art: perfusion, batch and fed-batch. These three types of cell cultures differ in the method used to supply the cell culture media. Perfusion culture includes the periodic or continuous replacement of the initial cell culture media with fresh media. Batch culture does not include any significant removal or any significant addition to the initial cell culture media. Fed-batch culture includes the supplementing of the initial cell culture media with particular cell culture components that are beneficial for the purpose of the cell culture, and that do not include the significant removal of cell culture or cell culture medium (e.g., any of the culture media described herein) during the culturing. This supplementing may occur in defined increments or may be continuous. Additional aspects and parameters of culturing, and bioreactors for use in culturing, are also described below.

After culturing using the methods and compositions of the present invention, the cultured cells and/or the expressed polypeptides or proteins are harvested. Harvesting of cultured cells and/or expressed polypeptide or proteins is well known in the art. (See, e.g., Chiang L-L et al., Optimizing parameters for clinical-scale production of high IL-12 secreting dendritic cells pulsed with oxidized whole tumor cell lysate, J Transl Med, 2011, 9, 198). Additional methods for harvesting the anti-TNFα antibody are known in the art.

Harvesting may include purification of the expressed polypeptide or protein. Purification of the expressed polypeptide or protein is well known in the art. (See e.g., Saraswat M. et al., Preparative Purification of Recombinant Proteins: Current Status and Future Trends, Biomed Res Int., 2013, 312709, p 1-18). Additional aspects of purifying an anti-TNFα antibody from a production cell culture medium, a second culture medium, or a recombinant protein production medium are described herein.

Perfusion Culturing

Perfusion culturing includes the removal a volume of the recombinant protein production medium and adding thereto a volume of the culture medium. The removal and adding can be performed simultaneously or sequentially, or a combination of the two. The removal and adding can be performed periodically or continuously.

In some examples, the removal and adding can be performed continuously (e.g., at a rate that removes and replaces a volume of about 0.1% to about 400% (e.g., about 1% to about 350%, about 1% to about 300%, about 1% to about 250%, about 1% to about 200%, about 1% to about 150%, about 1% to about 100%, about 1% to about 80%, about 1% to about 60%, about 1% to about 40%, about 1% to about 20%, about 5% to about 400%, about 5% to about 350%, about 5% to about 300%, about 5% to about 250%, about 5% to about 200%, about 5% to about 150%, about 5% to about 100%, about 5% to about 80%, about 5% to about 60%, about 5% to about 40%, about 5% to about 20%, about 10% to about 400%, about 10% to about 350%, about 10% to about 300%, about 10% to about 250%, about 10% to about 200%, about 10% to about 150%, about 10% to about 100%, about 10% to about 80%, about 10% to about 60%, about 10% to about 40%, about 10% to about 20%, about 20% to about 400%, about 20% to about 350%, about 20% to about 300%, about 20% to about 250%, about 20% to about 200%, about 20% to about 150%, about 20% to about 100%, about 20% to about 80%, about 20% to about 60%, about 20% to about 40%, about 40% to about 400%, about 40% to about 350%, about 40% to about 300%, about 40% to about 250%, about 40% to about 200%, about 40% to about 150%, about 40% to about 100%, about 40% to about 80%, about 40% to about 60%, about 60% to about 400%, about 60% to about 350%, about 60% to about 300%, about 60% to about 250%, about 60% to about 200%, about 60% to about 150%, about 60% to about 100%, about 60% to about 80%, about 80% to about 400%, about 80% to about 350%, about 80% to about 300%, about 80% to about 250%, about 80% to about 200%, about 80% to about 150%, about 80% to about 100%, about 100% to about 400%, about 100% to about 350%, about 100% to about 300%, about 100% to about 250%, about 100% to about 200%, about 100% to about 150%, about 150% to about 400%, about 150% to about 350%, about 150% to about 300%, about 150% to about 250%, about 150% to about 200%, about 200% to about 400%, about 200% to about 350%, about 200% to about 300%, about 200% to about 250%, about 250% to about 400%, about 250% to about 350%, about 250% to about 300%, about 300% to about 400%, about 300% to about 350%, or about 350% to about 400%) of the volume of the cell culture production medium, the second culture medium, or the recombinant protein production medium volume at the start of the period of time or the internal volume of the bioreactor that the culture is disposed in, over any given time period (e.g., over a 24-hour period or over a 48-hour period) or periodically (e.g., once every third day, once every other day, once a day, twice a day, three times a day, or four times a day), or any combination thereof. When the removal and adding is performed periodically, the volume that is removed or replaced (e.g., within about a 24-hour period or within a 48-hour period) can be, e.g., between 1% to 400% (e.g., about 1% to about 350%, about 1% to about 300%, about 1% to about 250%, about 1% to about 200%, about 1% to about 150%, about 1% to about 100%, about 1% to about 80%, about 1% to about 60%, about 1% to about 40%, about 1% to about 20%, about 5% to about 400%, about 5% to about 350%, about 5% to about 300%, about 5% to about 250%, about 5% to about 200%, about 5% to about 150%, about 5% to about 100%, about 5% to about 80%, about 5% to about 60%, about 5% to about 40%, about 5% to about 20%, about 10% to about 400%, about 10% to about 350%, about 10% to about 300%, about 10% to about 250%, about 10% to about 200%, about 10% to about 150%, about 10% to about 100%, about 10% to about 80%, about 10% to about 60%, about 10% to about 40%, about 10% to about 20%, about 20% to about 400%, about 20% to about 350%, about 20% to about 300%, about 20% to about 250%, about 20% to about 200%, about 20% to about 150%, about 20% to about 100%, about 20% to about 80%, about 20% to about 60%, about 20% to about 40%, about 40% to about 400%, about 40% to about 350%, about 40% to about 300%, about 40% to about 250%, about 40% to about 200%, about 40% to about 150%, about 40% to about 100%, about 40% to about 80%, about 40% to about 60%, about 60% to about 400%, about 60% to about 350%, about 60% to about 300%, about 60% to about 250%, about 60% to about 200%, about 60% to about 150%, about 60% to about 100%, about 60% to about 80%, about 80% to about 400%, about 80% to about 350%, about 80% to about 300%, about 80% to about 250%, about 80% to about 200%, about 80% to about 150%, about 80% to about 100%, about 100% to about 400%, about 100% to about 350%, about 100% to about 300%, about 100% to about 250%, about 100% to about 200%, about 100% to about 150%, about 150% to about 400%, about 150% to about 350%, about 150% to about 300%, about 150% to about 250%, about 150% to about 200%, about 200% to about 400%, about 200% to about 350%, about 200% to about 300%, about 200% to about 250%, about 250% to about 400%, about 250% to about 350%, about 250% to about 300%, about 300% to about 400%, about 300% to about 350%, or about 350% to about 400%) of the volume of the cell culture production medium, second culture medium, or recombinant protein production medium at the start of the period of time or the internal volume of the bioreactor that the culture is disposed in. The volume of the cell culture production medium, the second culture medium, or the recombinant protein production medium removed and the volume of the culture medium added can in some instances be approximately the same over each incremental time period (e.g., each 24-hour period or each 48-hour period) over the entire or part of the period of time. As is known in the art, the rate at which a volume of the cell culture production medium, the second culture medium, or the recombinant protein production medium is removed (volume/unit of time) and the rate at which a volume of the culture medium is added (volume/unit of time) can be varied. The rate at which a volume of the cell culture production medium, the second culture medium, or the recombinant protein production medium is removed and the rate at which a volume of the culture medium is added (volume/unit of time) can be about the same or can be different.

Alternatively, the volumes removed and added can change (e.g., gradually increase) over each incremental time period (e.g., each 24-hour period or 48-hour time period) during the period of time. For example the volume of the cell culture production medium, the second culture medium, or the recombinant protein production medium removed and the volume of the culture medium added within each incremental time period (e.g., each 24-hour period or 48-hour period) over the culturing period can be increased (e.g., gradually or through staggered increments) over the period of time from a volume that is between 1% to about 20% of the volume of the culture medium volume at the start of the period of time or the internal volume of the bioreactor that the culture is disposed in, to about 20% to about 400% of the volume of the cell culture production medium, the second culture medium, or the recombinant protein production medium at the start of the period of time or the internal volume of the bioreactor that the culture is disposed in.

Skilled practitioners will appreciate that the culture medium first contacted with recombinant cells to prepare a recombinant protein production medium, and the culture medium (typically known in the art as a feed culture or feed culture medium) added to an already obtained recombinant protein production medium can be the same or different.

A volume of the cell culture production medium, the second culture medium, or the recombinant protein production medium can be removed, e.g., by a mechanical system. Alternatively or in addition, a volume of the cell culture production medium, the second culture medium, or the recombinant protein production medium can be removed by seeping or gravity flow of the volume being removed through a sterile membrane with a molecular weight cut-off that excludes the cell (e.g., mammalian cell). The volume of culture medium can be added to the recombinant protein production medium in an automated fashion, e.g., by perfusion pump.

In some examples, the removing and adding is initiated once the recombinant mammalian cells reach a target viable cell density. For example, the target viable cell density is about $0.5 \times 10^6$ cells/milliliter ("mL") to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, about $6.5 \times 10^6$ cells/mL, about $6 \times 10^6$ cells/mL, about $5.5 \times 10^6$ cells/mL, about $5 \times 10^6$ cells/mL, about $4.5 \times 10^6$ cells/mL, about $4 \times 10^6$ cells/mL, about $3.5 \times 10^6$ cells/mL, about $3 \times 10^6$ cells/mL, about $2.5 \times 10^6$ cells/mL, about $2 \times 10^6$ cells/mL, about $1.5 \times 10^6$ cells/mL, or about $1 \times 10^6$ cells/mL; about $1.0 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, about $6.5 \times 10^6$ cells/mL, about $6 \times 10^6$ cells/mL, about $5.5 \times 10^6$ cells/mL, about $5 \times 10^6$ cells/mL, about $4.5 \times 10^6$ cells/mL, about $4 \times 10^6$ cells/mL, about $3.5 \times 10^6$ cells/mL, about $3 \times 10^6$ cells/mL, about $2.5 \times 10^6$ cells/mL, about $2 \times 10^6$ cells/mL, or about $1.5 \times 10^6$ cells/mL; about $1.5 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, about $6.5 \times 10^6$ cells/mL, about $6 \times 10^6$ cells/mL, about $5.5 \times 10^6$ cells/mL, about $5 \times 10^6$ cells/mL, about $4.5 \times 10^6$ cells/mL, about $4 \times 10^6$ cells/mL, about $3.5 \times 10^6$ cells/mL, about $3 \times 10^6$ cells/mL, about $2.5 \times 10^6$ cells/mL, or about $2 \times 10^6$ cells/mL; about $2 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, about $6.5 \times 10^6$ cells/mL, about $6 \times 10^6$ cells/mL, about $5.5 \times 10^6$ cells/mL, about $5 \times 10^6$ cells/mL, about $4.5 \times 10^6$ cells/mL, about $4 \times 10^6$ cells/mL, about $3.5 \times 10^6$ cells/mL, about $3 \times 10^6$ cells/mL, or about $2.5 \times 10^6$ cells/mL; about $2.5 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, about $6.5 \times 10^6$ cells/mL, about $6 \times 10^6$ cells/mL, about $5.5 \times 10^6$ cells/mL, about $5 \times 10^6$ cells/mL, about $4.5 \times 10^6$ cells/mL, about $4 \times 10^6$ cells/mL, about $3.5 \times 10^6$ cells/mL, or about $3 \times 10^6$ cells/mL; about $3 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, about $6.5 \times 10^6$ cells/mL, about $6 \times 10^6$ cells/mL, about $5.5 \times 10^6$ cells/mL, about $5 \times 10^6$ cells/mL, about $4.5 \times 10^6$ cells/mL, about $4 \times 10^6$ cells/mL, or about $3.5 \times 10^6$ cells/mL; about $3.5 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, about $6.5 \times 10^6$ cells/mL, about $6 \times 10^6$ cells/mL, about $5.5 \times 10^6$ cells/mL, about $5 \times 10^6$ cells/mL, or about $4 \times 10^6$ cells/mL; about $4 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, about $6.5 \times 10^6$ cells/mL, about $6 \times 10^6$ cells/mL, about $5.5 \times 10^6$ cells/mL, about $5 \times 10^6$ cells/mL, or about $4.5 \times 10^6$ cells/mL; about $4.5 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, about $6.5 \times 10^6$ cells/mL, about $6 \times 10^6$ cells/mL, about $5.5 \times 10^6$ cells/mL, or about $5 \times 10^6$ cells/mL; about $5 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, about $6.5 \times 10^6$ cells/mL, about $6 \times 10^6$ cells/mL, or about $5.5 \times 10^6$ cells/mL; about $6 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, or about $6.5 \times 10^6$ cells/mL; about $6.5 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, or about $7 \times 10^6$ cells/mL; about $7 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, or about $7.5 \times 10^6$ cells/mL; about $7.5 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5\times10^6$ cells/mL, about $11\times10^6$ cells/mL, about $10.5\times10^6$ cells/mL, about $10\times10^6$ cells/mL, about $9.5\times10^6$ cells/mL, about $9\times10^6$ cells/mL, about $8.5\times10^6$ cells/mL, or about $8\times10^6$ cells/mL; about $8\times10^6$ cells/mL to: about $15\times10^6$ cells/mL, about $14.5\times10^6$ cells/mL, about $14\times10^6$ cells/mL, about $13.5\times10^5$ cells/mL, about $13\times10^6$ cells/mL, about $12.5\times10^6$ cells/mL, about $12\times10^6$ cells/mL, about $11.5\times10^6$ cells/mL, about $11\times10^6$ cells/mL, about $10.5\times10^6$ cells/mL, about $10\times10^6$ cells/mL, about $9.5\times10^6$ cells/mL, about $9\times10^6$ cells/mL, or about $8.5\times10^6$ cells/mL; about $8.5\times10^6$ cells/mL to: about $15\times10^6$ cells/mL, about $14.5\times10^6$ cells/mL, about $14\times10^6$ cells/mL, about $13.5\times10^5$ cells/mL, about $13\times10^6$ cells/mL, about $12.5\times10^6$ cells/mL, about $12\times10^6$ cells/mL, about $11.5\times10^6$ cells/mL, about $11\times10^6$ cells/mL, about $10.5\times10^6$ cells/mL, or about $10\times10^6$ cells/mL; about $10\times10^6$ cells/mL to: about $15\times10^6$ cells/mL, about $14.5\times10^6$ cells/mL, about $14\times10^6$ cells/mL, about $13.5\times10^5$ cells/mL, about $13\times10^6$ cells/mL, about $12.5\times10^6$ cells/mL, about $12\times10^6$ cells/mL, about $11.5\times10^6$ cells/mL, about $11\times10^6$ cells/mL, or about $10.5\times10^6$ cells/mL; about $10.5\times10^6$ cells/mL to: about $15\times10^6$ cells/mL, about $14.5\times10^6$ cells/mL, about $14\times10^6$ cells/mL, about $13.5\times10^5$ cells/mL, about $13\times10^6$ cells/mL, about $12.5\times10^6$ cells/mL, about $12\times10^6$ cells/mL, about $11.5\times10^6$ cells/mL, or about $11\times10^6$ cells/mL; about $11\times10^6$ cells/mL to: about $15\times10^6$ cells/mL, about $14.5\times10^6$ cells/mL, about $14\times10^6$ cells/mL, about $13.5\times10^5$ cells/mL, about $13\times10^6$ cells/mL, about $12.5\times10^6$ cells/mL, or about $12\times10^6$ cells/mL; about $12\times10^6$ cells/mL to: about $15\times10^6$ cells/mL, about $14.5\times10^6$ cells/mL, about $14\times10^6$ cells/mL, about $13.5\times10^5$ cells/mL, about $13\times10^6$ cells/mL, or about $12.5\times10^6$ cells/mL; about $12.5\times10^6$ cells/mL to: about $15\times10^6$ cells/mL, about $14.5\times10^6$ cells/mL, about $14\times10^6$ cells/mL, about $13.5\times10^5$ cells/mL, or about $13\times10^6$ cells/mL; about $13\times10^6$ cells/mL to: about $15\times10^6$ cells/mL, about $14.5\times10^6$ cells/mL, about $14\times10^6$ cells/mL, or about $13.5\times10^5$ cells/mL; about $13.5\times10^6$ cells/mL to: about $15\times10^6$ cells/mL, about $14.5\times10^6$ cells/mL, or about $14\times10^6$ cells/mL; about $14\times10^6$ cells/mL to: about $15\times10^6$ cells/mL or about $14.5\times10^6$ cells/mL; or about $14.5\times10^6$ cells/mL to about $15\times10^6$ cells/mL.

In some examples, the removing and adding is initiated after about the first 24 hours, the first 36 hours, the first 48 hours, the first 60 hours, the first 72 hours, the first 84 hours, the first 96 hours, the first 108 hours, or the first 120 hours of the period of time. In some examples, the removing and adding is initiated at about 24 hours to about 96 hours (e.g., about 24 hours to about 92 hours, about 24 hours to about 88 hours, about 24 hours to about 84 hours, about 24 hours to about 80 hours, about 24 hours to about 76 hours, about 24 hours to about 72 hours, about 24 hours to about 68 hours, about 24 hours to about 64 hours, about 24 hours to about 60 hours, about 24 hours to about 56 hours, about 24 hours to about 52 hours, about 24 hours to about 48 hours, about 24 hours to about 44 hours, about 24 hours to about 40 hours, about 24 hours to about 36 hours, about 24 hours to about 32 hours, about 24 hours to about 28 hours, about 28 hours to about 92 hours, about 28 hours to about 88 hours, about 28 hours to about 84 hours, about 28 hours to about 80 hours, about 28 hours to about 76 hours, about 28 hours to about 72 hours, about 28 hours to about 68 hours, about 28 hours to about 64 hours, about 28 hours to about 60 hours, about 28 hours to about 56 hours, about 28 hours to about 52 hours, about 28 hours to about 48 hours, about 28 hours to about 44 hours, about 28 hours to about 40 hours, about 28 hours to about 36 hours, about 28 hours to about 32 hours, about 32 hours to about 92 hours, about 32 hours to about 88 hours, about 32 hours to about 84 hours, about 32 hours to about 80 hours, about 32 hours to about 76 hours, about 32 hours to about 72 hours, about 32 hours to about 68 hours, about 32 hours to about 64 hours, about 32 hours to about 60 hours, about 32 hours to about 56 hours, about 32 hours to about 52 hours, about 32 hours to about 48 hours, about 32 hours to about 44 hours, about 32 hours to about 40 hours, about 32 hours to about 36 hours, about 36 hours to about 92 hours, about 36 hours to about 88 hours, about 36 hours to about 84 hours, about 36 hours to about 80 hours, about 36 hours to about 76 hours, about 36 hours to about 72 hours, about 36 hours to about 68 hours, about 36 hours to about 64 hours, about 36 hours to about 60 hours, about 36 hours to about 56 hours, about 36 hours to about 52 hours, about 36 hours to about 48 hours, about 36 hours to about 44 hours, about 36 hours to about 40 hours, about 40 hours to about 92 hours, about 40 hours to about 88 hours, about 40 hours to about 84 hours, about 40 hours to about 80 hours, about 40 hours to about 76 hours, about 40 hours to about 72 hours, about 40 hours to about 68 hours, about 40 hours to about 64 hours, about 40 hours to about 60 hours, about 40 hours to about 56 hours, about 40 hours to about 52 hours, about 40 hours to about 48 hours, about 40 hours to about 44 hours, about 44 hours to about 92 hours, about 44 hours to about 88 hours, about 44 hours to about 84 hours, about 44 hours to about 80 hours, about 44 hours to about 76 hours, about 44 hours to about 72 hours, about 44 hours to about 68 hours, about 44 hours to about 64 hours, about 44 hours to about 60 hours, about 44 hours to about 56 hours, about 44 hours to about 52 hours, about 44 hours to about 48 hours, about 48 hours to about 92 hours, about 48 hours to about 88 hours, about 48 hours to about 84 hours, about 48 hours to about 80 hours, about 48 hours to about 76 hours, about 48 hours to about 72 hours, about 48 hours to about 68 hours, about 48 hours to about 64 hours, about 48 hours to about 60 hours, about 48 hours to about 56 hours, about 48 hours to about 52 hours, about 52 hours to about 92 hours, about 52 hours to about 88 hours, about 52 hours to about 84 hours, about 52 hours to about 80 hours, about 52 hours to about 76 hours, about 52 hours to about 72 hours, about 52 hours to about 68 hours, about 52 hours to about 64 hours, about 52 hours to about 60 hours, about 52 hours to about 56 hours, about 56 hours to about 92 hours, about 56 hours to about 88 hours, about 56 hours to about 84 hours, about 56 hours to about 80 hours, about 56 hours to about 76 hours, about 56 hours to about 72 hours, about 56 hours to about 68 hours, about 56 hours to about 64 hours, about 56 hours to about 60 hours, about 60 hours to about 92 hours, about 60 hours to about 88 hours, about 60 hours to about 84 hours, about 60 hours to about 80 hours, about 60 hours to about 76 hours, about 60 hours to about 72 hours, about 60 hours to about 68 hours, about 60 hours to about 64 hours, about 64 hours to about 92 hours, about 64 hours to about 88 hours, about 64 hours to about 84 hours, about 64 hours to about 80 hours, about 64 hours to about 76 hours, about 64 hours to about 72 hours, about 64 hours to about 68 hours, about 68 hours to about 92 hours, about 68 hours to about 88 hours, about 68 hours to about 84 hours, about 68 hours to about 80 hours, about 68 hours to about 76 hours, about 68 hours to about 72 hours, about 72 hours to about 92 hours, about 72 hours to about 88 hours, about 72 hours to about 84 hours, about 72 hours to about 80 hours, about 72 hours to about 76 hours, about 76 hours to about 92 hours, about 76 hours to about 88 hours, about 76 hours to about 84 hours, about 76 hours to about 80 hours, about 80 hours to about 92 hours, about 80 hours to about 88 hours, about 80 hours to about 84 hours, about 84 hours to about 92 hours, about 84 hours to about 88 hours, or about 88 hours to about 92 hours) into the first period of time.

Fed Batch Culturing

Fed batch culturing a cell in a fed-batch bioreactor includes, over the majority of the culturing period, the addition (e.g., periodic or continuous addition) to the cell culture production medium, the second culture medium, or the recombinant protein production medium of a volume of culture medium, without substantial or significant removal of the cell culture production medium, the second culture medium, or the recombinant protein production medium. The adding of the culture medium can be performed continuously (e.g., at a rate that adds a volume of between 1% to 400% (e.g., about 1% to about 350%, about 1% to about 300%, about 1% to about 250%, about 1% to about 200%, about 1% to about 150%, about 1% to about 100%, about 1% to about 80%, about 1% to about 60%, about 1% to about 40%, about 1% to about 20%, about 5% to about 400%, about 5% to about 350%, about 5% to about 300%, about 5% to about 250%, about 5% to about 200%, about 5% to about 150%, about 5% to about 100%, about 5% to about 80%, about 5% to about 60%, about 5% to about 40%, about 5% to about 20%, about 10% to about 400%, about 10% to about 350%, about 10% to about 300%, about 10% to about 250%, about 10% to about 200%, about 10% to about 150%, about 10% to about 100%, about 10% to about 80%, about 10% to about 60%, about 10% to about 40%, about 10% to about 20%, about 20% to about 400%, about 20% to about 350%, about 20% to about 300%, about 20% to about 250%, about 20% to about 200%, about 20% to about 150%, about 20% to about 100%, about 20% to about 80%, about 20% to about 60%, about 20% to about 40%, about 40% to about 400%, about 40% to about 350%, about 40% to about 300%, about 40% to about 250%, about 40% to about 200%, about 40% to about 150%, about 40% to about 100%, about 40% to about 80%, about 40% to about 60%, about 60% to about 400%, about 60% to about 350%, about 60% to about 300%, about 60% to about 250%, about 60% to about 200%, about 60% to about 150%, about 60% to about 100%, about 60% to about 80%, about 80% to about 400%, about 80% to about 350%, about 80% to about 300%, about 80% to about 250%, about 80% to about 200%, about 80% to about 150%, about 80% to about 100%, about 100% to about 400%, about 100% to about 350%, about 100% to about 300%, about 100% to about 250%, about 100% to about 200%, about 100% to about 150%, about 150% to about 400%, about 150% to about 350%, about 150% to about 300%, about 150% to about 250%, about 150% to about 200%, about 200% to about 400%, about 200% to about 350%, about 200% to about 300%, about 200% to about 250%, about 250% to about 400%, about 250% to about 350%, about 250% to about 300%, about 300% to about 400%, about 300% to about 350%, or about 350% to about 400%) of the volume of the cell culture production medium, the second culture medium, or the recombinant protein production medium at the start of the period of time or the internal volume of the bioreactor that the culture is disposed in, over an incremental time period (e.g., each 24-hour period or each 48-hour period), or periodically (e.g., once every third day, once every other day (48 hours), once a day (once every 24 hours), twice a day, three times a day, or four times a day), or any combination thereof. When the addition is performed periodically, the volume that is added over the incremental time period (e.g., each 24-hour period or each 48-hour period) can be, e.g., between 0.1% to 400% (e.g., about 1% to about 350%, about 1% to about 300%, about 1% to about 250%, about 1% to about 200%, about 1% to about 150%, about 1% to about 100%, about 1% to about 80%, about 1% to about 60%, about 1% to about 40%, about 1% to about 20%, about 1% to about 15%, about 1% to about 12%, about 1% to about 10%, about 2% to about 10%, 2% to about 8%, about 2% to about 6%, about 5% to about 400%, about 5% to about 350%, about 5% to about 300%, about 5% to about 250%, about 5% to about 200%, about 5% to about 150%, about 5% to about 100%, about 5% to about 80%, about 5% to about 60%, about 5% to about 40%, about 5% to about 20%, about 5% to about 10%, about 5% to about 8%, about 10% to about 400%, about 10% to about 350%, about 10% to about 300%, about 10% to about 250%, about 10% to about 200%, about 10% to about 150%, about 10% to about 100%, about 10% to about 80%, about 10% to about 60%, about 10% to about 40%, about 10% to about 20%, about 20% to about 400%, about 20% to about 350%, about 20% to about 300%, about 20% to about 250%, about 20% to about 200%, about 20% to about 150%, about 20% to about 100%, about 20% to about 80%, about 20% to about 60%, about 20% to about 40%, about 40% to about 400%, about 40% to about 350%, about 40% to about 300%, about 40% to about 250%, about 40% to about 200%, about 40% to about 150%, about 40% to about 100%, about 40% to about 80%, about 40% to about 60%, about 60% to about 400%, about 60% to about 350%, about 60% to about 300%, about 60% to about 250%, about 60% to about 200%, about 60% to about 150%, about 60% to about 100%, about 60% to about 80%, about 80% to about 400%, about 80% to about 350%, about 80% to about 300%, about 80% to about 250%, about 80% to about 200%, about 80% to about 150%, about 80% to about 100%, about 100% to about 400%, about 100% to about 350%, about 100% to about 300%, about 100% to about 250%, about 100% to about 200%, about 100% to about 150%, about 150% to about 400%, about 150% to about 350%, about 150% to about 300%, about 150% to about 250%, about 150% to about 200%, about 200% to about 400%, about 200% to about 350%, about 200% to about 300%, about 200% to about 250%, about 250% to about 400%, about 250% to about 350%, about 250% to about 300%, about 300% to about 400%, about 300% to about 350%, or about 350% to about 400%) of the volume of the cell culture production medium, the second culture medium, or the recombinant protein production medium at the start of the period of time or the internal volume of the bioreactor that the culture is disposed in. The volume of the culture medium added can in some instances be held approximately the same over each 24-hour period or each 48-hour period over the entire or part of the period of time. As is known in the art, the rate at which the volume of the culture medium is added (volume/unit of time) can be varied over the entire or part of the period of time. For example, the volume of the culture medium added can change (e.g., gradually increase) over each 24-hour period or 48-hour period during the culturing period. For example the volume of the culture medium added within each 24-hour period or 48-hour period over the period of time can be increased (e.g., gradually or through staggered increments) over the culturing period from a volume that is between 1% to about 20% of the volume of the cell culture production medium, the second culture medium, or the recombinant protein production medium at the start of the period of time or the internal volume of the bioreactor that the culture is disposed in, to about 20% to about 400% of the volume of the culture medium at the start of the period of time or the internal volume of the bioreactor that the culture is disposed in. The rate at which the volume of the culture medium is added (volume/unit of time) can be about the same over the entire or part of the culturing period.

Skilled practitioners will appreciate that the culture medium first contacted with the recombinant cells to produce a recombinant protein production medium, and the culture medium (typically referred to as a feed culture or feed culture medium) added to an already prepared recombinant protein production medium can be the same type of media. In other instances, the initial culture medium and the later added culture medium (i.e. feed culture medium) can be different. The subsequently added culture medium (i.e., the feed culture medium) can be added to the already existing recombinant protein production medium an automated fashion, e.g., by perfusion pump.

In some examples, the adding of a culture medium (i.e., a feed culture medium) to an already prepared cell culture production medium, second culture medium, or the recombinant protein production medium is initiated once the recombinant mammalian cells reach a target viable cell density. For example, the target viable cell density can be about $0.5 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, about $6.5 \times 10^6$ cells/mL, about $6 \times 10^6$ cells/mL, about $5.5 \times 10^6$ cells/mL, about $5 \times 10^6$ cells/mL, about $4.5 \times 10^6$ cells/mL, about $4 \times 10^6$ cells/mL, about $3.5 \times 10^6$ cells/mL, about $3 \times 10^6$ cells/mL, about $2.5 \times 10^6$ cells/mL, about $2 \times 10^6$ cells/mL, about $1.5 \times 10^6$ cells/mL, or about $1 \times 10^6$ cells/mL; about $1.0 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, about $6.5 \times 10^6$ cells/mL, about $6 \times 10^6$ cells/mL, about $5.5 \times 10^6$ cells/mL, about $5 \times 10^6$ cells/mL, about $4.5 \times 10^6$ cells/mL, about $4 \times 10^6$ cells/mL, about $3.5 \times 10^6$ cells/mL, about $3 \times 10^6$ cells/mL, about $2.5 \times 10^6$ cells/mL, about $2 \times 10^6$ cells/mL, or about $1.5 \times 10^6$ cells/mL; about $1.5 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, about $6.5 \times 10^6$ cells/mL, about $6 \times 10^6$ cells/mL, about $5.5 \times 10^6$ cells/mL, about $5 \times 10^6$ cells/mL, about $4.5 \times 10^6$ cells/mL, about $4 \times 10^6$ cells/mL, about $3.5 \times 10^6$ cells/mL, about $3 \times 10^6$ cells/mL, about $2.5 \times 10^6$ cells/mL, or about $2 \times 10^6$ cells/mL; about $2 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, about $6.5 \times 10^6$ cells/mL, about $6 \times 10^6$ cells/mL, about $5.5 \times 10^6$ cells/mL, about $5 \times 10^6$ cells/mL, about $4.5 \times 10^6$ cells/mL, about $4 \times 10^6$ cells/mL, about $3.5 \times 10^6$ cells/mL, or about $2.5 \times 10^6$ cells/mL; about $2.5 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, about $6.5 \times 10^6$ cells/mL, about $6 \times 10^6$ cells/mL, about $5.5 \times 10^6$ cells/mL, about $5 \times 10^6$ cells/mL, about $4.5 \times 10^6$ cells/mL, about $4 \times 10^6$ cells/mL, about $3.5 \times 10^6$ cells/mL, or about $3 \times 10^6$ cells/mL; about $3 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, about $6.5 \times 10^6$ cells/mL, about $6 \times 10^6$ cells/mL, about $5.5 \times 10^6$ cells/mL, about $5 \times 10^6$ cells/mL, about $4.5 \times 10^6$ cells/mL, or about $3.5 \times 10^6$ cells/mL; about $3.5 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, about $6.5 \times 10^6$ cells/mL, about $6 \times 10^6$ cells/mL, about $5.5 \times 10^6$ cells/mL, about $5 \times 10^6$ cells/mL, about $4.5 \times 10^6$ cells/mL, or about $4 \times 10^6$ cells/mL; about $4 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, about $6.5 \times 10^6$ cells/mL, about $6 \times 10^6$ cells/mL, about $5.5 \times 10^6$ cells/mL, about $5 \times 10^6$ cells/mL, or about $4.5 \times 10^6$ cells/mL; about $4.5 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, about $6.5 \times 10^6$ cells/mL, about $6 \times 10^6$ cells/mL, about $5.5 \times 10^6$ cells/mL, or about $5 \times 10^6$ cells/mL; about $5 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, about $6.5 \times 10^6$ cells/mL, about $6 \times 10^6$ cells/mL, or about $5.5 \times 10^6$ cells/mL; about $6 \times 10^6$ cells/mL to: about $15 \times 10^6$ cells/mL, about $14.5 \times 10^6$ cells/mL, about $14 \times 10^6$ cells/mL, about $13.5 \times 10^5$ cells/mL, about $13 \times 10^6$ cells/mL, about $12.5 \times 10^6$ cells/mL, about $12 \times 10^6$ cells/mL, about $11.5 \times 10^6$ cells/mL, about $11 \times 10^6$ cells/mL, about $10.5 \times 10^6$ cells/mL, about $10 \times 10^6$ cells/mL, about $9.5 \times 10^6$ cells/mL, about $9 \times 10^6$ cells/mL, about $8.5 \times 10^6$ cells/mL, about $8 \times 10^6$ cells/mL, about $7.5 \times 10^6$ cells/mL, about $7 \times 10^6$ cells/mL, or about 6.5×10⁶ cells/mL; about 6.5×10⁶ cells/mL to: about 15×10⁶ cells/mL, about 14.5×10⁶ cells/mL, about 14×10⁶ cells/mL, about 13.5×10⁵ cells/mL, about 13×10⁶ cells/mL, about 12.5×10⁶ cells/mL, about 12×10⁶ cells/mL, about 11.5×10⁶ cells/mL, about 11×10⁶ cells/mL, about 10.5×10⁶ cells/mL, about 10×10⁶ cells/mL, about 9.5×10⁶ cells/mL, about 9×10⁶ cells/mL, about 8.5×10⁶ cells/mL, about 8×10⁶ cells/mL, about 7.5×10⁶ cells/mL, or about 7×10⁶ cells/mL; about 7×10⁶ cells/mL to: about 15×10⁶ cells/mL, about 14.5×10⁶ cells/mL, about 14×10⁶ cells/mL, about 13.5×10⁵ cells/mL, about 13×10⁶ cells/mL, about 12.5×10⁶ cells/mL, about 12×10⁶ cells/mL, about 11.5×10⁶ cells/mL, about 11×10⁶ cells/mL, about 10.5×10⁶ cells/mL, about 10×10⁶ cells/mL, about 9.5×10⁶ cells/mL, about 9×10⁶ cells/mL, about 8.5×10⁶ cells/mL, about 8×10⁶ cells/mL, or about 7.5×10⁶ cells/mL; about 7.5×10⁶ cells/mL to: about 15×10⁶ cells/mL, about 14.5×10⁶ cells/mL, about 14×10⁶ cells/mL, about 13.5×10⁵ cells/mL, about 13×10⁶ cells/mL, about 12.5×10⁶ cells/mL, about 12×10⁶ cells/mL, about 11.5×10⁶ cells/mL, about 11×10⁶ cells/mL, about 10.5×10⁶ cells/mL, about 10×10⁶ cells/mL, about 9.5×10⁶ cells/mL, about 9×10⁶ cells/mL, about 8.5×10⁶ cells/mL, or about 8×10⁶ cells/mL; about 8×10⁶ cells/mL to: about 15×10⁶ cells/mL, about 14.5×10⁶ cells/mL, about 14×10⁶ cells/mL, about 13.5×10⁵ cells/mL, about 13×10⁶ cells/mL, about 12.5×10⁶ cells/mL, about 12×10⁶ cells/mL, about 11.5×10⁶ cells/mL, about 11×10⁶ cells/mL, about 10.5×10⁶ cells/mL, about 10×10⁶ cells/mL, about 9.5×10⁶ cells/mL, about 9×10⁶ cells/mL, or about 8.5×10⁶ cells/mL; about 8.5×10⁶ cells/mL to: about 15×10⁶ cells/mL, about 14.5×10⁶ cells/mL, about 14×10⁶ cells/mL, about 13.5×10⁵ cells/mL, about 13×10⁶ cells/mL, about 12.5×10⁶ cells/mL, about 12×10⁶ cells/mL, about 11.5×10⁶ cells/mL, about 11×10⁶ cells/mL, about 10.5×10⁶ cells/mL, or about 10×10⁶ cells/mL; about 10×10⁶ cells/mL to: about 15×10⁶ cells/mL, about 14.5×10⁶ cells/mL, about 14×10⁶ cells/mL, about 13.5×10⁵ cells/mL, about 13×10⁶ cells/mL, about 12.5×10⁶ cells/mL, about 12×10⁶ cells/mL, about 11.5×10⁶ cells/mL, about 11×10⁶ cells/mL, or about 10.5×10⁶ cells/mL; about 10.5×10⁶ cells/mL to: about 15×10⁶ cells/mL, about 14.5×10⁶ cells/mL, about 14×10⁶ cells/mL, about 13.5×10⁵ cells/mL, about 13×10⁶ cells/mL, about 12.5×10⁶ cells/mL, about 12×10⁶ cells/mL, about 11.5×10⁶ cells/mL, or about 11×10⁶ cells/mL; about 11×10⁶ cells/mL to: about 15×10⁶ cells/mL, about 14.5×10⁶ cells/mL, about 14×10⁶ cells/mL, about 13.5×10⁵ cells/mL, about 13×10⁶ cells/mL, about 12.5×10⁶ cells/mL, or about 12×10⁶ cells/mL; about 12×10⁶ cells/mL to: about 15×10⁶ cells/mL, about 14.5×10⁶ cells/mL, about 14×10⁶ cells/mL, about 13.5×10⁵ cells/mL, about 13×10⁶ cells/mL, or about 12.5×10⁶ cells/mL; about 12.5×10⁶ cells/mL to: about 15×10⁶ cells/mL, about 14.5×10⁶ cells/mL, about 14×10⁶ cells/mL, about 13.5×10⁵ cells/mL, or about 13×10⁶ cells/mL; about 13×10⁶ cells/mL to: about 15×10⁶ cells/mL, about 14.5×10⁶ cells/mL, about 14×10⁶ cells/mL, or about 13.5×10⁵ cells/mL; about 13.5×10⁶ cells/mL to: about 15×10⁶ cells/mL, about 14.5×10⁶ cells/mL, or about 14×10⁶ cells/mL; about 14×10⁶ cells/mL to: about 15×10⁶ cells/mL or about 14.5×10⁶ cells/mL; or about 14.5×10⁶ cells/mL to about 15×10⁶ cells/mL.

In some examples, the adding of the culture medium to an already prepared cell culture production medium, second culture medium, or recombinant protein production medium is initiated after about the first 24 hours, the first 36 hours, the first 48 hours, the first 60 hours, the first 72 hours, the first 84 hours, the first 96 hours, the first 108 hours, or the first 120 hours of the period of time. In some examples, the adding of the culture medium to the already prepared cell culture production medium, the second culture medium, or the recombinant protein production medium is initiated at about 24 hours to about 96 hours (e.g., about 24 hours to about 92 hours, about 24 hours to about 88 hours, about 24 hours to about 84 hours, about 24 hours to about 80 hours, about 24 hours to about 76 hours, about 24 hours to about 72 hours, about 24 hours to about 68 hours, about 24 hours to about 64 hours, about 24 hours to about 60 hours, about 24 hours to about 56 hours, about 24 hours to about 52 hours, about 24 hours to about 48 hours, about 24 hours to about 44 hours, about 24 hours to about 40 hours, about 24 hours to about 36 hours, about 24 hours to about 32 hours, about 24 hours to about 28 hours, about 28 hours to about 92 hours, about 28 hours to about 88 hours, about 28 hours to about 84 hours, about 28 hours to about 80 hours, about 28 hours to about 76 hours, about 28 hours to about 72 hours, about 28 hours to about 68 hours, about 28 hours to about 64 hours, about 28 hours to about 60 hours, about 28 hours to about 56 hours, about 28 hours to about 52 hours, about 28 hours to about 48 hours, about 28 hours to about 44 hours, about 28 hours to about 40 hours, about 28 hours to about 36 hours, about 28 hours to about 32 hours, about 32 hours to about 92 hours, about 32 hours to about 88 hours, about 32 hours to about 84 hours, about 32 hours to about 80 hours, about 32 hours to about 76 hours, about 32 hours to about 72 hours, about 32 hours to about 68 hours, about 32 hours to about 64 hours, about 32 hours to about 60 hours, about 32 hours to about 56 hours, about 32 hours to about 52 hours, about 32 hours to about 48 hours, about 32 hours to about 44 hours, about 32 hours to about 40 hours, about 32 hours to about 36 hours, about 36 hours to about 92 hours, about 36 hours to about 88 hours, about 36 hours to about 84 hours, about 36 hours to about 80 hours, about 36 hours to about 76 hours, about 36 hours to about 72 hours, about 36 hours to about 68 hours, about 36 hours to about 64 hours, about 36 hours to about 60 hours, about 36 hours to about 56 hours, about 36 hours to about 52 hours, about 36 hours to about 48 hours, about 36 hours to about 44 hours, about 36 hours to about 40 hours, about 40 hours to about 92 hours, about 40 hours to about 88 hours, about 40 hours to about 84 hours, about 40 hours to about 80 hours, about 40 hours to about 76 hours, about 40 hours to about 72 hours, about 40 hours to about 68 hours, about 40 hours to about 64 hours, about 40 hours to about 60 hours, about 40 hours to about 56 hours, about 40 hours to about 52 hours, about 40 hours to about 48 hours, about 40 hours to about 44 hours, about 44 hours to about 92 hours, about 44 hours to about 88 hours, about 44 hours to about 84 hours, about 44 hours to about 80 hours, about 44 hours to about 76 hours, about 44 hours to about 72 hours, about 44 hours to about 68 hours, about 44 hours to about 64 hours, about 44 hours to about 60 hours, about 44 hours to about 56 hours, about 44 hours to about 52 hours, about 44 hours to about 48 hours, about 48 hours to about 92 hours, about 48 hours to about 88 hours, about 48 hours to about 84 hours, about 48 hours to about 80 hours, about 48 hours to about 76 hours, about 48 hours to about 72 hours, about 48 hours to about 68 hours, about 48 hours to about 64 hours, about 48 hours to about 60 hours, about 48 hours to about 56 hours, about 48 hours to about 52 hours, about 52 hours to about 92 hours, about 52 hours to about 88 hours, about 52 hours to about 84 hours, about 52 hours to about 80 hours, about 52 hours to about 76 hours, about 52 hours to about 72 hours, about 52 hours to about 68 hours, about 52 hours to about 64 hours, about 52 hours to about 60 hours, about 52 hours to about 56 hours, about 56 hours to about 92 hours, about 56 hours to about 88 hours, about 56 hours to about 84 hours, about 56 hours to about 80 hours, about 56 hours to about 76 hours, about 56 hours to about 72 hours, about 56 hours to about 68 hours, about 56 hours to about 64 hours, about 56 hours to about 60 hours, about 60 hours to about 92 hours, about 60 hours to about 88 hours, about 60 hours to about 84 hours, about 60 hours to about 80 hours, about 60 hours to about 76 hours, about 60 hours to about 72 hours, about 60 hours to about 68 hours, about 60 hours to about 64 hours, about 64 hours to about 92 hours, about 64 hours to about 88 hours, about 64 hours to about 84 hours, about 64 hours to about 80 hours, about 64 hours to about 76 hours, about 64 hours to about 72 hours, about 64 hours to about 68 hours, about 68 hours to about 92 hours, about 68 hours to about 88 hours, about 68 hours to about 84 hours, about 68 hours to about 80 hours, about 68 hours to about 76 hours, about 68 hours to about 72 hours, about 72 hours to about 92 hours, about 72 hours to about 88 hours, about 72 hours to about 84 hours, about 72 hours to about 80 hours, about 72 hours to about 76 hours, about 76 hours to about 92 hours, about 76 hours to about 88 hours, about 76 hours to about 84 hours, about 76 hours to about 80 hours, about 80 hours to about 92 hours, about 80 hours to about 88 hours, about 80 hours to about 84 hours, about 84 hours to about 92 hours, about 84 hours to about 88 hours, or about 88 hours to about 92 hours) into the first period of time.

Bioreactors

In some examples, the culturing is performed using a shake flask. In some examples, the culturing is performed using a bioreactor (e.g., a fed batch bioreactor or a perfusion bioreactor). As is known in the art, a bioreactor can be equipped with several ports for, e.g., the removal of a fluid (e.g., culture medium that is substantially free of mammalian cells) or the addition of a fluid (e.g., a feed culture medium or a basic or acidic solution for regulating the pH). A bioreactor can also be equipped with a pH monitor, a dissolved oxygen monitor, a dissolved $CO_2$ monitor, one or more gas spargers, and a means for agitating the culture medium (e.g., a propeller). A variety of different bioreactors are commercially available. A bioreactor can also be equipped with a mechanical device that is capable of removing a volume of culture medium from the bioreactor and optionally, a filter within the mechanical device that removes the cells from the culture medium during the process of transfer of the culture medium out of the bioreactor (e.g., an ATF system).

The internal volume of a bioreactor (e.g., a perfusion bioreactor or a fed batch bioreactor) can be about 100 mL to about 25,000 L, about 100 mL to about 24,000 L, about 100 mL to about 22,000 L, about 100 mL to about 20,000 L, about 100 mL to about 18,000 L, about 100 mL to about 16,000 L, about 100 mL to about 14,000 L, about 100 mL to about 12,000 L, about 100 mL to about 10,000 L, about 100 mL to about 8,000 L, about 100 mL to about 6,000 L, about 100 mL to about 5,000 L, about 100 mL to about 4,000 L, about 100 mL to about 3,000 L, about 100 mL to about 2,000 L, about 100 mL to about 1,000 L, about 100 mL to about 500 L, about 100 mL to about 100 L, about 100 mL to about 50 L, about 500 mL to about 25,000 L, about 500 mL to about 24,000 L, about 500 mL to about 22,000 L, about 500 mL to about 20,000 L, about 500 mL to about 18,000 L, about 500 mL to about 16,000 L, about 500 mL to about 14,000 L, about 500 mL to about 12,000 L, about 500 mL to about 10,000 L, about 500 mL to about 8,000 L, about 500 mL to about 6,000 L, about 500 mL to about 5,000 L, about 500 mL to about 4,000 L, about 500 mL to about 3,000 L, about 500 mL to about 2,000 L, about 500 mL to about 1,000 L, about 500 mL to about 500 L, about 500 mL to about 100 L, about 500 mL to about 50 L, about 1 L to about 25,000 L, about 1 L to about 24,000 L, about 1 L to about 22,000 L, about 1 L to about 20,000 L, about 1 L to about 18,000 L, about 1 L to about 16,000 L, about 1 L to about 14,000 L, about 1 L to about 12,000 L, about 1 L to about 10,000 L, about 1 L to about 8,000 L, about 1 L to about 6,000 L, about 1 L to about 5,000 L, about 1 L to about 4,000 L, about 1 L to about 3,000 L, about 1 L to about 2,000 L, about 1 L to about 1,000 L, about 1 L to about 500 L, about 1 L to about 100 L, about 1 L to about 50 L, about 25 L to about 25,000 L, about 25 L to about 24,000 L, about 25 L to about 22,000 L, about 25 L to about 20,000 L, about 25 L to about 18,000 L, about 25 L to about 16,000 L, about 25 L to about 14,000 L, about 25 L to about 12,000 L, about 25 L to about 10,000 L, about 25 L to about 8,000 L, about 25 L to about 6,000 L, about 25 L to about 5,000 L, about 25 L to about 4,000 L, about 25 L to about 3,000 L, about 25 L to about 2,000 L, about 25 L to about 1,000 L, about 25 L to about 500 L, about 25 L to about 100 L, about 25 L to about 50 L, about 50 L to about 25,000 L, about 50 L to about 24,000 L, about 50 L to about 22,000 L, about 50 L to about 20,000 L, about 50 L to about 18,000 L, about 50 L to about 16,000 L, about 50 L to about 14,000 L, about 50 L to about 12,000 L, about 50 L to about 10,000 L, about 50 L to about 8,000 L, about 50 L to about 6,000 L, about 50 L to about 5,000 L, about 50 L to about 4,000 L, about 50 L to about 3,000 L, about 50 L to about 2,000 L, about 50 L to about 1,000 L, about 50 L to about 500 L, about 50 L to about 100 L, about 100 L to about 25,000 L, about 100 L to about 24,000 L, about 100 L to about 22,000 L, about 100 L to about 20,000 L, about 100 L to about 18,000 L, about 100 L to about 16,000 L, about 100 L to about 14,000 L, about 100 L to about 12,000 L, about 100 L to about 10,000 L, about 100 L to about 8,000 L, about 100 L to about 6,000 L, about 100 L to about 5,000 L, about 100 L to about 4,000 L, about 100 L to about 3,000 L, about 100 L to about 2,000 L, about 100 L to about 1,000 L, about 100 L to about 500 L, about 200 L to about 25,000 L, about 200 L to about 24,000 L, about 200 L to about 22,000 L, about 200 L to about 20,000 L, about 200 L to about 18,000 L, about 200 L to about 16,000 L, about 200 L to about 14,000 L, about 200 L to about 12,000 L, about 200 L to about 10,000 L, about 200 L to about 8,000 L, about 200 L to about 6,000 L, about 200 L to about 5,000 L, about 200 L to about 4,000 L, about 200 L to about 3,000 L, about 200 L to about 2,000 L, about 200 L to about 1,000 L, about 200 L to about 500 L, about 500 L to about 25,000 L, about 500 L to about 24,000 L, about 500 L to about 22,000 L, about 500 L to about 20,000 L, about 500 L to about 18,000 L, about 500 L to about 16,000 L, about 500 L to about 14,000 L, about 500 L to about 12,000 L, about 500 L to about 10,000 L, about 500 L to about 8,000 L, about 500 L to about 6,000 L, about 500 L to about 5,000 L, about 500 L to about 4,000 L, about 500 L to about 3,000 L, about 500 L to about 2,000 L, about 500 L to about 1,000 L, about 1,000 L to about 25,000 L, about 1,000 L to about 24,000 L, about 1,000 L to about 22,000 L, about 1,000 L to about 20,000 L, about 1,000 L to about 18,000 L, about 1,000 L to about 16,000 L, about 1,000 L to about 14,000 L, about 1,000 L to about 12,000 L, about 1,000 L to about 10,000 L, about 1,000 L to about 8,000 L, about 1,000 L to about 6,000 L, about 1,000 L to about 5,000 L, about 1,000 L to about 4,000 L, about 1,000 L to about 3,000 L, about 1,000 L to about 2,000 L, about 2,000 L to about 25,000 L, about 2,000 L to about 24,000 L, about 2,000 L to about 22,000 L, about 2,000 L to about 20,000 L, about 2,000 L to about 18,000 L, about 2,000 L to about 16,000 L, about 2,000 L to about 14,000 L, about 2,000 L to about 12,000 L, about 2,000 L to about 10,000 L, about 2,000 L to about 8,000 L, about 2,000 L to about 6,000 L, about 2,000 L to about 5,000 L, about 2,000 L to about 4,000 L, about 4,000 L to about 25,000 L, about 4,000 L to about 24,000 L, about 4,000 L to about 22,000 L, about 4,000 L to about 20,000 L, about 4,000 L to about 18,000 L, about 4,000 L to about 16,000 L, about 4,000 L to about 14,000 L, about 4,000 L to about 12,000 L, about 4,000 L to about 10,000 L, about 4,000 L to about 8,000 L, about 4,000 L to about 6,000 L, about 6,000 L to about 25,000 L, about 6,000 L to about 24,000 L, about 6,000 L to about 22,000 L, about 6,000 L to about 20,000 L, about 6,000 L to about 18,000 L, about 6,000 L to about 16,000 L, about 6,000 L to about 14,000 L, about 6,000 L to about 12,000 L, about 6,000 L to about 10,000 L, about 6,000 L to about 8,000 L, about 8,000 L to about 25,000 L, about 8,000 L to about 24,000 L, about 8,000 L to about 22,000 L, about 8,000 L to about 20,000 L, about 8,000 L to about 18,000 L, about 8,000 L to about 16,000 L, about 8,000 L to about 14,000 L, about 8,000 L to about 12,000 L, about 8,000 L to about 10,000 L, about 10,000 L to about 25,000 L, about 10,000 L to about 24,000 L, about 10,000 L to about 22,000 L, about 10,000 L to about 20,000 L, about 10,000 L to about 18,000 L, about 10,000 L to about 16,000 L, about 10,000 L to about 14,000 L, about 10,000 L to about 12,000 L, about 12,000 L to about 25,000 L, about 12,000 L to about 24,000 L, about 12,000 L to about 22,000 L, about 12,000 L to about 20,000 L, about 12,000 L to about 18,000 L, about 12,000 L to about 16,000 L, about 12,000 L to about 14,000 L, about 14,000 L to about 25,000 L, about 14,000 L to about 24,000 L, about 14,000 L to about 22,000 L, about 14,000 L to about 20,000 L, about 14,000 L to about 18,000 L, about 14,000 L to about 16,000 L, about 16,000 L to about 25,000 L, about 16,000 L to about 24,000 L, about 16,000 L to about 22,000 L, about 16,000 L to about 20,000 L, about 16,000 L to about 18,000 L, about 18,000 L to about 25,000 L, about 18,000 L to about 24,000 L, about 18,000 L to about 22,000 L, about 18,000 L to about 20,000 L, or about 20,000 L to about 25,000 L.

Period of Time

In some examples, the period of time is between about 5 days to about 40 days (e.g., about 5 days to: about 39 days, about 38 days, about 37 days, about 36 days, about 35 days, about 34 days, about 33 days, about 32 days, about 31 days, about 30 days, about 29 days, about 28 days, about 27 days, about 26 days, about 25 days, about 24 days, about 23 days, about 22 days, about 21 days, about 20 days, about 19 days, about 18 days, about 17 days, about 16 days, about 15 days, about 14 days, about 13 days, about 12 days, about 11 days, about 10 days, about 9 days, about 8 days, or about 7 days; about 6 days to: about 40 days, about 39 days, about 38 days, about 37 days, about 36 days, about 35 days, about 34 days, about 33 days, about 32 days, about 31 days, about 30 days, about 29 days, about 28 days, about 27 days, about 26 days, about 25 days, about 24 days, about 23 days, about 22 days, about 21 days, about 20 days, about 19 days, about 18 days, about 17 days, about 16 days, about 15 days, about 14 days, about 13 days, about 12 days, about 11 days, about 10 days, about 9 days, or about 8 days; about 7 days to: about 40 days, about 39 days, about 38 days, about 37 days, about 36 days, about 35 days, about 34 days, about 33 days, about 32 days, about 31 days, about 30 days, about 29 days, about 28 days, about 27 days, about 26 days, about 25 days, about 24 days, about 23 days, about 22 days, about 21 days, about 20 days, about 19 days, about 18 days, about 17 days, about 16 days, about 15 days, about 14 days, about 13 days, about 12 days, about 11 days, about 10 days, or about 9 days; about 8 days to: about 40 days, about 39 days, about 38 days, about 37 days, about 36 days, about 35 days, about 34 days, about 33 days, about 32 days, about 31 days, about 30 days, about 29 days, about 28 days, about 27 days, about 26 days, about 25 days, about 24 days, about 23 days, about 22 days, about 21 days, about 20 days, about 19 days, about 18 days, about 17 days, about 16 days, about 15 days, about 14 days, about 13 days, about 12 days, about 11 days, or about 10 days; about 9 days to: about 40 days, about 39 days, about 38 days, about 37 days, about 36 days, about 35 days, about 34 days, about 33 days, about 32 days, about 31 days, about 30 days, about 29 days, about 28 days, about 27 days, about 26 days, about 25 days, about 24 days, about 23 days, about 22 days, about 21 days, about 20 days, about 19 days, about 18 days, about 17 days, about 16 days, about 15 days, about 14 days, about 13 days, about 12 days, or about 11 days; about 10 days to: about 40 days, about 39 days, about 38 days, about 37 days, about 36 days, about 35 days, about 34 days, about 33 days, about 32 days, about 31 days, about 30 days, about 29 days, about 28 days, about 27 days, about 26 days, about 25 days, about 24 days, about 23 days, about 22 days, about 21 days, about 20 days, about 19 days, about 18 days, about 17 days, about 16 days, about 15 days, about 14 days, about 13 days, or about 12 days; about 11 days to: about 40 days, about 39 days, about 38 days, about 37 days, about 36 days, about 35 days, about 34 days, about 33 days, about 32 days, about 31 days, about 30 days, about 29 days, about 28 days, about 27 days, about 26 days, about 25 days, about 24 days, about 23 days, about 22 days, about 21 days, about 20 days, about 19 days, about 18 days, about 17 days, about 16 days, about 15 days, about 14 days, or about 13 days; about 12 days to: about 40 days, about 39 days, about 38 days, about 37 days, about 36 days, about 35 days, about 34 days, about 33 days, about 32 days, about 31 days, about 30 days, about 29 days, about 28 days, about 27 days, about 26 days, about 25 days, about 24 days, about 23 days, about 22 days, about 21 days, about 20 days, about 19 days, about 18 days, about 17 days, about 16 days, about 15 days, or about 14 days; about 13 days to: about 40 days, about 39 days, about 38 days, about 37 days, about 36 days, about 35 days, about 34 days, about 33 days, about 32 days, about 31 days, about 30 days, about 29 days, about 28 days, about 27 days, about 26 days, about 25 days, about 24 days, about 23 days, about 22 days, about 21 days, about 20 days, about 19 days, about 18 days, about 17 days, about 16 days, or about 15 days; about 14 days to: about 40 days, about 39 days, about 38 days, about 37 days, about 36 days, about 35 days, about 34 days, about 33 days, about 32 days, about 31 days, about 30 days, about 29 days, about 28 days, about 27 days, about 26 days, about 25 days, about 24 days, about 23 days, about 22 days, about 21 days, about 20 days, about 19 days, about 18 days, about 17 days, or about 16 days; about 15 days to: about 40 days, about 39 days, about 38 days, about 37 days, about 36 days, about 35 days, about 34 days, about 33 days, about 32 days, about 31 days, about 30 days, about 29 days, about 28 days, about 27 days, about 26 days, about 25 days, about 24 days, about 23 days, about 22 days, about 21 days, about 20 days, about 19 days, about 18 days, or about 17 days; about 16 days to: about 40 days, about 39 days, about 38 days, about 37 days, about 36 days, about 35 days, about 34 days, about 33 days, about 32 days, about 31 days, about 30 days, about 29 days, about 28 days, about 27 days, about 26 days, about 25 days, about 24 days, about 23 days, about 22 days, about 21 days, about 20 days, about 19 days, or about 18 days; about 17 days to: about 40 days, about 39 days, about 38 days, about 37 days, about 36 days, about 35 days, about 34 days, about 33 days, about 32 days, about 31 days, about 30 days, about 29 days, about 28 days, about 27 days, about 26 days, about 25 days, about 24 days, about 23 days, about 22 days, about 21 days, about 20 days, or about 19 days; about 18 days to: about 40 days, about 39 days, about 38 days, about 37 days, about 36 days, about 35 days, about 34 days, about 33 days, about 32 days, about 31 days, about 30 days, about 29 days, about 28 days, about 27 days, about 26 days, about 25 days, about 24 days, about 23 days, about 22 days, or about 21 days; about 20 days to: about 40 days, about 39 days, about 38 days, about 37 days, about 36 days, about 35 days, about 34 days, about 33 days, about 32 days, about 31 days, about 30 days, about 29 days, about 28 days, about 27 days, about 26 days, about 25 days, about 24 days, about 23 days, or about 22 days; about 21 days to: about 40 days, about 39 days, about 38 days, about 37 days, about 36 days, about 35 days, about 34 days, about 33 days, about 32 days, about 31 days, about 30 days, about 29 days, about 28 days, about 27 days, about 26 days, about 25 days, about 24 days, or about 23 days; about 22 days to: about 40 days, about 39 days, about 38 days, about 37 days, about 36 days, about 35 days, about 34 days, about 33 days, about 32 days, about 31 days, about 30 days, about 29 days, about 28 days, about 27 days, about 26 days, about 25 days, or about 24 days; about 23 days to: about 40 days, about 39 days, about 38 days, about 37 days, about 36 days, about 35 days, about 34 days, about 33 days, about 32 days, about 31 days, about 30 days, about 29 days, about 28 days, about 27 days, about 26 days, or about 25 days; about 24 days to: about 40 days, about 39 days, about 38 days, about 37 days, about 36 days, about 35 days, about 34 days, about 33 days, about 32 days, about 31 days, about 30 days, about 29 days, about 28 days, about 27 days, or about 26 days; about 25 days to: about 40 days, about 39 days, about 38 days, about 37 days, about 36 days, about 35 days, about 34 days, about 33 days, about 32 days, about 31 days, about 30 days, about 29 days, about 28 days, or about 27 days; about 26 days to: about 40 days, about 39 days, about 38 days, about 37 days, about 36 days, about 35 days, about 34 days, about 33 days, about 32 days, about 31 days, about 30 days, about 29 days, or about 28 days; about 27 days to: about 40 days, about 39 days, about 38 days, about 37 days, about 36 days, about 35 days, about 34 days, about 33 days, about 32 days, about 31 days, about 30 days, or about 29 days; about 28 days to: about 40 days, about 39 days, about 38 days, about 37 days, about 36 days, about 35 days, about 34 days, about 33 days, about 32 days, about 31 days, or about 30 days; about 29 days to: about 40 days, about 39 days, about 38 days, about 37 days, about 36 days, about 35 days, about 34 days, about 33 days, about 32 days, or about 31 days; about 30 days to: about 40 days, about 39 days, about 38 days, about 37 days, about 36 days, about 35 days, about 34 days, about 33 days, or about 32 days; about 31 days to: about 40 days, about 39 days, about 38 days, about 37 days, about 36 days, about 35 days, about 34 days, or about 33 days; about 32 days to: about 40 days, about 39 days, about 38 days, about 37 days, about 36 days, about 35 days, or about 34 days; about 33 days to: about 40 days, about 39 days, about 38 days, about 37 days, about 36 days, or about 35 days; about 34 days to: about 40 days, about 39 days, about 38 days, about 37 days, or about 36 days; about 35 days to: about 40 days, about 39 days, about 38 days, or about 37 days; about 36 days to: about 40 days, about 39 days, or about 38 days; about 37 days to: about 40 days or about 39 days; or about 38 days to about 40 days.

Monitoring and Maintaining Glucose Concentration

Particular parameters of a cell culture medium (e.g. a predetermined glucose level) can be maintained by utilizing a setpoint control system including a feedback control system. Feedback control systems are well known in the art. (See e.g., Craven, S. et al., Glucose concentration control of a fed-batch mammalian cell bioprocess using a nonlinear model predictive controller, *J of Process Control*, 2014, 24, 344-57). Setpoint control systems may be used to continuously monitor particular parameters or may be used to determine a particular feed profile. Once a feed profile is determined using a setpoint control system, monitoring is no longer necessary.

Temperature and Temperature Shift

During culturing, the temperature of a culture medium (e.g., any of the types of culture medium described herein, such as the recombinant protein production medium) can be about 31° C. to about 40° C. Skilled practitioners will appreciate that the temperature of a culture medium (e.g., any of the types of culture media described herein, such as a recombinant protein production medium) can be changed at a specific time point(s) during the culturing step. For example, the temperature of the culture medium can be changed or shifted (e.g., increased or decreased) at about one day, two days, three days, four days, five days, six days, seven days, eight days, nine days, ten days, eleven days, twelve days, fourteen days, fifteen days, sixteen days, seventeen days, eighteen days, nineteen days, or about twenty days or more into the first period of time. For example, the shifting of the temperature is performed at about 3 days to about 10 days (e.g., about 3 days to about 9 days, about 3 days to about 8 days, about 3 days to about 7 days, about 3 days to about 6 days, about 3 days to about 5 days, about 3 days to about 4 days, about 4 days to about 10 days, about 4 days to about 9 days, about 4 days to about 8 days, about 4 days to about 7 days, about 4 days to about 6 days, about 4 days to about 5 days, about 5 days to about 10 days, about 5 days to about 9 days, about 5 days to about 8 days, about 5 days to about 7 days, about 6 days to about 10 days, about 6 days to about 9 days, about 6 days to about 8 days, about 6 days to about 7 days, about 7 days to about 10 days, about 7 days to about 9 days, about 7 days to about 8 days, about 8 days to about 10 days, about 8 days to about 9 days, or about 9 days to about 10 days) into the first period of time. For example, the shifting of the temperature is performed when the recombinant mammalian cells reach a predetermined viable cell density in the culture medium. In some examples, the predetermined viable cell density is about $1.0 \times 10^6$ cells/mL to about $10 \times 10^6$ cells/mL (e.g., about $1.0 \times 10^6$ cells/mL to about $9.5 \times 10^6$ cells/mL, about $1.0 \times 10^6$ cells/mL to about $9.0 \times 10^6$ cells/mL, about $1.0 \times 10^6$ cells/mL to about $8.5 \times 10^6$ cells/mL, about $1.0 \times 10^6$ cells/mL to about $8.0 \times 10^6$ cells/mL, about $1.0 \times 10^6$ cells/mL to about $7.5 \times 10^6$ cells/mL, about $1.0 \times 10^6$ cells/mL to about $7.0 \times 10^6$ cells/mL, about $1.0 \times 10^6$ cells/mL to about $6.5 \times 10^6$ cells/mL, about $1.0 \times 10^6$ cells/mL to about $6.0 \times 10^6$ cells/mL, about $1.0 \times 10^6$ cells/mL to about $5.5 \times 10^6$ cells/mL, about $1.0 \times 10^6$ cells/mL to about $5.0 \times 10^6$ cells/mL, about $1.0 \times 10^6$ cells/mL to about $4.5 \times 10^6$ cells/mL, about $1.0 \times 10^6$ cells/mL to about $4.0 \times 10^6$ cells/mL, about $1.0 \times 10^6$ cells/mL to about $3.5 \times 10^6$ cells/mL, about $1.0 \times 10^6$ cells/mL to about $3.0 \times 10^6$ cells/mL, about $1.0 \times 10^6$ cells/mL to about $2.5 \times 10^6$ cells/mL, about $1.0 \times 10^6$ cells/mL to about $2.0 \times 10^6$ cells/mL, about $1.0 \times 10^6$ cells/mL to about $1.5 \times 10^6$ cells/mL, about $1.5 \times 10^6$ cells/mL to about $10 \times 10^6$ cells/mL, about $1.5 \times 10^6$ cells/mL to about $9.5 \times 10^6$ cells/mL, about $1.5 \times 10^6$ cells/mL to about $9.0 \times 10^6$ cells/mL, about $1.5 \times 10^6$ cells/mL to about $8.5 \times 10^6$ cells/mL, about 1.5×10⁶ cells/mL to about 8.0×10⁶ cells/mL, about 1.5×10⁶ cells/mL to about 7.5×10⁶ cells/mL, about 1.5×10⁶ cells/mL to about 7.0×10⁶ cells/mL, about 1.5×10⁶ cells/mL to about 6.5×10⁶ cells/mL, about 1.5×10⁶ cells/mL to about 6.0×10⁶ cells/mL, about 1.5×10⁶ cells/mL to about 5.5×10⁶ cells/mL, about 1.5×10⁶ cells/mL to about 5.0×10⁶ cells/mL, about 1.5×10⁶ cells/mL to about 4.5×10⁶ cells/mL, about 1.5×10⁶ cells/mL to about 4.0×10⁶ cells/mL, about 1.5×10⁶ cells/mL to about 3.5×10⁶ cells/mL, about 1.5×10⁶ cells/mL to about 3.0×10⁶ cells/mL, about 1.5×10⁶ cells/mL to about 2.5×10⁶ cells/mL, about 1.5×10⁶ cells/mL to about 2.0×10⁶ cells/mL, about 2.0×10⁶ cells/mL to about 10×10⁶ cells/mL, about 2.0×10⁶ cells/mL to about 9.5×10⁶ cells/mL, about 2.0×10⁶ cells/mL to about 9.0×10⁶ cells/mL, about 2.0×10⁶ cells/mL to about 8.5×10⁶ cells/mL, about 2.0×10⁶ cells/mL to about 8.0×10⁶ cells/mL, about 2.0×10⁶ cells/mL to about 7.5×10⁶ cells/mL, about 2.0×10⁶ cells/mL to about 7.0×10⁶ cells/mL, about 2.0×10⁶ cells/mL to about 6.5×10⁶ cells/mL, about 2.0×10⁶ cells/mL to about 6.0×10⁶ cells/mL, about 2.0×10⁶ cells/mL to about 5.5×10⁶ cells/mL, about 2.0×10⁶ cells/mL to about 5.0×10⁶ cells/mL, about 2.0×10⁶ cells/mL to about 4.5×10⁶ cells/mL, about 2.0×10⁶ cells/mL to about 4.0×10⁶ cells/mL, about 2.0×10⁶ cells/mL to about 3.5×10⁶ cells/mL, about 2.0×10⁶ cells/mL to about 3.0×10⁶ cells/mL, about 2.0×10⁶ cells/mL to about 2.5×10⁶ cells/mL, about 2.5×10⁶ cells/mL to about 10×10⁶ cells/mL, about 2.5×10⁶ cells/mL to about 9.5×10⁶ cells/mL, about 2.5×10⁶ cells/mL to about 9.0×10⁶ cells/mL, about 2.5×10⁶ cells/mL to about 8.5×10⁶ cells/mL, about 2.5×10⁶ cells/mL to about 8.0×10⁶ cells/mL, about 2.5×10⁶ cells/mL to about 7.5×10⁶ cells/mL, about 2.5×10⁶ cells/mL to about 7.0×10⁶ cells/mL, about 2.5×10⁶ cells/mL to about 6.5×10⁶ cells/mL, about 2.5×10⁶ cells/mL to about 6.0×10⁶ cells/mL, about 2.5×10⁶ cells/mL to about 5.5×10⁶ cells/mL, about 2.5×10⁶ cells/mL to about 5.0×10⁶ cells/mL, about 2.5×10⁶ cells/mL to about 4.5×10⁶ cells/mL, about 2.5×10⁶ cells/mL to about 4.0×10⁶ cells/mL, about 2.5×10⁶ cells/mL to about 3.5×10⁶ cells/mL, about 2.5×10⁶ cells/mL to about 3.0×10⁶ cells/mL, about 3.0×10⁶ cells/mL to about 10×10⁶ cells/mL, about 3.0×10⁶ cells/mL to about 9.5×10⁶ cells/mL, about 3.0×10⁶ cells/mL to about 9.0×10⁶ cells/mL, about 3.0×10⁶ cells/mL to about 8.5×10⁶ cells/mL, about 3.0×10⁶ cells/mL to about 8.0×10⁶ cells/mL, about 3.0×10⁶ cells/mL to about 7.5×10⁶ cells/mL, about 3.0×10⁶ cells/mL to about 7.0×10⁶ cells/mL, about 3.0×10⁶ cells/mL to about 6.5×10⁶ cells/mL, about 3.0×10⁶ cells/mL to about 6.0×10⁶ cells/mL, about 3.0×10⁶ cells/mL to about 5.5×10⁶ cells/mL, about 3.0×10⁶ cells/mL to about 5.0×10⁶ cells/mL, about 3.0×10⁶ cells/mL to about 4.5×10⁶ cells/mL, about 3.0×10⁶ cells/mL to about 4.0×10⁶ cells/mL, about 3.0×10⁶ cells/mL to about 3.5×10⁶ cells/mL, about 3.5×10⁶ cells/mL to about 10×10⁶ cells/mL, about 3.5×10⁶ cells/mL to about 9.5×10⁶ cells/mL, about 3.5×10⁶ cells/mL to about 9.0×10⁶ cells/mL, about 3.5×10⁶ cells/mL to about 8.5×10⁶ cells/mL, about 3.5×10⁶ cells/mL to about 8.0×10⁶ cells/mL, about 3.5×10⁶ cells/mL to about 7.5×10⁶ cells/mL, about 3.5×10⁶ cells/mL to about 7.0×10⁶ cells/mL, about 3.5×10⁶ cells/mL to about 6.5×10⁶ cells/mL, about 3.5×10⁶ cells/mL to about 6.0×10⁶ cells/mL, about 3.5×10⁶ cells/mL to about 5.5×10⁶ cells/mL, about 3.5×10⁶ cells/mL to about 5.0×10⁶ cells/mL, about 3.5×10⁶ cells/mL to about 4.5×10⁶ cells/mL, about 3.5×10⁶ cells/mL to about 4.0×10⁶ cells/mL, about 4.0×10⁶ cells/mL to about 10×10⁶ cells/mL, about 4.0×10⁶ cells/mL to about 9.5×10⁶ cells/mL, about 4.0×10⁶ cells/mL to about 9.0×10⁶ cells/mL, about 4.0×10⁶ cells/mL to about 8.5×10⁶ cells/mL, about 4.0×10⁶ cells/mL to about 8.0×10⁶ cells/mL, about 4.0×10⁶ cells/mL to about 7.5×10⁶ cells/mL, about 4.0×10⁶ cells/mL to about 7.0×10⁶ cells/mL, about 4.0×10⁶ cells/mL to about 6.5×10⁶ cells/mL, about 4.0×10⁶ cells/mL to about 6.0×10⁶ cells/mL, about 4.0×10⁶ cells/mL to about 5.5×10⁶ cells/mL, about 4.0×10⁶ cells/mL to about 5.0×10⁶ cells/mL, about 4.0×10⁶ cells/mL to about 4.5×10⁶ cells/mL, about 4.5×10⁶ cells/mL to about 10×10⁶ cells/mL, about 4.5×10⁶ cells/mL to about 9.5×10⁶ cells/mL, about 4.5×10⁶ cells/mL to about 9.0×10⁶ cells/mL, about 4.5×10⁶ cells/mL to about 8.5×10⁶ cells/mL, about 4.5×10⁶ cells/mL to about 8.0×10⁶ cells/mL, about 4.5×10⁶ cells/mL to about 7.5×10⁶ cells/mL, about 4.5×10⁶ cells/mL to about 7.0×10⁶ cells/mL, about 4.5×10⁶ cells/mL to about 6.5×10⁶ cells/mL, about 4.5×10⁶ cells/mL to about 6.0×10⁶ cells/mL, about 4.5×10⁶ cells/mL to about 5.5×10⁶ cells/mL, about 4.5×10⁶ cells/mL to about 5.0×10⁶ cells/mL, about 5.0×10⁶ cells/mL to about 10×10⁶ cells/mL, about 5.0×10⁶ cells/mL to about 9.5×10⁶ cells/mL, about 5.0×10⁶ cells/mL to about 9.0×10⁶ cells/mL, about 5.0×10⁶ cells/mL to about 8.5×10⁶ cells/mL, about 5.0×10⁶ cells/mL to about 8.0×10⁶ cells/mL, about 5.0×10⁶ cells/mL to about 7.5×10⁶ cells/mL, about 5.0×10⁶ cells/mL to about 7.0×10⁶ cells/mL, about 5.0×10⁶ cells/mL to about 6.5×10⁶ cells/mL, about 5.0×10⁶ cells/mL to about 6.0×10⁶ cells/mL, about 5.0×10⁶ cells/mL to about 5.5×10⁶ cells/mL, about 5.5×10⁶ cells/mL to about 10×10⁶ cells/mL, about 5.5×10⁶ cells/mL to about 9.5×10⁶ cells/mL, about 5.5×10⁶ cells/mL to about 9.0×10⁶ cells/mL, about 5.5×10⁶ cells/mL to about 8.5×10⁶ cells/mL, about 5.5×10⁶ cells/mL to about 8.0×10⁶ cells/mL, about 5.5×10⁶ cells/mL to about 7.5×10⁶ cells/mL, about 5.5×10⁶ cells/mL to about 7.0×10⁶ cells/mL, about 5.5×10⁶ cells/mL to about 6.5×10⁶ cells/mL, about 5.5×10⁶ cells/mL to about 6.0×10⁶ cells/mL, about 6.0×10⁶ cells/mL to about 10×10⁶ cells/mL, about 6.0×10⁶ cells/mL to about 9.5×10⁶ cells/mL, about 6.0×10⁶ cells/mL to about 9.0×10⁶ cells/mL, about 6.0×10⁶ cells/mL to about 8.5×10⁶ cells/mL, about 6.0×10⁶ cells/mL to about 8.0×10⁶ cells/mL, about 6.0×10⁶ cells/mL to about 7.5×10⁶ cells/mL, about 6.0×10⁶ cells/mL to about 7.0×10⁶ cells/mL, about 6.0×10⁶ cells/mL to about 6.5×10⁶ cells/mL, about 6.5×10⁶ cells/mL to about 10×10⁶ cells/mL, about 6.5×10⁶ cells/mL to about 9.5×10⁶ cells/mL, about 6.5×10⁶ cells/mL to about 9.0×10⁶ cells/mL, about 6.5×10⁶ cells/mL to about 8.5×10⁶ cells/mL, about 6.5×10⁶ cells/mL to about 8.0×10⁶ cells/mL, about 6.5×10⁶ cells/mL to about 7.5×10⁶ cells/mL, about 6.5×10⁶ cells/mL to about 7.0×10⁶ cells/mL, about 7.0×10⁶ cells/mL to about 10×10⁶ cells/mL, about 7.0×10⁶ cells/mL to about 9.5×10⁶ cells/mL, about 7.0×10⁶ cells/mL to about 9.0×10⁶ cells/mL, about 7.0×10⁶ cells/mL to about 8.5×10⁶ cells/mL, about 7.0×10⁶ cells/mL to about 8.0×10⁶ cells/mL, about 7.0×10⁶ cells/mL to about 7.5×10⁶ cells/mL, about 7.5×10⁶ cells/mL to about 10×10⁶ cells/mL, about 7.5×10⁶ cells/mL to about 9.5×10⁶ cells/mL, about 7.5×10⁶ cells/mL to about 9.0×10⁶ cells/mL, about 7.5×10⁶ cells/mL to about 8.5×10⁶ cells/mL, about 7.5×10⁶ cells/mL to about 8.0×10⁶ cells/mL, about 8.0×10⁶ cells/mL to about 10×10⁶ cells/mL, about 8.0×10⁶ cells/mL to about 9.5×10⁶ cells/mL, about 8.0×10⁶ cells/mL to about 9.0×10⁶ cells/mL, about 8.0×10⁶ cells/mL to about 8.5×10⁶ cells/mL, about 8.5×10⁶ cells/mL to about 10×10⁶ cells/mL, about 8.5×10⁶ cells/mL to about 9.5×10⁶ cells/mL, about 8.5×10⁶ cells/mL to about 9.0×10⁶ cells/mL, about 9.0×10⁶ cells/mL to about 10×10⁶ cells/mL, about 9.0×10⁶ cells/mL to about 9.5×10⁶ cells/mL, or about 9.5×10⁶ cells/mL to about 10×10⁶ cells/mL).

For example, the temperature of the culture medium (e.g., any of the types of culture medium described herein) can be shifted upwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20° C.). For example, the temperature of a culture medium (e.g., any of the types of culture media described herein, such as a recombinant protein production medium) can be shifted downwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20° C.). In some embodiments, the temperature of a culture medium (e.g., any of the types of culture media described herein, such as a recombinant protein production medium) after the shifting is about 32° C. to about 35° C. (e.g., about 32° C. to about 34.5° C., about 32° C. to about 34° C., about 32° C. to about 33.5° C., about 32° C. to about 33° C., about 32.5° C. to about 35° C., about 32.5° C. to about 34.5° C., about 32.5° C. to about 34° C., about 32.5° C. to about 33.5° C., about 33° C. to about 35° C., about 33° C. to about 34.5° C., about 33° C. to about 34° C., about 33.5° C. to about 35° C., about 33.5° C. to about 34.5° C., or about 34° C. to about 35° C.).

Carbon Dioxide (CO$_2$)

The culturing step described herein can further include exposing a culture media (e.g., any of the different types of culture media described herein, such as a recombinant protein production medium) to an atmosphere containing at most or about 15% CO$_2$ (e.g., at most or about 14% CO$_2$, 12% CO$_2$, 10% CO$_2$, 8% CO$_2$, 6% CO$_2$, 5% CO$_2$, 4% CO$_2$, 3% CO$_2$, 2% CO$_2$, or at most or about 1% CO$_2$).

Dissolved Oxygen (dO$_2$)

The culturing can include maintaining in a culture medium (e.g., any of the different types of culture media described herein, such as a recombinant protein production medium) a d02 level of about 35% to about 55% (e.g., about 35% to about 52.5%, about 35% to about 50%, about 35% to about 47.5%, about 35% to about 45%, about 35% to about 42.5%, about 35% to about 40%, about 35% to about 37.5%, about 37.% to about 55%, about 37.5% to about 52.%, about 37.5% to about 50%, about 37.5% to about 47.5%, about 37.5% to about 45%, about 37.5% to about 42.5%, about 37.% to about 40%, about 40% to about 55%, about 40% to about 52.5%, about 40% to about 50%, about 40% to about 47.5%, about 40% to about 45%, about 40% to about 42.5%, about 42.5% to about 55%, about 42.5% to about 52.%, about 42.5% to about 50%, about 42.5% to about 47.5%, about 42.5% to about 45%, about 45% to about 55%, about 45% to about 52.5%, about 45% to about 50%, about 45% to about 47.5%, about 47.5% to about 55%, about 47.5% to about 52.5%, about 47.5% to about 50%, about 50% to about 55%, about 50% to about 52.5%, or about 52.5% to about 55%.

Agitation

The culturing can include agitating a cell culture (e.g., a cell culture including any of the different types of cell culture media described herein, such as a recombinant protein production medium). In some examples of culturing, the agitating is performed at a frequency of about 30 RPM to about 500 RPM (e.g., about 30 RPM to: about 480 RPM, about 460 RPM, about 440 RPM, about 420 RPM, about 400 RPM, about 380 RPM, about 360 RPM, about 340 RPM, about 320 RPM, about 300 RPM, about 280 RPM, about 260 RPM, about 240 RPM, about 220 RPM, about 200 RPM, about 180 RPM, about 160 RPM, about 140 RPM, about 120 RPM, about 100 RPM, about 80 RPM, or about 60 RPM; about 40 RPM to: about 500 RPM, about 480 RPM, about 460 RPM, about 440 RPM, about 420 RPM, about 400 RPM, about 380 RPM, about 360 RPM, about 340 RPM, about 320 RPM, about 300 RPM, about 280 RPM, about 260 RPM, about 240 RPM, about 220 RPM, about 200 RPM, about 180 RPM, about 160 RPM, about 140 RPM, about 120 RPM, about 100 RPM, about 80 RPM, or about 60 RPM; about 60 RPM to: about 500 RPM, about 480 RPM, about 460 RPM, about 440 RPM, about 420 RPM, about 400 RPM, about 380 RPM, about 360 RPM, about 340 RPM, about 320 RPM, about 300 RPM, about 280 RPM, about 260 RPM, about 240 RPM, about 220 RPM, about 200 RPM, about 180 RPM, about 160 RPM, about 140 RPM, about 120 RPM, about 100 RPM, or about 80 RPM; about 80 RPM to: about 500 RPM, about 480 RPM, about 460 RPM, about 440 RPM, about 420 RPM, about 400 RPM, about 380 RPM, about 360 RPM, about 340 RPM, about 320 RPM, about 300 RPM, about 280 RPM, about 260 RPM, about 240 PRM, about 220 RPM, about 200 RPM, about 180 RPM, about 160 RPM, about 140 RPM, about 120 RPM, or about 100 RPM; about 100 RPM to: about 500 RPM, about 480 RPM, about 460 RPM, about 440 RPM, about 420 RPM, about 400 RPM, about 380 RPM, about 360 RPM, about 340 RPM, about 320 RPM, about 300 RPM, about 280 RPM, about 260 RPM, about 240 RPM, about 220 RPM, about 200 RPM, about 180 RPM, about 160 RPM, about 140 RPM, or about 120 RPM; about 120 RPM to: about 500 RPM, about 480 RPM, about 460 RPM, about 440 RPM, about 420 RPM, about 400 RPM, about 380 RPM, about 360 RPM, about 340 RPM, about 320 RPM, about 300 RPM, about 280 RPM, about 260 RPM, about 240 RPM, about 220 RPM, about 200 RPM, about 180 RPM, about 160 RPM, or about 140 RPM; about 140 RPM to: about 500 RPM, about 480 RPM, about 460 RPM, about 440 RPM, about 420 RPM, about 400 RPM, about 380 RPM, about 360 RPM, about 340 RPM, about 320 RPM, about 300 RPM, about 280 RPM, about 260 RPM, about 240 RPM, about 220 RPM, about 200 RPM, about 180 RPM, or about 160 RPM; about 160 RPM to: about 500 RPM, about 480 RPM, about 460 RPM, about 440 RPM, about 420 RPM, about 400 RPM, about 380 RPM, about 360 RPM, about 340 RPM, about 320 RPM, about 300 RPM, about 280 RPM, about 260 RPM, about 240 RPM, about 220 RPM, about 200 RPM, or about 180 RPM; about 180 RPM to: about 500 RPM, about 480 RPM, about 460 PRM, about 440 RPM, about 420 RPM, about 400 RPM, about 380 RPM, about 360 RPM, about 340 RPM, about 320 RPM, about 300 RPM, about 280 RPM, about 260 RPM, about 240 RPM, about 220 RPM, or about 200 RPM; about 200 RPM to: about 500 RPM, about 480 RPM, about 460 PRM, about 440 RPM, about 420 RPM, about 400 RPM, about 380 RPM, about 360 RPM, about 340 RPM, about 320 RPM, about 300 RPM, about 280 RPM, about 260 RPM, about 240 RPM, or about 220 RPM; about 220 RPM to: about 500 RPM, about 480 RPM, about 460 PRM, about 440 RPM, about 420 RPM, about 400 RPM, about 380 RPM, about 360 RPM, about 340 RPM, about 320 RPM, about 300 RPM, about 280 RPM, about 260 RPM, or about 240 RPM; about 240 RPM to: about 500 RPM, about 480 RPM, about 460 PRM, about 440 RPM, about 420 RPM, about 400 RPM, about 380 RPM, about 360 RPM, about 340 RPM, about 320 RPM, about 300 RPM, about 280 RPM, or about 260 RPM; about 260 RPM to: about 500 RPM, about 480 RPM, about 460 PRM, about 440 RPM, about 420 RPM, about 400 RPM, about 380 RPM, about 360 RPM, about 340 RPM, about 320 RPM, about 300 RPM, or about 280 RPM; about 280 RPM to: about 500 RPM, about 480 RPM, about 460 PRM, about 440 RPM, about 420 RPM, about 400 RPM, about 380 RPM, about 360 RPM, about 340 RPM, about 320 RPM, or about 300 RPM; about 300 RPM to: about 500 RPM, about 480 RPM, about 460 PRM, about 440 RPM, about 420 RPM, about 400 RPM, about 380 RPM, about 360 RPM, about 340 RPM, or about 320 RPM; about 320 RPM to: about 500 RPM, about 480 RPM, about 460

PRM, about 440 RPM, about 420 RPM, about 400 RPM, about 380 RPM, about 360 RPM, or about 340 RPM; about 340 RPM to: about 500 RPM, about 480 RPM, about 460 PRM, about 440 RPM, about 420 RPM, about 400 RPM, about 380 RPM, or about 360 RPM; about 360 RPM to: about 500 RPM, about 480 RPM, about 460 PRM, about 440 RPM, about 420 RPM, about 400 RPM, or about 380 RPM; about 380 RPM to: about 500 RPM, about 480 RPM, about 460 PRM, about 440 RPM, about 420 RPM, or about 400 RPM; about 400 RPM to: about 500 RPM, about 480 RPM, about 460 PRM, about 440 RPM, or about 420 RPM; about 420 RPM to: about 500 RPM, about 480 RPM, about 460 PRM, or about 440 RPM; about 440 RPM to: about 500 RPM, about 480 RPM, or about 460 RPM; about 460 RPM to: about 500 RPM, or about 480 RPM; or about 480 RPM to about 500 RPM.

Humidity

In some examples, the culturing is performed in a controlled humidified atmosphere (e.g., at a humidity of greater than 20%, 30%, 40%, 50%, 60%, 70%, 75%, 80%, 85%, 90%, or 95%, or a humidity of 100%).

Harvesting

A secreted, soluble recombinant protein can be harvested from the cell culture production medium, the second cell culture, or the recombinant protein production medium by removing or otherwise physically separating the cell culture production medium, the second culture medium, or the recombinant protein production medium from the cells (e.g., mammalian cells). A variety of different methods for removing cell culture production medium, the second culture medium, or the recombinant protein production medium from cells (e.g., recombinant mammalian cells) are known in the art, including, for example, centrifugation, filtration, pipetting, and/or aspiration.

A recombinant protein that is not secreted can be harvested, in part, by enriching the recombinant mammalian cells from the cell culture production medium, the second culture medium, or the recombinant protein production medium and lysing the enriched recombinant mammalian cells. Methods for enriching recombinant mammalian cells are known in the art, e.g., centrifugation. Methods for lysing recombinant mammalian cells are also known in the art, e.g., lysis with detergent, sonication, freeze/thaw, mortar and pestle, and mechanical disruption.

Purifying Recombinant Protein

Some embodiments of these methods further include purifying the recombinant protein. In some examples, purifying the recombinant protein can include the performance of one or more (e.g., two, three, four, five, six, or seven) unit operations. Non-limiting examples of unit operations include filtration, capturing, virus inactivation, purification, and polishing. In some examples, the recombinant protein can be purified by the performance of a single capture step using a protein A chromatography resin.

The recombinant proteins produced by the methods described herein can have a similar glycosylation or activity profile as compared to the same antibody produced in a similar cell cultured in the presence of greater than 1 g/L, 2 g/L, 3 g/L, or 4 g/L added glucose. Methods for determining the N-glycosylation pattern of a recombinant protein (e.g., a recombinant antibody) are known in the art.

Filtering

The unit operations of filtering a fluid containing the recombinant protein can be performed using a filter, or a chromatography column or chromatographic membrane that contains a molecule sieve resin. As is known in the art, a wide variety of submicron filters (e.g., a filter with a pore size of less than 1 μm, less than 0.5 μm, less than 0.3 μm, about 0.2 μm, less than 0.2 μm, less than 100 nm, less than 80 nm, less than 60 nm, less than 40 nm, less than 20 nm, or less than 10 nm) are available in the art that are capable of removing any precipitated material and/or cells. Filters having a pore size of about 0.2 μm or less than 0.2 μm are known to effectively remove bacteria from a fluid containing the recombinant protein.

Capturing

The unit operation of capturing a recombinant protein from a fluid can be performed using a chromatography column or chromatography resin, e.g., that utilizes a capture mechanism. Non-limiting examples of capturing mechanisms include a protein A-binding capture mechanism, an antibody- or antibody fragment-binding capture mechanism, a substrate-binding capture mechanism, an aptamer-binding capture mechanism, a tag-binding capture mechanism (e.g., poly-His tag-based capture mechanism), and a cofactor-binding capture mechanism. For example, if the recombinant protein is an antibody or an antibody fragment, the capturing system can be a protein A-binding capturing mechanism or an antigen-binding capturing mechanism (where the capturing antigen is specifically recognized by the recombinant antibody or antibody fragment). If the recombinant protein is an enzyme, the capturing mechanism can use an antibody or antibody fragment that specifically binds to the enzyme to capture the recombinant enzyme, a substrate of the enzyme to capture the recombinant enzyme, a cofactor of the enzyme to capture the recombinant enzyme, or, if the recombinant enzyme contains a tag, a protein, metal chelate, or antibody (or antibody fragment) that specifically binds to the tag present in the recombinant enzyme. Non-limiting resins that can be used to capture a recombinant protein are described herein and additional resins that can be used to capture a recombinant protein are known in the art. One non-limiting example of resin that utilizes a protein A-binding capture mechanism is Mab Select SuRe resin (GE Healthcare, Piscataway, N.J.). Capturing can also be performed using a resin that can be used to perform cation exchange or anion exchange chromatography, or molecular sieve chromatography. Resins that can be used to capture a recombinant protein are known in the art. In order to capture the recombinant protein using the chromatography column or chromatographic membrane, one typically performs the sequential chromatographic steps of loading, washing, eluting, and regenerating the chromatography column or chromatography membrane. As one of skill in the art can appreciate, the flow rates and buffers to be used loading, washing, eluting, and regenerating steps are chosen based on the chemical properties of the recombinant protein (e.g., pKa).

Virus Inactivation

The unit operation of inactivating viruses present in a fluid containing the recombinant protein can be performed a chromatography column, a chromatography membrane, or a holding tank that is capable of holding a fluid containing the recombinant protein at a pH of between about 3.0 to 5.0 (e.g., between about 3.5 to about 4.5, between about 3.5 to about 4.25, between about 3.5 to about 4.0, between about 3.5 to about 3.8, or about 3.75) for a period of at least 30 minutes (e.g., a period of between about 30 minutes to 1.5 hours, a period of between about 30 minutes to 1.25 hours, a period of between about 0.75 hours to 1.25 hours, or a period of about 1 hour). A holding tank can be used to perform the unit operation of virus inactivation. In another example, UV irradiation of a fluid containing recombinant protein can be used to perform the unit operation of inactivating viruses. As can be appreciated by those skilled in the art, a variety of other means can be used to perform the unit operation of virus inactivation.

Purifying

The unit operation of purifying a recombinant protein can be performed using a chromatography column or chromatographic membrane that contains a resin, e.g., that utilizes a capture system. Non-limiting examples of capturing mechanisms include a protein A-binding capture mechanism, an antibody- or antibody fragment-binding capture mechanism, a substrate-binding capture mechanism, an aptamer-binding capture mechanism, a tag-binding capture mechanism (e.g., poly-His tag-based capture mechanism), and a cofactor-binding capture mechanism. Purifying can also be performed using a resin that can be used to perform cation exchange or anion exchange chromatography, or molecular sieve chromatography. Resins that can be used to purify a recombinant protein are known in the art.

As can be appreciated by one skilled in the art, the step of purifying a recombinant protein can, e.g., include the steps of loading, washing, eluting, and equilibrating the at least one chromatography column or chromatographic membrane used to perform the unit of operation of purifying the recombinant protein. Typically, the elution buffer coming out of a chromatography column or chromatographic membrane used to perform the unit operation of purifying contains the recombinant protein.

Following the loading of the recombinant protein onto the chromatographic column or chromatographic membrane that is used to perform the unit operation of purifying the recombinant protein, the chromatographic column or chromatographic membrane is washed with at least one washing buffer. As can be appreciated in the art, the washing buffer is meant to elute all proteins that are not the recombinant protein from the chromatography column or chromatographic membrane, while not disturbing the interaction of the recombinant protein with the resin or otherwise eluting the recombinant protein.

Non-limiting examples of elution buffers that can be used in these methods will depend on the resin and/or the recombinant protein. For example, an elution buffer can contain a different concentration of salt (e.g., increased salt concentration), a different pH (e.g., an increased or decreased pH), or a molecule that will compete with the recombinant protein for binding to the resin. Examples of such elution buffers for each of the exemplary capture mechanisms are known in the art.

Following the elution of the recombinant protein from the chromatographic column or chromatographic membrane that can be used to perform the unit operation of purifying the recombinant protein, the chromatography column or chromatographic membrane can be equilibrated using a regeneration buffer.

Polishing

The unit operation of polishing a recombinant protein can be performed using a chromatography column or chromatographic membrane that contains a resin, e.g., that can be used to perform cation exchange, anion exchange, or molecular sieve chromatography. Examples of resins that can be used to polish a recombinant protein are known in the art.

As can be appreciated in the art, polishing a recombinant protein using the chromatography column or chromatography membrane that can be used to perform the unit operation of polishing the recombinant protein can include, e.g., the steps of loading, chasing, and regenerating the chromatography column or chromatographic membrane that can be used to perform the unit operation of polishing the recombinant protein. For example, when the steps of loading, chasing, and regenerating are used to perform the polishing, the recombinant protein does not bind the resin in the chromatography column or chromatography membrane that is used to perform the unit operation of polishing the recombinant protein, and the recombinant protein is eluted from the chromatography column or chromatographic membrane in the loading and chasing steps, and the regenerating step is used to remove any impurities from the chromatography column or chromatographic membrane. Examples of flow rates and buffer volumes to be used in each of the loading, chasing, and regenerating steps are known in the art.

Pharmaceutical Compositions

Also provided herein are pharmaceutical compositions that include at least one (e.g., one, two, three, or four) of the recombinant proteins produced using any of the methods provided herein. Two or more (e.g., two, three, or four) of any of the recombinant proteins provided herein can be present in a pharmaceutical composition in any combination. The pharmaceutical compositions may be formulated in any manner known in the art.

Pharmaceutical compositions are formulated to be compatible with their intended route of administration (e.g., intravenous, intraarterial, intramuscular, intradermal, subcutaneous, intraperitoneal, or oral). The compositions can include a sterile diluent (e.g., sterile water or saline), a fixed oil, polyethylene glycol, glycerin, propylene glycol, or other synthetic solvents, antibacterial or antifungal agents, such as benzyl alcohol or methyl parabens, chlorobutanol, phenol, ascorbic acid, thimerosal, and the like, antioxidants, such as ascorbic acid or sodium bisulfate, chelating agents, such as ethylenediaminetetraacetic acid, buffers, such as acetates, citrates, or phosphates, and isotonic agents, such as sugars, polyalcohols (e.g., mannitol or sorbitol), or salts (e.g., sodium chloride), or any combination thereof. Liposomal suspensions can also be used as pharmaceutically acceptable carriers (see, e.g., U.S. Pat. No. 4,522,811). Preparations of the compositions can be formulated and enclosed in ampules, disposable syringes, or multiple dose vials. Where required (as in, for example, injectable formulations), proper fluidity can be maintained by, for example, the use of a coating, such as lecithin, or a surfactant. Absorption of the recombinant protein can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

Compositions that include one or more of any of the recombinant proteins can be formulated for parenteral (e.g., intravenous, intraarterial, intramuscular, intradermal, subcutaneous, or intraperitoneal) administration in dosage unit form (i.e., physically discrete units containing a predetermined quantity of active protein for ease of administration and uniformity of dosage).

Toxicity and therapeutic efficacy of the compositions can be determined by standard pharmaceutical procedures in cell cultures or experimental animals (e.g., monkeys). One can, for example, determine the LD50 (the dose lethal to 50% of the population) and the ED50 (the dose therapeutically effective in 50% of the population): the therapeutic index being the ratio of LD50:ED50. Compositions that exhibit high therapeutic indices are preferred. Where a composition exhibits an undesirable side effect, care should be taken to minimize potential damage (i.e., reduce unwanted side effects). Toxicity and therapeutic efficacy can be determined by other standard pharmaceutical procedures.

Data obtained from cell culture assays and animal studies can be used in formulating an appropriate dosage of any given recombinant protein (e.g., any of the recombinant proteins described herein) for use in a subject (e.g., a human). A therapeutically effective amount of the one or more (e.g., one, two, three, or four) recombinant proteins (e.g., any of the recombinant proteins described herein) will be an amount that treats a target disease in a subject (e.g., decreases the risk of developing or prevents the development of the target disease in a subject (e.g., a human subject identified as having an increased risk of developing the target disease)), decreases the severity, frequency, and/or duration of one or more symptoms of the target disease in a subject (e.g., a human) (e.g., as compared to a control subject having the same target disease but, e.g., not receiving treatment, receiving a different treatment, or receiving a placebo, or the same subject prior to treatment). The effectiveness and dosing of any of the recombinant proteins described herein can be determined by a health care professional or veterinary professional using methods known in the art, as well as by the observation of one or more symptoms of the target disease in a subject (e.g., a human). Certain factors may influence the dosage and timing required to effectively treat a subject (e.g., the severity of the disease or disorder, previous treatments, the general health and/or age of the subject, and the presence of other diseases).

Any of the pharmaceutical compositions described herein can further include one or more (e.g., two, three, four, or five) additional therapeutic agents.

Exemplary doses include milligram or microgram amounts of any of the recombinant proteins described herein per kilogram of the subject's weight (e.g., about 50 µg/kg to about 3 mg/kg; about 100 µg/kg to about 2.5 mg/kg; about 100 µg/kg to about 2.0 mg/kg; about 500 µg/kg to about 1.5 mg/kg; about 500 µg/kg to about 1.5 mg/kg; or about 800 µg/kg to about 1.2 mg/kg). Exemplary doses may also include milligram or microgram amounts of one or more additional therapeutic agents per kilogram of the subject's weight (e.g., about 1 µg/kg to about 500 mg/kg; about 100 µg/kg to about 500 mg/kg; about 100 µg/kg to about 50 mg/kg; about 10 µg/kg to about 5 mg/kg; about 10 µg/kg to about 0.5 mg/kg; or about 1 µg/kg to about 50 µg/kg for each administered additional therapeutic agent). While these doses cover a broad range, one of ordinary skill in the art will understand that therapeutic agents, including recombinant proteins and the additional one or more therapeutic agents, vary in their potency, and effective amounts can be determined by methods known in the art. Typically, relatively low doses are administered at first, and the attending healthcare professional or veterinary professional (in the case of therapeutic application) or a researcher (when still working at the development stage) can subsequently and gradually increase the dose until an appropriate response is obtained. In addition, it is understood that the specific dose level for any particular subject will depend upon a variety of factors including the activity of the specific protein employed, the age, body weight, general health, gender, and diet of the subject, the time of administration, the route of administration, the rate of excretion, and the half-life of the recombinant protein or the additional therapeutic agents in vivo. The pharmaceutical compositions can be included in a container, pack, or dispenser together with instructions for administration.

For example, one or more recombinant proteins provided herein can be packaged in a sterile vial as a lyophilized powder or cake, for later reconstitution and administration. The lyophilized powder or cake that includes recombinant protein can include one or more stabilizing agents (e.g., one or more of mannitol, sodium phosphate monobasic monohydrate, and sodium phosphate dibasic heptahydrate). Before use or administration of the recombinant protein, the lyophilized powder or cake is reconstituted by injection of a pharmaceutically acceptable carrier or vehicle (e.g., sterile water for injection, USP), into the vial, to yield a solution of the recombinant protein. This reconstituted solution can further be diluted with a pharmaceutically acceptable carrier or solution (e.g., the same or a different pharmaceutically acceptable carrier or solution), prior to intravenous administration to the subject.

Kits

Also provided herein are kits that include at least one dose of any of the pharmaceutical compositions described herein. In some embodiments, the kits can further include an item for use in administering a pharmaceutical composition (e.g., any of the pharmaceutical compositions described herein) to the mammal (e.g., human) (e.g., a syringe, e.g., a pre-filled syringe). Some examples of the kits include one or more doses (e.g., at least two, three, four, five, six, seven, eight, nine, ten, eleven, twelve, thirteen, fourteen, twenty, thirty, or forty doses) (e.g., intravenous, subcutaneous, or intraperitoneal doses) of any of the pharmaceutical compositions described herein. In some examples, the kit further includes instructions for administering the pharmaceutical composition (or a dose of the pharmaceutical composition) to a mammal (e.g., a human having a target disease or a human in need thereof).

Also included are kits that include a vial of a lyophilized recombinant protein cake or powder, instructions for reconstituting the cake or powder (as described in this paragraph), and instructions for intravenous administration of the reconstituted solution to a subject (e.g., a subject having a target disease or a human in need thereof).

In some embodiments, the kits include a composition including at least one of the recombinant proteins described herein, and a composition containing at least one additional therapeutic agent. In some embodiments, the kit further contains instructions for administering the composition including at least one of the recombinant proteins described herein and a composition containing at least one additional therapeutic agent to a subject (e.g., a subject having a target disease or a human in need thereof).

EXAMPLES

Example 1. N-Glycosylation of Recombinant Adalimumab Produced by Culturing Cells in Mannose, Maltose, and Fructose A variety of cell culture runs were performed using culture media and feeds formulated to exclude glucose and different combinations of one or more alternative energy source(s), and the N-glycosylation profile of the recombinant adalimumab produced in each cell culture run was determined. Adalimumab produced by the culturing methods described below and adalimumab isolated from Humira® (AbbVie, Inc.) were analyzed for N-glycosylation by N-glycanase treatment (PNGase F) to release the N-linked glycans, and subsequent labeling of the released glycans with a 2-aminobenzamide (2-AB) fluorescent probe.

The resultant 2-AB labeled glycans were separated on an amide HILIC column with fluorescence detection.

Example 2

CHO cells are capable of growing in cell culture base media that is well known in the art including cell culture media free of any animal-derived serum. For optimal expression of particular biologics such as recombinant proteins including antibodies and fragments thereof, these media must be supplemented with additional components. The following examples describe methods and compositions of the present invention for culturing CHO cells expressing adalimumab. In the following examples the growth phase refers to the phase of culturing the cells where the purpose is exponential cell growth or replication, whereas the production phase refers to the phase of culturing the cells where the purpose is protein production.

Example A. Production of Adalimumab Using Both a Perfusion and a Fed-Batch Method A. Growth Phase using Perfusion Method A perfusion bioreactor is inoculated at a concentration from about 0.1 to about 5 million cells/mL and cells are allowed to grow in perfusion mode to a density from about 1 to about 50 million cells/mL using a cell culture growth medium. The growth medium contains a glucose concentration ranging from about 0.1 g/L to about 20 g/L and is supplemented with at least one other hexose such as galactose, mannose, fructose or combination thereof, each at concentration from about 0.1 to about 20 g/L.

B. Production Phase Using Fed-Batch Method

A fed-batch bioreactor is inoculated with cells from the growth phase at a concentration from about 3 million to about 20 million cells/mL in a cell culture production medium containing glucose at concentration from about 0.1 to about 0.9 g/L and at least one other hexose such as galactose, mannose, fructose or combination thereof, each at concentration from about 0.1 g/L to about 20 g/L. The glucose concentration is maintained from about 0.1 to about 0.9 g/L throughout the entire culture duration. Galactose, mannose and fructose can be additionally supplemented, maintaining each at concentration from about 0.1 to about 20 g/L. The fed-batch culture may be supplemented with other feeds such as concentrated medium and other feeds which are devoid of glucose. The culture is terminated and is harvested for adalimumab at a cell viability from about 20% to about 100%, most preferably from about 50% to about 80%.

Example B. Production of Adalimumab Using a Fed-Batch Method

A. Growth Phase Using a Fed-Batch Method

A fed-batch bioreactor is inoculated at 0.1 to 2 million cells/mL and cells are allowed to grow in fed-batch mode using a cell culture growth medium. The growth medium contains a glucose concentration ranging from about 0.1 g/L to about 0.9 g/L and is supplemented with at least one other hexose such as galactose, mannose, fructose or combination thereof, each at concentration from about 0.1 g/L to about 20 g/L.

B. Production Phase Using a Fed-Batch Method

The cell culture from the growth phase is maintained at a glucose concentration from about 0.1 g/L to about 0.9 g/L throughout the entire culture duration. Galactose, mannose and fructose can be additionally supplemented, maintaining each at concentration from about 0.1 to about 20 g/L. The fed-batch culture may be supplemented with other feeds such as concentrated medium and other feeds which are devoid of glucose. The culture is terminated and is harvested for adalimumab at a cell viability from about 20% to about 100%, most preferably from about 50% to about 80%.

Example C. Production of Adalimumab Using a Repeated Fed-Batch Method

A. Cycle 1-Growth/Production Phase Using a Fed-Batch Method

A fed-batch bioreactor is inoculated at 0.1 to 2 million cells/mL and cells are allowed to grow in fed-batch mode using a cell culture growth medium. The growth medium contains a glucose concentration ranging from about 0.1 g/L to about 0.9 g/L and is supplemented with at least one other hexose such as galactose, mannose, fructose or combination thereof, each at concentration from about 0.1 g/L to about 20 g/L. The glucose concentration is maintained from about 0.1 to about 0.9 g/L throughout the entire culture duration. Galactose, mannose and fructose can be additionally supplemented, maintaining each at concentration from about 0.1 to about 20 g/L. The fed-batch culture may be supplemented with other feeds such as concentrated medium and other feeds which are devoid of glucose. 90% of the cell culture is harvested for adalimumab at a cell viability from about 80% to about 100%.

B. A. Cycle 2-Growth/Production Phase Using a Fed-Batch Method

Growth/Production medium is removed from the fed-batch bioreactor containing the remaining 10% of the cell culture. Fresh production medium is added to the fed-batch bioreactor. The fresh production medium contains a glucose concentration ranging from about 0.1 g/L to about 0.9 g/L and is supplemented with at least one other hexose such as galactose, mannose, fructose or combination thereof, each at concentration from about 0.1 g/L to about 20 g/L. The glucose concentration is maintained from about 0.1 to about 0.9 g/L throughout the entire culture duration. Galactose, mannose and fructose can be additionally supplemented, maintaining each at concentration from about 0.1 to about 20 g/L. The fed-batch culture may be supplemented with other feeds such as concentrated medium and other feeds which are devoid of glucose. 90% of the cell culture is harvested for adalimumab at a cell viability from about 80% to about 100%. Cycle 1 and 2 can be repeated for additional adalimumab production.

Example D. Production of Adalimumab Using a Continuous Perfusion Method

A. Growth Phase

A perfusion bioreactor is inoculated at a concentration from about 0.1 to about 5 million cells/mL and cells are allowed to grow in perfusion mode to a density from about 1 to about 50 million cells/mL using a cell culture growth medium. The growth medium contains a glucose concentration ranging from about 0.1 to about 10 g/L and is supplemented with at least one other hexose such as galactose, mannose, fructose or combination thereof, each at concentration from about 0.1 to about 20 g/L.

B. Production Phase

The cell culture is perfused with production medium with a glucose concentration ranging from about 0.1 g/L to about 0.9 g/L and which is supplemented with at least one other hexose such as galactose, mannose, fructose or combination thereof, each at concentration from about 0.1 g/L to about 20 g/L. After incubation in the production medium, the perfusate containing the adalimumab is harvested periodically.

General Culturing Methods for Examples 3-12

A recombinant CHO DG44 cell line containing nucleic acid encoding the light chain and the heavy chain of adalimumab were used in all the experimental runs described in Examples 3-12.

The recombinant cells used to seed each experiment were from a seed train that used a glucose free formulation of CD-C4 medium supplemented with 50 µg/L IGF LongR, 6 mM L-glutamine, and 6 g/L glucose up to the N−1 culturing step, and used a glucose free formulation of CD-C4 medium supplemented with 50 µg/L IGF LongR, 6 mM L-glutamine, and 6 g/L mannose for the N−1 culturing step. The seed train culturing was performed at 37° C.

For Examples 3-12, the recombinant cells from the seed train culture were used to inoculate the bioreactors.

Example 3. Experiment #1

Fifty (50) mLs of glucose-free BalanCD® Growth A medium (Irvine Scientific, cat #99850; BalanCD is a registered trademark of Irvine Scientific Sales Co., Inc.), supplemented with 8 mM L-glutamine, 0.7 g/L glucose and 1.8 g/L mannose, was inoculated in order to achieve an initial viable cell density of $5.0 \times 10^5$ cells/mL (SF1), $2.0 \times 10^6$ cells/mL (SF3) and $5.0 \times 10^6$ cells/mL (SF7). Cultures were fed with Feed1 (Irvine Scientific, glucose-free formulation of product Catalog No. 91127) on Day 0 (10% of the original culture volume), Day 3 (2.5% of the original culture volume) and Day 6 (2.5% original culture volume). The glucose level was maintained at 0.7 g/L and the L-glutamine level was maintained at 8 mM.

The temperature was maintained at 37° C. until the end of the experimental run. Cultivation took place in an incubator with a controlled humidity of 85% and a $CO_2$ level of 5%. The culture was agitated at a rate of 125 RPM.

Harvest was performed when the culture viability declined to between 60% and 70%. Samples were stored frozen until N-glycan analysis was performed.

Figure 2:
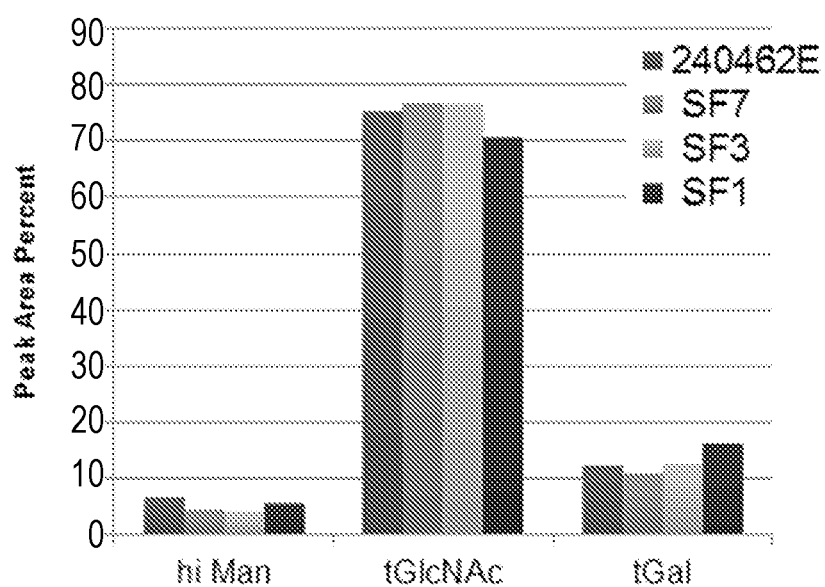

The results of the analysis are shown below in Table 1, and graphically in FIGS. 1 and 2.

TABLE 1

| | % Fucosylated | % Afucosylation | Tgal | TGlcNac | High Man |
|---|---|---|---|---|---|
| SF7 | 83.8 | 8.4 | 11 | 76.6 | 4.6 |
| SF3 | 85.1 | 8.5 | 12.8 | 76.8 | 4.1 |
| SF1 | 80.5 | 12.4 | 16.4 | 70.8 | 5.8 |
| Humira ® Lot 240462E | 84.4 | 9.8 | 12.3 | 75.4 | 6.5 |

Example 4. Experiment #2

Fifty (50) mLs of glucose-free BalanCD® Growth A medium (Irvine Scientific, cat #99850), supplemented with 8 mM L-glutamine, 0.7 g/L glucose and 1.8 g/L mannose, was inoculated in order to achieve an initial viable cell density of $2.0 \times 10^6$ cells/mL (SF3), $1.0 \times 10^6$ cells/mL (SF5) and $0.5 \times 10^6$ cells/mL (SF7). Cultures were fed with Feed1 (Irvine Scientific, glucose-free formulation of product Catalog No. 91127) on Day 0 (15% of the original culture volume). Glucose level was maintained at 0.7 g/L, and L-glutamine level was maintained at 8 mM.

The temperature was maintained at 37° C. until the end of the experimental run. Cultivation took place in an incubator with a controlled humidity of 85% and a $CO_2$ level of 5%. The culture was agitated at a rate of 125 RPM.

Harvest was performed when the viability of the culture declined to between 60% and 70%. Samples were stored frozen until N-glycan analysis was performed.

Figure 3:
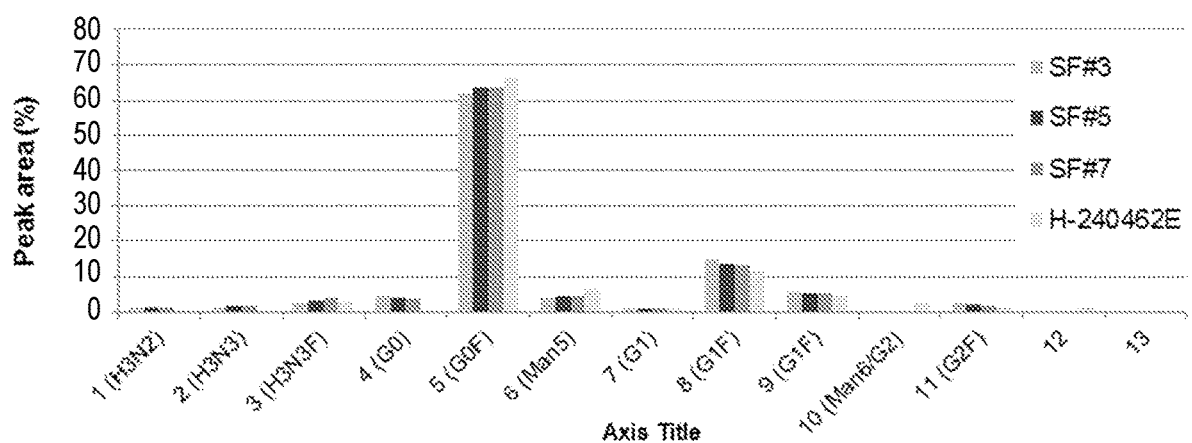
FIG. 3 is a graph showing the glycoprofile of adalimumab samples produced using the low-glucose production method of Example 4, Experiment #2 as compared to Humira® Lot #240462E.
Figure 4:
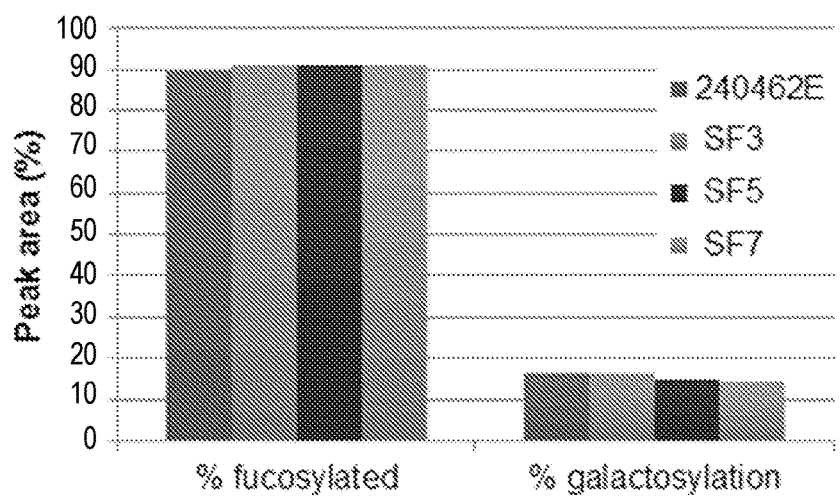
FIGS. 4 and 5 shows the major groups of glycoforms of adalimumab samples from the low glucose production method of Example 4, Experiment #2 compared to Humira® Lot #240462E.
Figure 5:
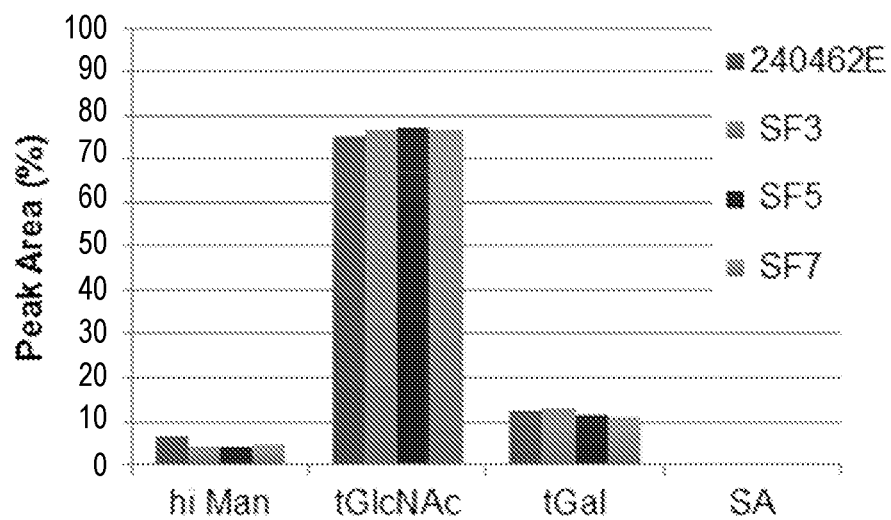
Figure 6:
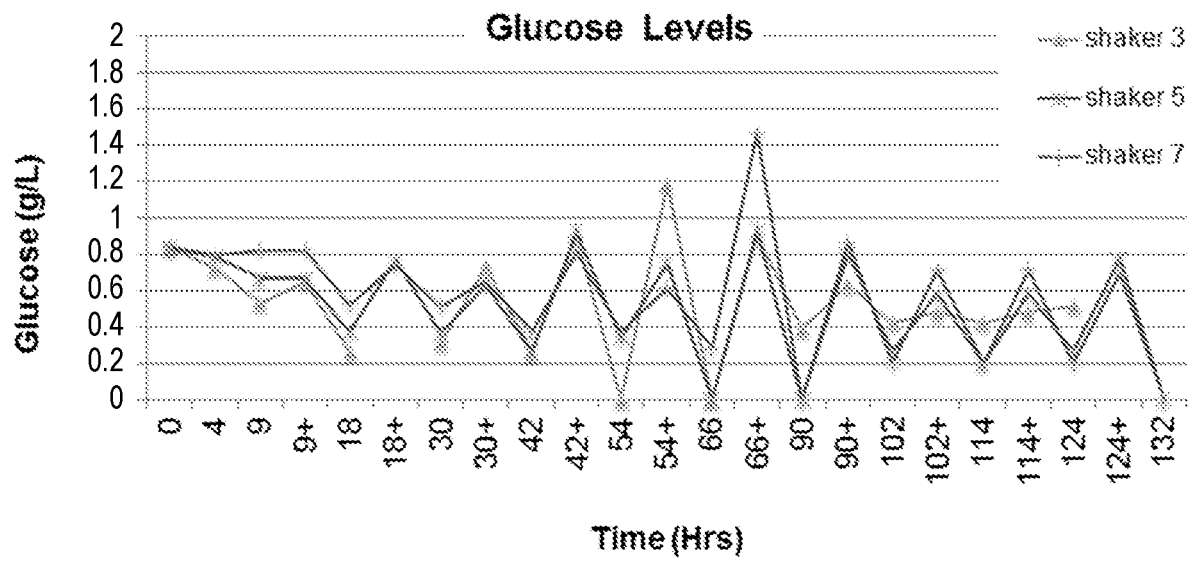
FIG. 6 shows the maintenance of the glucose level at a target concentration of 0.7 g/L (measurements taken before after glucose supplementation) in Example 4, Experiment #2.

The results of the analysis are shown below in Table 2, and graphically in FIGS. 4 and 5 which shows the major groups of glycoforms. In addition, FIG. 3 shows the glycoprofile of adalimumab samples produced from the low glucose process compared to Humira® Lot #240462E, while FIG. 6 shows the maintenance of the glucose level at a target concentration of 0.7 g/L (measurements taken before after glucose supplementation).

TABLE 2

| | Fucosylation | Afucosylation | Tgal | TGlcNac | High Man |
|---|---|---|---|---|---|
| SF3 | 85.1 | 8.5 | 12.8 | 76.8 | 4.1 |
| SF5 | 84.4 | 8.4 | 11.4 | 77 | 4.4 |
| SF7 | 83.8 | 8.4 | 11 | 76.6 | 4.6 |
| Humira ® Lot 240462E | 84.4 | 9.8 | 12.3 | 75.4 | 6.5 |

Example 5. Experiment #3

Shake Flask A-42 (SFA-42)

Fifty (50) mLs of glucose-free BalanCD® Growth A medium (Irvine Scientific, cat #99850), supplemented with 8 mM L-glutamine, 0.7 g/L glucose, 4 g/L galactose, 3.6 g/L mannose, and 8 g/L fructose, was inoculated in order to achieve an initial viable cell density of $2.0 \times 10^6$ cells/mL. Cultures were fed with Feed1 (Irvine Scientific, glucose-free formulation of product Catalog No. 91127) on Day 0 (10% of the original culture volume) and Days 2 and 3 (7.5% of the original culture volume). Glucose level was maintained at 0.7 g/L, and L-glutamine level was maintained at 8 mM.

Shake Flask A-44 (SFA-44)

Fifty (50) mLs of glucose-free BalanCD® Growth A medium (Irvine Scientific, cat #99850), supplemented with 8 mM L-glutamine, 0.7 g/L glucose, 4 g/L galactose, and 8 g/L fructose, was inoculated in order to achieve an initial viable cell density of $2.0 \times 10^6$ cells/mL. Cultures were fed with Feed1 (Irvine Scientific, glucose-free formulation of product Catalog No. 91127) on Day 0 (10% of the original culture volume) and Days 2 and 3 (7.5% of the original culture volume). Glucose level was maintained at 0.7 g/L, and L-glutamine level was maintained at 8 mM.

Shake Flask C-25 (SFC-25)

Fifty (50) mLs of glucose free BalanCD® Growth A medium (Irvine Scientific, cat #99850), supplemented with 4 mM L-glutamine, 0.7 g/L glucose, and 3.6 g/L mannose, was inoculated in order to achieve an initial viable cell density of $5.0 \times 10^6$ cells/mL. Cultures were fed with Feed1 (Irvine Scientific, glucose-free formulation of product Catalog No. 91127) on Day 0 (10% of the original culture volume) and Days 3 and 6 (2.5% of the original culture volume). Glucose level was maintained at 0.7 g/L and L-glutamine level was maintained at 4 mM.

Cultures SFA-42, SFA-44 and SF C-25 were cultivated at 37° C. for the entire duration of the experiment. Cultivation took place in an incubator with a controlled humidity of 85% and a $CO_2$ level of 5%. The culture was agitated at a rate of 125 RPM.

Harvest was performed when viability of the culture declined to between 60% and 70%. Samples were stored frozen until N-glycan analysis was performed.

Figure 7:
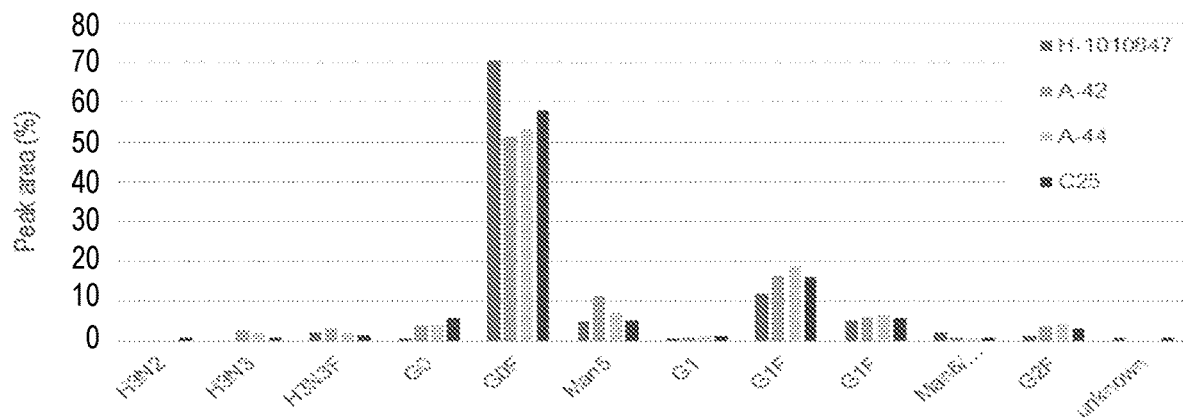
FIG. 7 is a graph showing the glycoprofile of adalimumab samples from the low glucose production method of Example 5, Experiment #3 compared to Humira® Lot #1010847.
Figure 8:
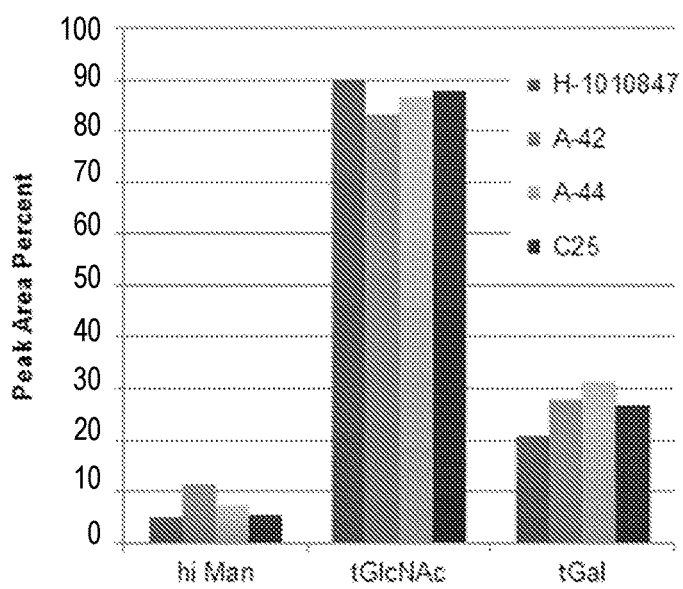
FIGS. 8 and 9 show the major groups of glycoforms of adalimumab samples from the low glucose Example 5, Experiment #3 compared to Humira® Lot #1010847.
Figure 9:
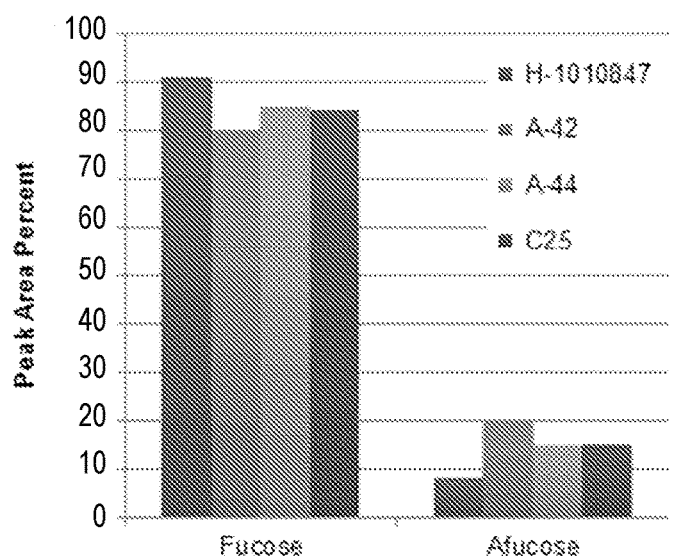

The results of the analysis are shown below in Table 3, and graphically in FIGS. 8 and 9. In addition, FIG. 7 shows the glycoprofile of adalimumab samples from the low glucose process compared to Humira® Lot #1010847.

TABLE 3

|  | Fucosylation | Afucosylation | Tgal | TGlcNac | High Man |
|---|---|---|---|---|---|
| SF A-42 | 80.2 | 19.8 | 28 | 83.1 | 11.2 |
| SF A-44 | 85 | 15 | 31.4 | 86.8 | 7.2 |
| SF C25 | 84.2 | 15 | 26.9 | 87.8 | 5.3 |
| Humira ® Lot 1010847 | 90.8 | 15 | 20.8 | 90.2 | 5 |

Example 6. Experiment #4

Shake Flask 72 (SF72)

The aim of this experiment was to test Growth Phase in the presence of glucose at a concentration below 4 g/L and Production Phase in the presence of glucose at a concentration below 1.0 g/L (the target was 0.7 g/L).

Fifty (50) mLs of glucose-free BalanCD® Growth A medium (Irvine Scientific, cat #99850), supplemented with 8 mM L-glutamine and 4.0 g/L glucose, was inoculated in order to achieve an initial viable cell density of $0.5 \times 10^6$ cells/mL. The culture was fed with Feed1 (Irvine Scientific, glucose-free formulation of product Catalog No. 91127) on Day 0 (10% of the original culture volume) and Days 3 and 6 (2.5% of the original culture volume). Glucose level was maintained between 2 g/L and 4 g/L from Day 0 (inoculation day) to Day 3. From Day 4 until the end of the experiment, glucose level was maintained at 0.7 g/L. L-glutamine was maintained at 4 mM.

Shake Flask 73 (SF73)

The aim of this experiment was to test Growth Phase in the presence of glucose at a concentration below 4 g/L and Production Phase in the presence of glucose at a concentration below 1.0 g/L (the target was 0.7 g/L).

Fifty (50) mLs of glucose-free BalanCD® Growth A medium (Irvine Scientific, cat #99850), supplemented with 8 mM L-glutamine, 3 g/L mannose and 4.0 g/L glucose, was inoculated in order to achieve an initial viable cell density of $0.5 \times 10^6$ cells/mL. The culture was fed with Feed1 (Irvine Scientific, glucose-free formulation of product Catalog No. 91127) on Day 0 (10% of the original culture volume) and Days 3 and 6 (2.5% of the original culture volume). Glucose level was maintained between 2 g/L and 4 g/L from Day 0 (inoculation day) to Day 3. From Day 4 until end of experiment, glucose level was maintained at 0.7 g/L. Mannose was supplemented daily from Day 3 until harvest at 1.0 g/L. L-glutamine was maintained at 4 mM.

Shake Flask 74 (SF74)

The aim of this experiment was to test Growth Phase in the presence of glucose at a concentration below 3 g/L (the target was 2.5 g/L) and Production Phase in the presence of glucose at a concentration below 2 g/L (target was below 1.8 g/L)

Fifty (50) mLs of glucose-free BalanCD® Growth A medium (Irvine Scientific, cat #99850), supplemented with 8 mM L-glutamine and 2.5 g/L glucose, was inoculated in order to achieve an initial viable cell density of $0.5 \times 10^6$ cells/mL (SF72). The culture was fed with Feed1 (Irvine Scientific, glucose-free formulation of product Catalog No. 91127) on Day 0 (10% of the original culture volume) and Days 3 and 6 (2.5% of the original culture volume). Glucose level was maintained at 2.5 g/L from Day 0 (inoculation day) to Day 3. From Day 4 until the end of the experiment, glucose level was maintained at 1.8 g/L. L-glutamine was allowed to be exhausted, no additional feeds were made for the entire culture duration. The culture was maintained at 34° C. from Day 0 until harvest.

Shake Flask 78 (SF78)

The aim of this experiment was to test Growth Phase in the presence of glucose at a concentration below 3 g/L (target was 2.5 g/L) and Production Phase in the presence of glucose at a concentration below 2 g/L (target was below 1.8 g/L).

Fifty (50) mLs of glucose-free BalanCD® Growth A medium (Irvine Scientific, cat #99850), supplemented with 8 mM L-glutamine, 3 g/L mannose and 2.5 g/L glucose, was inoculated in order to achieve an initial viable cell density of $0.5 \times 10^6$ cells/mL (SF72). Culture was fed with Feed1 (Irvine Scientific, glucose-free formulation of product Catalog No. 91127) on Day 0 (10% of the original culture volume) and Days 3 and 6 (2.5% of the original culture volume). Glucose level was maintained at 2.5 g/L from Day 0 (inoculation day) to Day 3. From Day 4 until the end of the experiment, glucose level was maintained at 0.7 g/L. L-glutamine was allowed to be exhausted, no additional feeds were made for the entire culture duration. The culture was maintained at 37° C. from Day 0 until harvest.

Cultivation took place in an incubator with a controlled humidity of 85% and a $CO_2$ level of 5%. The culture was agitated at a rate of 125 RPM.

Harvest was performed when the viability of the culture declined to between 60% and 70%. Samples were stored frozen until N-glycan analysis was performed.

Figure 12:
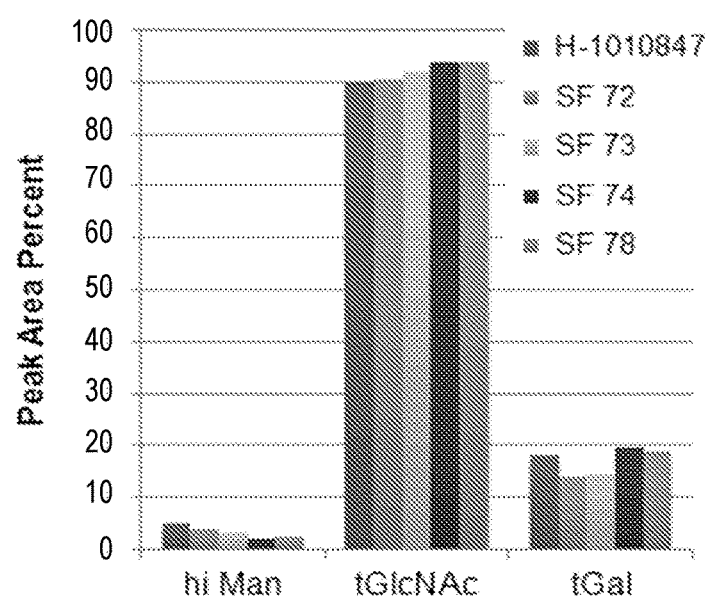
FIGS. 12 and 13 show the major groups of glycoforms of adalimumab samples from the low glucose production method of Example 6, Experiment #4 compared to Humira® Lot #1010847.
Figure 13:
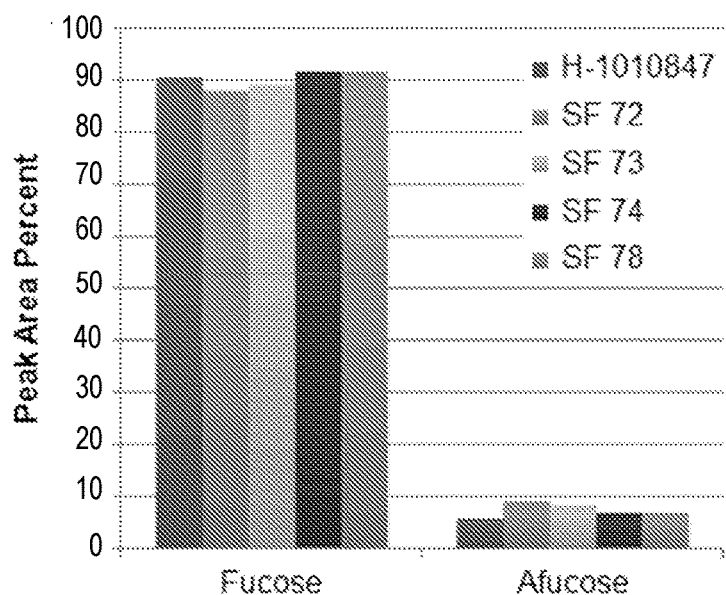

The results of the analysis are shown below in Table 4, and graphically in FIGS. 12 and 13. FIGS. 12 and 13 show the major groups of glycoforms of adalimumab samples from the low glucose production method of Example 6, Experiment #4 compared to Humira® Lot #1010847.

Figure 10:
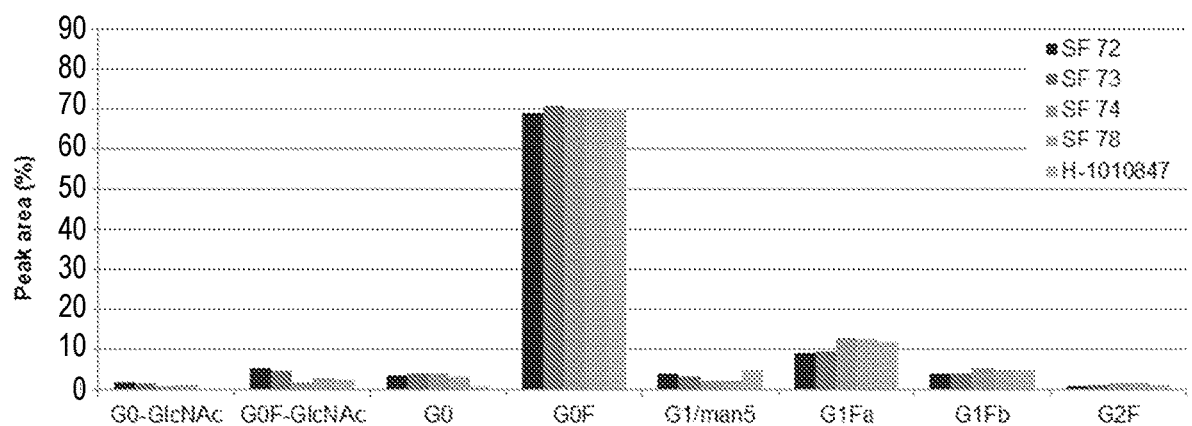
FIGS. 10 and 11 are graphs showing the glycoprofile of adalimumab samples from the low glucose production method Example 6, Experiment #4 compared to Humira® Lot #1010847.
Figure 11:
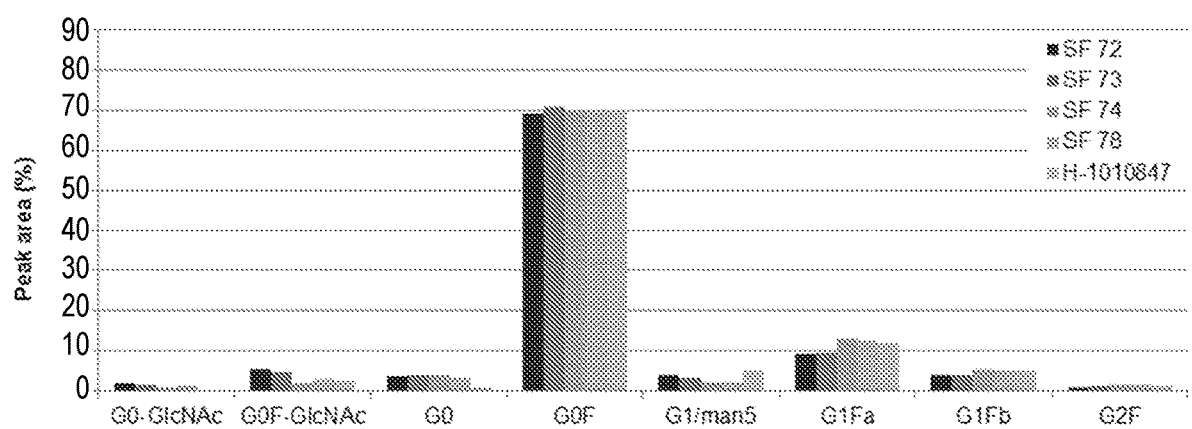

In addition, FIGS. 10 and 11 are graphs showing the glycoprofile of adalimumab samples from the low glucose production method Example 6, Experiment #4 compared to Humira® Lot #1010847.

TABLE 4

|  | Fucosylation | Afucosylation | Tgal | TGlcNac | High Man |
|---|---|---|---|---|---|
| SF 72 | 88 | 9.1 | 13.8 | 90.6 | 3.8 |
| SF 73 | 89.3 | 8.5 | 14.2 | 92 | 3.1 |
| SF 74 | 91.6 | 6.9 | 19.6 | 93.8 | 2.2 |
| SF78 | 91.9 | 6.7 | 19 | 93.8 | 3.3 |
| Humira ® Lot #1010847 | 90.5 | 5.7 | 18.1 | 90 | 5.1 |

Example 7. Experiment #5

Shake Flask A-97 (SFA-97)

Fifty (50) mLs of glucose-free BalanCD® Growth A medium (Irvine Scientific, cat #99850), supplemented with 6 mM L-glutamine and 0.7 g/L glucose, was inoculated in order to achieve an initial viable cell density of $0.5 \times 10^6$ cells/mL. The culture was fed with Feed1 (Irvine Scientific, glucose-free formulation of product Catalog No. 91127) on Day 0 (10% of the original culture volume) and Days 3, 5 and 7 (3.5% of the original culture volume). Glucose level was maintained at 0.7 g/L for the entire duration of the culture. Maltose was fed daily from Day 0 until harvest at 2 g/L. L-glutamine was allowed to be exhausted, no additional glutamine feeds were made for the entire culture duration. The culture was maintained at 35° C. from Day 0 until harvest.

Shake Flask A-98 (SFA-98)

Fifty (50) mLs of glucose-free BalanCD® Growth A medium (Irvine Scientific, cat #99850), supplemented with 6 mM L-glutamine and 0.7 g/L glucose, was inoculated in order to achieve an initial viable cell density of $0.5 \times 10^6$ cells/mL. The culture was fed with Feed1 (Irvine Scientific, glucose-free formulation of product Catalog No. 91127) on Day 0 (10% of the original culture volume) and Days 3, 5 and 7 (3.5% of the original culture volume). Glucose level was maintained at 0.7 g/L for the entire duration of the culture. Maltose was fed daily from Day 0 to Day 4 at 2 g/L, and from Day 4 until harvest at 3 g/L. L-glutamine was allowed to be exhausted, no additional glutamine feeds were made for the entire culture duration. The culture was maintained at 35° C. from Day 0 until harvest.

Shake Flask A-99 (SFA-99)

Fifty (50) mLs of glucose free BalanCD® Growth A medium (Irvine Scientific, cat #99850), supplemented with 6 mM L-glutamine and 0.7 g/L glucose, was inoculated in order to achieve an initial viable cell density of $0.5 \times 10^6$ cells/mL. The culture was fed with Feed1 (Irvine Scientific, glucose-free formulation of product Catalog No. 91127) on Day 0 (10% of the original culture volume) and Days 3, 5 and 7 (3.5% of the original culture volume). Glucose level was maintained at 0.7 g/L for the entire duration of the culture. Maltose was fed daily from Day 0 to Day 4 at 2 g/L, and from Day 4 until harvest at 4 g/L. L-glutamine was allowed to be exhausted, no additional glutamine feeds were made for the entire culture duration. The culture was maintained at 35° C. from Day 0 until harvest.

Cultivation of cultures SF97, SF98 and SF99 took place in an incubator with a controlled humidity of 85% and a $CO_2$ level of 5%. The cultures were agitated at a rate of 125 RPM.

Harvest was performed when the viability of the culture declined to between 60% and 70%. Samples were stored frozen until N-glycan analysis was performed.

Figure 14:
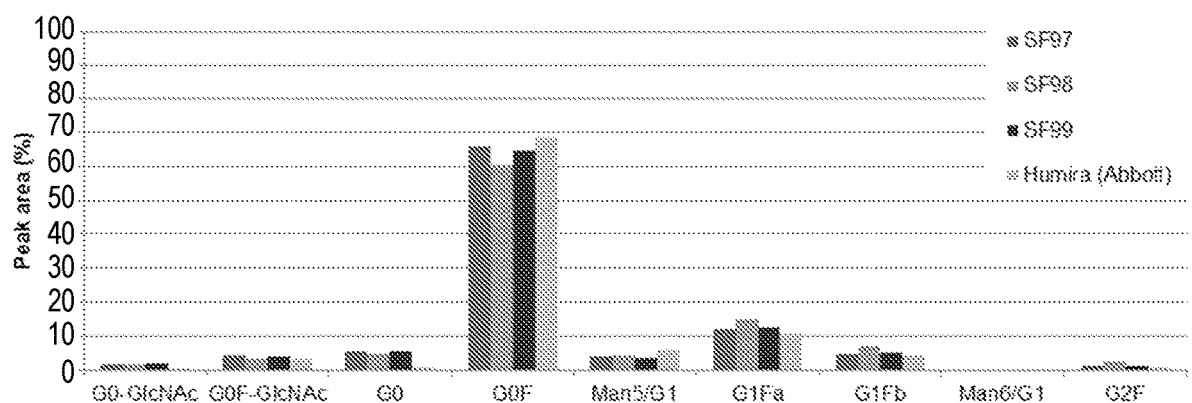
FIG. 14 is a graph showing the glycoprofile of adalimumab samples from the low glucose production method of Example 7, Experiment #5 compared to Humira®.

The results of the analysis are shown below in Table 5, and graphically in FIGS. 15 and 16. FIG. 14 is a graph showing the glycoprofile of adalimumab samples from the low glucose production method of Example 7, Experiment #5 compared to Humira®.

Figure 15:
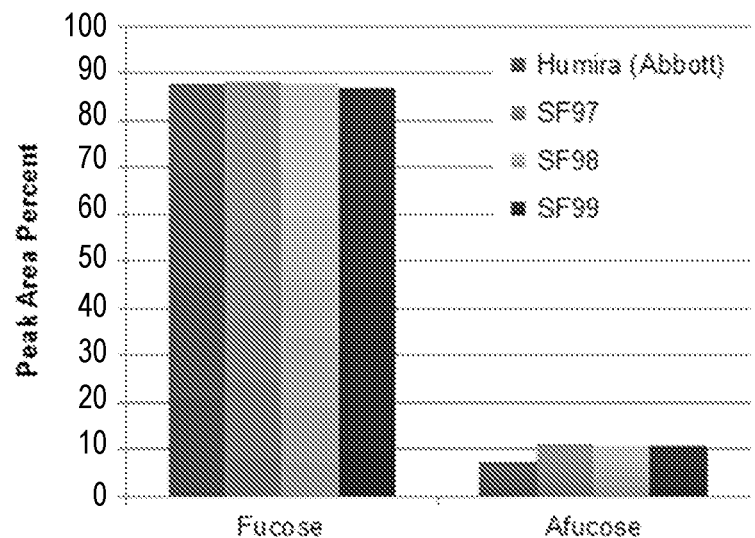
FIGS. 15 and 16 show the major groups of glycoforms of adalimumab samples from the low glucose production method of Example 7, Experiment #5 compared to Humira®.
Figure 16:
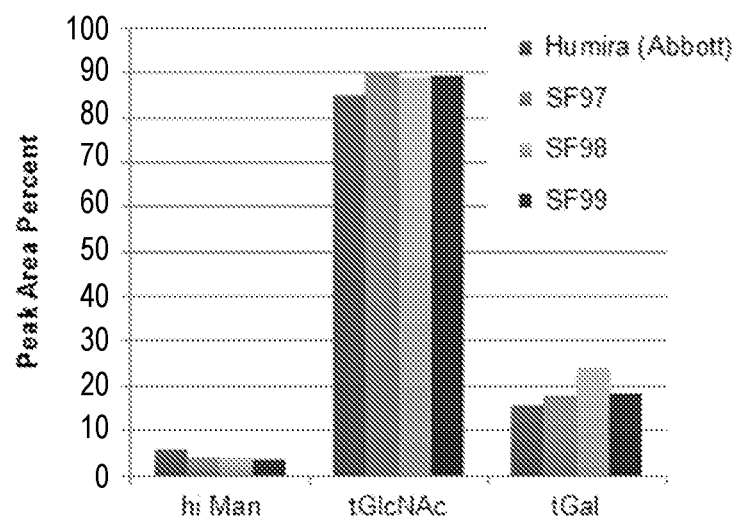

FIGS. 15 and 16 show the major groups of glycoforms of adalimumab samples from the low glucose production method of Example 7, Experiment #5 compared to Humira®.

TABLE 5

| | Fucosylation | Afucosylation | Tgal | TGlcNac | High Man |
|---|---|---|---|---|---|
| SF 97 | 88.3 | 11.1 | 17.9 | 90 | 4 |
| SF 98 | 87.9 | 10.6 | 24.1 | 88.9 | 4.2 |
| SF 99 | 87.1 | 10.9 | 18.5 | 89.3 | 3.7 |
| Humira ® | 87.8 | 7.1 | 15.8 | 84.8 | 5.8 |

Example 8. Experiment #6

Shake Flask C43A #12 (SF C43A #12)

Fifty (50) mLs of glucose-free BalanCD® Growth A medium (Irvine Scientific, cat #99850), supplemented with 6 mM L-glutamine and 0.7 g/L glucose, was inoculated in order to achieve an initial viable cell density of $0.5 \times 10^6$ cells/mL. The culture was fed with Feed1 (Irvine Scientific, glucose-free formulation of product Catalog No. 91127) on Day 0 (10% of the original culture volume) and Days 3 and 6 (2.5% of the original culture volume). Glucose level was maintained at 0.7 g/L for the entire duration of the culture. Mannose was added on Day 0 at 1.8 g/L. L-glutamine was maintained at 4 mM for the duration of the culture. The culture was maintained at 37° C. from Day 0 until harvest.

Shake Flask C43B #16 (SF C43B #16)

Fifty (50) mLs of glucose-free BalanCD® Growth A medium (Irvine Scientific, cat #99850), supplemented with 6 mM L-glutamine and 0.7 g/L glucose, was inoculated in order to achieve an initial viable cell density of $0.5 \times 10^6$ cells/mL. The culture was fed with Feed1 (Irvine Scientific, glucose-free formulation of product Catalog No. 91127) on Day 0 (10% of the original culture volume) and Days 3 and 6 (2.5% of the original culture volume). Glucose level was maintained at 0.7 g/L for the entire duration of the culture. Mannose was added on Day 0 at 1.8 g/L. L-glutamine was maintained at 4 mM for the duration of the culture. Sodium butyrate was added on Day 3 at a final concentration of 1 mM. The cultures were maintained at 37° C. from Day 0 until harvest.

Shake Flask C47 #30 (SF C47 #30)

Fifty (50) mLs of glucose-free BalanCD® Growth A medium (Irvine Scientific, cat #99850), supplemented with 6 mM L-glutamine and 0.7 g/L glucose, was inoculated in order to achieve an initial viable cell density of $0.5 \times 10^6$ cells/mL. The culture was fed with Feed1 (Irvine Scientific, glucose-free formulation of product Catalog No. 91127) on Day 0 (10% of the original culture volume) and Days 3 and 6 (2.5% of the original culture volume). Glucose level was maintained at 0.7 g/L for the entire duration of the culture. Lactate was added on Day 0 at a final concentration of 2 g/L. L-glutamine was maintained at 4 mM for the duration of the culture. The culture was maintained at 37° C. from Day 0 until harvest.

Shake Flask C48 #33 (SF C48 #33)

Fifty (50) mLs of glucose free BalanCD® Growth A medium (Irvine Scientific, cat #99850), supplemented with 6 mM L-glutamine and 0.7 g/L glucose, was inoculated in order to achieve an initial viable cell density of $1.0 \times 10^6$ cells/mL. The culture was fed with Feed1 (Irvine Scientific, glucose-free formulation of product Catalog No. 91127) on Day 0 (10% of the original culture volume) and Days 3 and 6 (2.5% of the original culture volume). Glucose level was maintained at 0.7 g/L for the entire duration of the culture. Lactate was added on Day 0 at a final concentration of 2 g/L. L-glutamine was maintained at 4 mM for the duration of the culture. The culture was maintained at 37° C. from Day 0 until harvest.

Figure 17:
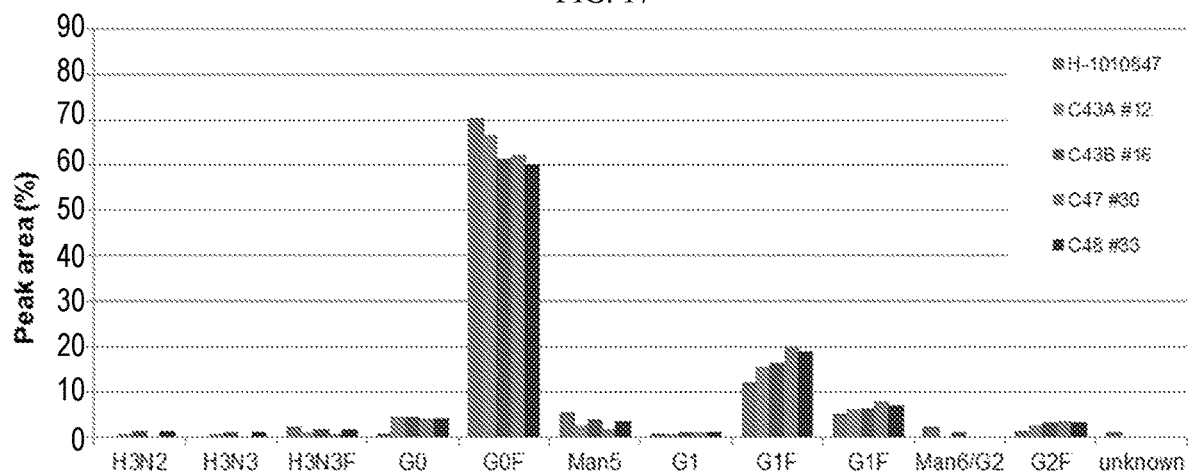
FIG. 17 is a graph showing the glycoprofile of adalimumab samples from the low glucose production method of Example 8, Experiment #6 compared to Humira® Lot #1017238.

The results of the analysis are shown below in Table 6, and graphically in FIGS. 18 and 19. FIG. 17 is a graph showing the glycoprofile of adalimumab samples from the low glucose production method of Example 8, Experiment #6 compared to Humira® Lot #1017238.

Figure 18:
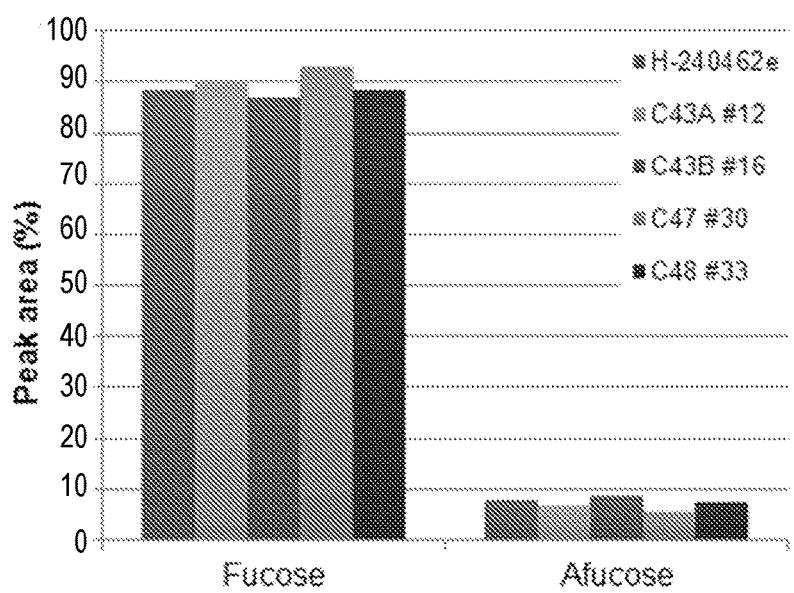
FIGS. 18 and 19 show the major groups of glycoforms of adalimumab samples from the low glucose production method of Example 8, Experiment #6 compared to Humira® Lot #1017238.
Figure 19:
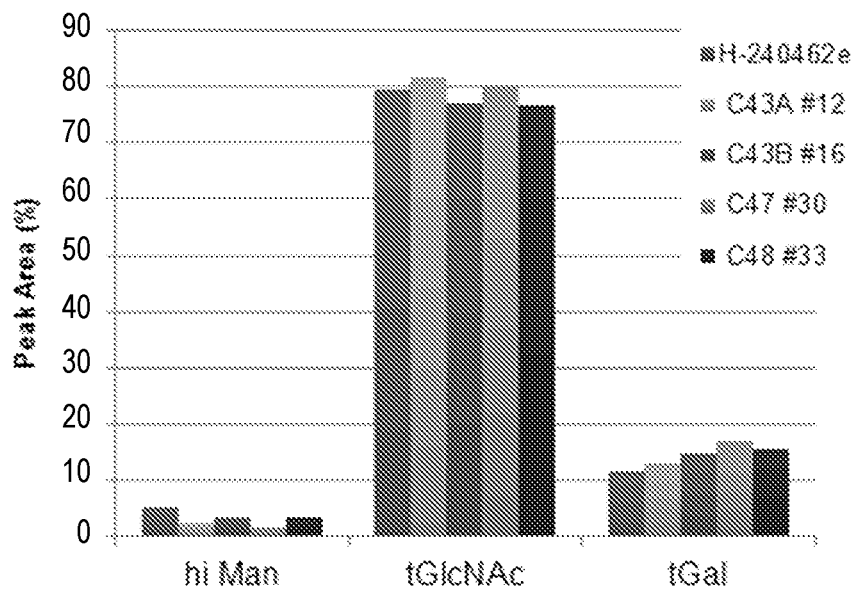

FIGS. 18 and 19 show the major groups of glycoforms of adalimumab samples from the low glucose production method of Example 8, Experiment #6 compared to Humira® Lot #1017238.

TABLE 6

|  | Fucosylation | Afucosylation | Tgal | TGlcNac | High Man |
|---|---|---|---|---|---|
| C43A#12 | 90.5 | 6.8 | 13.2 | 81.6 | 2.5 |
| C43B#16 | 86.8 | 8.7 | 14.9 | 77.1 | 3.6 |
| C47#30 | 93 | 5.5 | 17.1 | 79.8 | 1.6 |
| C48#33 | 88.5 | 7.3 | 15.7 | 76.7 | 3.4 |
| Humira® Lot #1017238 | 88.3 | 7.9 | 11.7 | 79.4 | 5.2 |

Example 9. Experiment #7

Shake Flask A-103 (SF A-103)

Fifty (50) mLs of glucose-free BalanCD® Growth A medium (Irvine Scientific, cat #99850), supplemented with 8 mM L-glutamine and 0.7 g/L glucose, was inoculated in order to achieve an initial viable cell density of $0.5 \times 10^6$ cells/mL. The culture was fed with Feed1 (Irvine Scientific, glucose-free formulation of product Catalog No. 91127) on Day 0 (10% of the original culture volume) and Days 3, 5 and 7 (3.5% of the original culture volume). Glucose level was maintained at 0.7 g/L for the entire duration of the culture. L-glutamine was allowed to exhaust, there was no additional feeding. The culture was maintained at 35° C. from Day 0 until harvest.

Shake Flask A-104 (SF A-104)

Fifty (50) mLs of glucose free BalanCD® Growth A medium (Irvine Scientific, cat #99850), supplemented with 8 mM L-glutamine and 0.7 g/L glucose, was inoculated in order to achieve an initial viable cell density of $0.5 \times 10^6$ cells/mL. The culture was fed with Feed1 (Irvine Scientific, glucose-free formulation of product Catalog No. 91127) on Day 0 (10% of the original culture volume) and Days 3, 5 and 7 (3.5% of the original culture volume). Glucose level was maintained at 0.7 g/L for the entire duration of the culture. Additionally, mannose at 1 g/L was added daily from Day 0 until harvest. L-glutamine was allowed to exhaust, there was no additional feeding. The culture was maintained at 35° C. from Day 0 until harvest.

Shake Flask A-106 (SF A-106)

Figure 20:
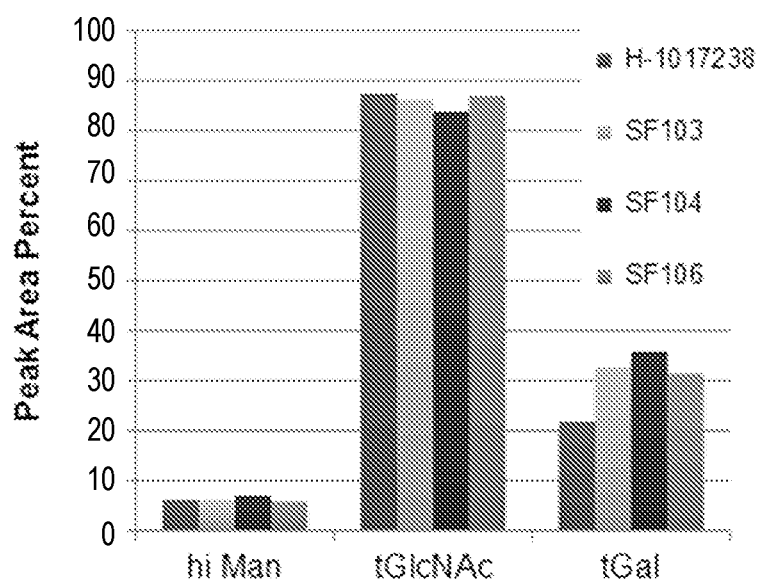
FIGS. 20 and 21 show the major groups of glycoforms of adalimumab samples from the low glucose production method of Example 9, Experiment #7 compared to Humira® Lot #1017238.
Figure 21:
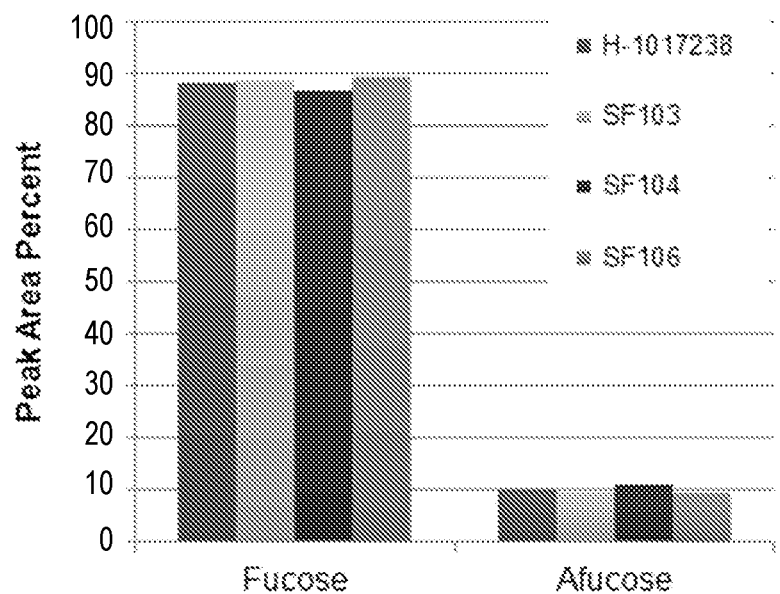

Fifty (50) mLs of glucose-free BalanCD® Growth A medium (Irvine Scientific, cat #99850), supplemented with 8 mM L-glutamine and 0.7 g/L glucose, was inoculated in order to achieve an initial viable cell density of $0.5 \times 10^6$ cells/mL. The culture was fed with Feed1 (Irvine Scientific, glucose-free formulation of product Catalog No. 91127) on Day 0 (10% of the original culture volume) and Days 3, 5 and 7 (3.5% of the original culture volume). Glucose level was maintained at 0.7 g/L for the entire duration of the culture. Additionally, mannose and maltose were added daily at 1 g/L each from Day 0 until harvest. L-glutamine was allowed to exhaust, there was no additional feeding. The culture was maintained at 35° C. from Day 0 until harvest. The results of the analysis are shown below in Table 7, and graphically in FIGS. 20 and 21. FIGS. 20 and 21 show the major groups of glycoforms of adalimumab samples from the low glucose production method of Example 9, Experiment #7 compared to Humira® Lot #1017238.

TABLE 7

|  | Fucosylation | Afucosylation | Tgal | TGlcNac | High Man |
|---|---|---|---|---|---|
| SF102 | 89.9 | 9.3 | 31.6 | 87 | 6.5 |
| SF103 | 88.7 | 9.5 | 32.5 | 86.1 | 6 |
| SF104 | 87 | 11.2 | 35.8 | 83.7 | 6.9 |
| SF106 | 89.4 | 9.5 | 31.5 | 86.9 | 5.9 |
| Humira® Lot #1017238 | 88.3 | 10.5 | 21.7 | 87.4 | 6.2 |

Example 10. Experiment #8

Shake Flask A 141 (S #A 141)

Cell expansion—CHO cells were cultivated in glucose free CD-C4 medium (Biochrom, Millipore, cat #F9235-200), supplemented with 6 mM L-glutamine, 50 µg/L IGF1 LongR3 and 6 g/L mannose. The culture was maintained at 37° C. in an 8% $CO_2$ shaker incubator with controlled humidity (85%) and rotating speed of 150 RPM.

Experimental vessels—shake flasks containing 50 mLs of C4 medium (glucose-free formulation, Biochrom, cat #F9235-200), supplemented with 6 mM L-glutamine, 50 µg/L IGF1 LongR3, 1.3 g/L mannose, 4 g/L maltose and 0.7 g/L glucose, were inoculated at $0.5 \times 10^6$ cells per mL of culture. On Days 3 to 7, the culture was fed daily with Feed1 (Irvine Scientific, glucose-free formulation of product Catalog No. 91127) at 5% of the original culture volume. From Day 8 until harvest, Feed1 addition was made at 7% of the original culture volume. Feed1 was supplemented with 14 g/L mannose, 13 g/L maltose and 3.5 g/L glucose. Final concentration of each sugar added daily was: Days 3, 4, 5, 6, and 7: 0.7 g/L mannose, 0.65 g/L maltose and 0.175 g/L glucose; and Days 7 until harvest: 0.98 g/L mannose, 0.91 g/L maltose and 0.25 g/L glucose. The culture was maintained at 37° C. in an 8% $CO_2$ shaker incubator with controlled humidity (85%) and rotating speed of 150 RPM.

Shake Flask A 144 (SF #A 144)

Cell expansion—CHO cells were cultivated in glucose-free CD-C4 medium (Biochrom, Millipore, cat #F9235-200), supplemented with 6 mM L-glutamine, 50 µg/L IGF1 LongR3 and 6 g/L mannose. The culture was maintained at 37° C. in an 8% $CO_2$ shaker incubator with controlled humidity (85%) and rotating speed of 150 RPM.

Experimental vessels—shake flasks containing 50 mLs of C4 medium (glucose-free formulation, Biochrom, cat #F9235-200), supplemented with 6 mM L-glutamine, 50 µg/L IGF1 LongR3, 5.3 g/L mannose and 0.7 g/L glucose, were inoculated at $0.5 \times 10^6$ cells per mL of culture. On Days 3 to 7, the culture was fed daily with Feed1 (Irvine Scientific, glucose-free formulation of product Catalog No. 91127) at 5% of the original culture volume. From Day 8 until harvest, Feed1 addition was made at 7% of the original culture volume. Feed1 was supplemented with 20 g/L mannose, 5 g/L maltose, 1.5 g/L fructose and 3.5 g/L glucose. Resulting final concentrations of each sugar added daily was, for Days 3, 4, 5, 6, and 7: 1 g/L mannose, 0.25 g/L maltose, 0.075 g/L fructose and 0.175 g/L glucose; and for Day 7 until harvest: 1.4 g/L mannose, 0.35 g/L maltose, 0.1 g/L fructose and 0.25 g/L glucose. The culture was maintained at 37° C. in an 8% $CO_2$ shaker incubator with controlled humidity (85%) and rotating speed of 150 RPM.

Shake Flask A 147 (SF #A 147)

Cell expansion—CHO cells were cultivated in glucose-free CD-C4 medium (Biochrom, Millipore, cat #F9235-200) supplemented with 6 mM L-glutamine, 50 µg/L IGF1 LongR3 and 6 g/L mannose. The culture was maintained at 37° C. in 8% $CO_2$ shaker incubator with controlled humidity (85%) and rotating speed of 150 RPM.

Experimental vessels—shake flasks containing 50 mLs of C4 medium (glucose-free formulation, Biochrom, cat #F9235-200), supplemented with 6 mM L-glutamine, 50 μg/L IGF1 LongR3, 3.3 g/L mannose, 2 g/L maltose and 0.7 g/L glucose, were inoculated at $0.5 \times 10^6$ cells per mL of culture. On Days 3 to 7, culture was fed daily with Feed1 (Irvine Scientific, glucose-free formulation of product Catalog No. 91127) at 5% of the original culture volume. From Day 8 until harvest, Feed1 addition was made at 7% of the original culture volume. Feed1 was supplemented with 6.5 g/L mannose, 20 g/L maltose, and 3.5 g/L glucose. Resulting final concentrations of each sugar added daily was, for Days 3, 4, 5, 6, and 7: 0.325 g/L mannose, 1 g/L maltose and 0.175 g/L glucose; and for Days from day 7 until harvest: 0.46 g/L mannose, 1.4 g/L maltose and 0.25 g/L glucose. The culture received N-acetylglucosamine ("GlcNac") on Days 2 and 6 at final concentration of 5 mM. The culture was maintained at 37° C. in 8% $CO_2$ shaker incubator with controlled humidity (85%) and rotating speed of 150 RPM.

Shake Flask A 148 (SF #A 148)

Cell expansion—CHO cells were cultivated in glucose-free CD-C4 medium (Biochrom, Millipore, cat #F9235-200), supplemented with 6 mM L-glutamine, 50 μg/L IGF1 LongR3 and 6 g/L mannose. The culture was maintained at 37° C. in an 8% $CO_2$ shaker incubator with controlled humidity (85%) and rotating speed of 150 RPM.

Experimental vessels—shake flasks containing 50 mLs of C4 medium (glucose-free formulation, Biochrom, cat #F9235-200), supplemented with 6 mM L-glutamine, 50 μg/L IGF1 LongR3, 5.3 g/L mannose and 0.7 g/L glucose, were inoculated at $0.5 \times 10^6$ cells per mL of culture. On Days 3 to 7, the culture was fed with Feed1 (Irvine Scientific, glucose-free formulation of product Catalog No. 91127) at 5% of the original culture volume. From Day 8 until harvest, Feed1 addition was made at 7% of the original culture volume. Feed1 was supplemented with 26.5 g/L mannose and 3.5 g/L glucose. Resulting final concentrations of each sugar added daily was, for Days 3, 4, 5, 6, and 7: 1.33 g/L mannose and 0.175 g/L glucose, and from Day 7 until harvest day: 1.86 g/L mannose and 0.25 g/L glucose. The culture received GlcNac on Days 2 and 6 at a final concentration of 5 mM on each day. The culture was maintained at 37° C. in an 8% $CO_2$ shaker incubator with controlled humidity (85%) and rotating speed of 150 RPM.

Shake Flask A149 (SF #A 149)

Cell expansion—CHO cells were cultivated in glucose free CD-C4 medium (Biochrom, Millipore, cat #F9235-200), supplemented with 6 mM L-glutamine, 50 μg/L IGF1 LongR3 and 6 g/L mannose. The culture was maintained at 37° C. in an 8% $CO_2$ shaker incubator with controlled humidity (85%) and rotating speed of 150 RPM.

Experimental vessels—shake flasks containing 50 mLs of C4 medium (glucose-free formulation, Biochrom, cat #F9235-200), supplemented with 6 mM L-glutamine, 50 μg/L IGF1 LongR3, 1.3 g/L mannose, 4 g/L maltose and 0.7 g/L glucose, were inoculated at $0.5 \times 10^6$ cells per mL of culture. On Days 3 to 7, culture was fed daily with Feed1 (Irvine Scientific, glucose-free formulation of product Catalog No. 91127) at 5% of the original culture volume. From Day 8 until harvest, Feed1 addition was made at 7% of the original culture volume. Feed1 was supplemented with 14 g/L mannose, 13 g/L maltose and 3.5 g/L glucose. Resulting final concentrations of each sugar added daily was, for Days 3, 4, 5, 6, and 7: 0.7 g/L mannose, 0.65 g/L maltose and 0.175 g/L glucose; and from Day 7 until harvest: 0.98 g/L mannose, 0.91 g/L maltose and 0.25 g/L glucose. The culture received GlcNac on Days 2 and 6 at a final concentration of 5 mM on each day. The culture was maintained at 37° C. in 8% $CO_2$ shaker incubator with controlled humidity (85%) and rotating speed of 150 RPM.

Shake Flask A153 (SF #A 153)

Cell expansion—CHO cells were cultivated in glucose-free CD-C4 medium (Biochrom, Millipore, cat #F9235-200), supplemented with 6 mM L-glutamine, 50 μg/L IGF1 LongR3 and 6 g/L mannose. The culture was maintained at 37° C. in an 8% $CO_2$ shaker incubator with controlled humidity (85%) and rotating speed of 150 RPM.

Experimental vessels—shake flasks containing 50 mLs of C4 medium (glucose-free formulation, Biochrom, cat #F9235-200), supplemented with 6 mM L-glutamine, 50 μg/L IGF1 LongR3, 5.3 g/L mannose and 0.7 g/L glucose, were inoculated at $0.5 \times 10^6$ cells per mL of culture. On Days 3 to 7, the culture was fed daily with Feed1 (Irvine Scientific, glucose-free formulation of product Catalog No. 91127) at 5% of the original culture volume. From Day 8 until harvest, Feed1 addition was made at 7% of the original culture volume. Feed1 was supplemented with 20 g/L mannose, 1.5 g/L maltose, 5 g/L fructose and 3.5 g/L glucose. The resulting final concentrations of each sugar added daily was, for Days 3, 4, 5, 6, and 7: 1 g/L mannose, 0.075 g/L maltose, 0.25 g/L fructose and 0.175 g/L glucose; and from Day 7 until harvest: 1.4 g/L mannose, 0.1 g/L maltose, 0.35 g/L fructose and 0.25 g/L glucose. The culture received GlcNac on Days 2 and 6 at a final concentration of 5 mM on each day. The culture was maintained at 37° C. in an 8% $CO_2$ shaker incubator with controlled humidity (85%) and rotating speed of 150 RPM.

Shake Flask #A154 (SF #A154)

Cell expansion—CHO cells were cultivated in glucose-free CD-C4 medium (Biochrom, Millipore, cat #F9235-200), supplemented with 6 mM L-glutamine, 50 μg/L IGF1 LongR3 and 6 g/L mannose. The culture was maintained at 37° C. in an 8% $CO_2$ shaker incubator with controlled humidity (85%) and rotating speed of 150 RPM.

Experimental vessels—shake flasks containing 50 mLs of C4 medium (glucose-free formulation, Biochrom, cat #F9235-200), supplemented with 6 mM L-glutamine, 50 μg/L IGF1 LongR3, 5.3 g/L mannose and 0.7 g/L glucose, were inoculated at $0.5 \times 10^6$ cells per mL of culture. On Days 3 to 7, the culture was fed daily with Feed1 (Irvine Scientific, glucose-free formulation of product Catalog No. 91127) at 5% of the original culture volume. From Day 8 until harvest, Feed1 addition was made at 7% of the original culture volume. Feed1 was supplemented with 16.5 g/L mannose, 5 g/L maltose, 5 g/L fructose and 3.5 g/L glucose. The resulting final concentrations of each sugar added daily was, for Days 3, 4, 5, 6, and 7: 0.825 g/L mannose, 0.25 g/L maltose, 0.25 g/L fructose and 0.175 g/L glucose; and from Day 7 until harvest: 1.16 g/L mannose, 0.35 g/L maltose, 0.35 g/L fructose and 0.25 g/L glucose. The culture received GlcNac on Days 2 and 6 at a final concentration of 5 mM on each day. The culture was maintained at 37° C. in an 8% $CO_2$ shaker incubator with controlled humidity (85%) and rotating speed of 150 RPM.

Figure 22:
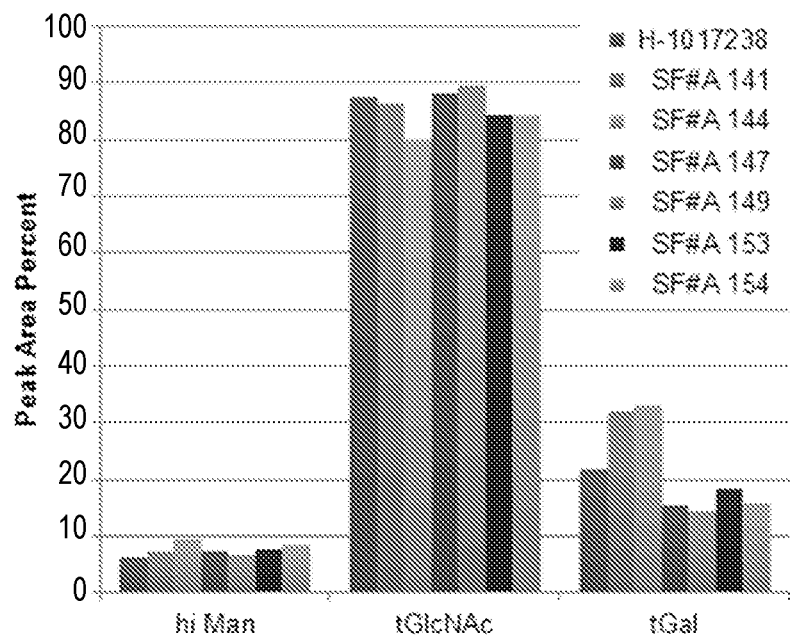
FIGS. 22 and 23 show the major groups of glycoforms of adalimumab samples from the low glucose production method of Example 10, Experiment #8 compared to Humira® Lot #1017238.
Figure 23:
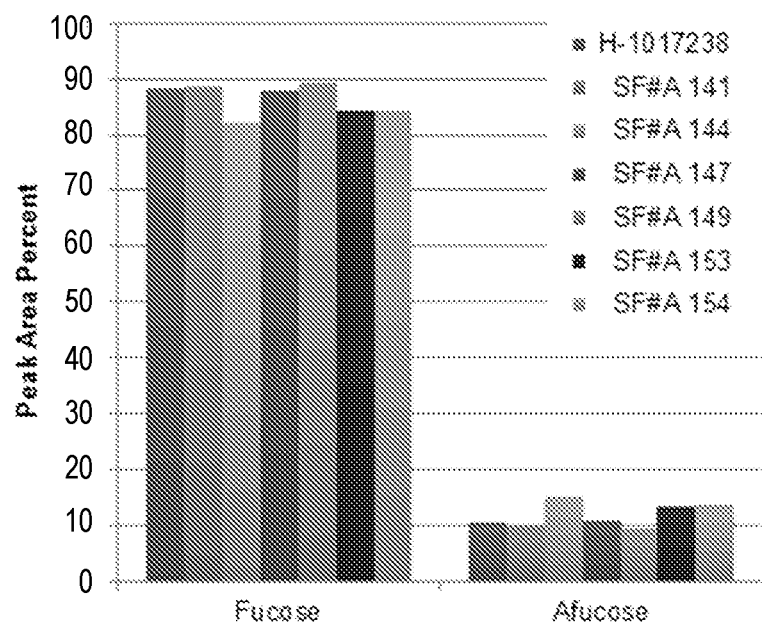

The results of the analysis are shown below in Table 8, and graphically in FIGS. 22 and 23. FIGS. 22 and 23 show the major groups of glycoforms of adalimumab samples from the low glucose production method of Example 10, Experiment #8 compared to Humira® Lot #1017238.

TABLE 8

|  | Fucosylation | Afucosylation | Tgal | TGlcNac | High Man |
|---|---|---|---|---|---|
| SF#A 141 | 88.7 | 10.2 | 31.9 | 86.5 | 7.3 |
| SF#A 144 | 82.3 | 15 | 33 | 80.1 | 9.5 |
| SF#A 147 | 88 | 10.7 | 15.3 | 88.1 | 7.2 |
| SF#A 149 | 89.5 | 9.5 | 14.2 | 89.7 | 6.5 |
| SF#A 153 | 84.5 | 13.1 | 18.2 | 84.3 | 7.7 |
| SF#A 154 | 84.2 | 13.6 | 15.8 | 84.4 | 8.4 |
| Humira ® Lot #1017238 | 88.3 | 10.5 | 21.7 | 87.4 | 6.2 |

Example 11. Experiment #9

Shake Flask A111 (SF A111)

Fifty (50) mLs of glucose-free BalanCD® Growth A medium (Irvine Scientific, cat #99850), supplemented with 8 mM L-glutamine and 0.7 g/L glucose, was inoculated in order to achieve an initial viable cell density of $0.5 \times 10^6$ cells/mL. L-glutamine was allowed to exhaust, there was no additional feed with glutamine.

The culture was fed with Feed1 (Irvine Scientific, glucose-free formulation of product Catalog No. 91127). On Day 0, the culture received 10% of Feed1 based on the original culture volume; on Days 3, 5, 7 and 9, feed was decreased to 3.5% of the original culture volume. Additionally, fructose was added on Days 0, 1, 2, 4 at 2 g/L on each day. From Day 5 until harvest, the culture received 3 g/L of fructose daily based on the original culture volume. The culture was maintained at 35° C. from Day 0 until harvest.

Figure 24:
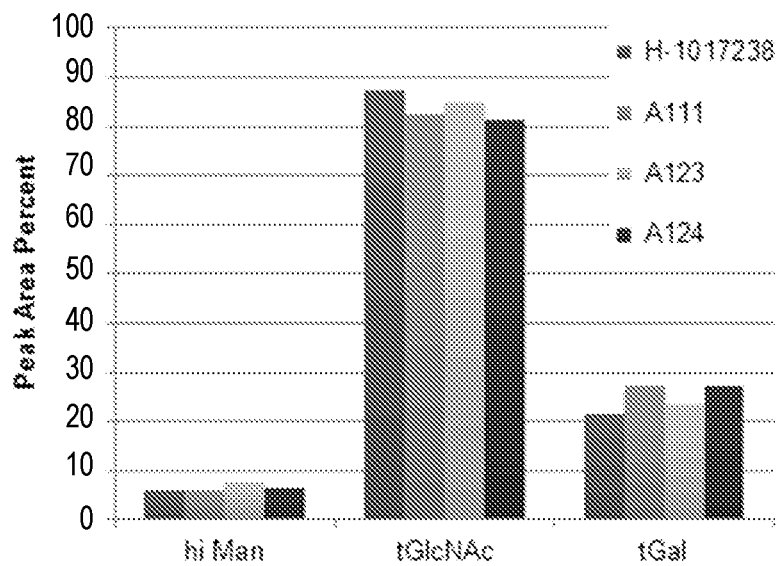
FIGS. 24 and 25 show the major groups of glycoforms of adalimumab samples from the low glucose production method of Example 11, Experiment #9 compared to Humira® Lot #1017238.
Figure 25:
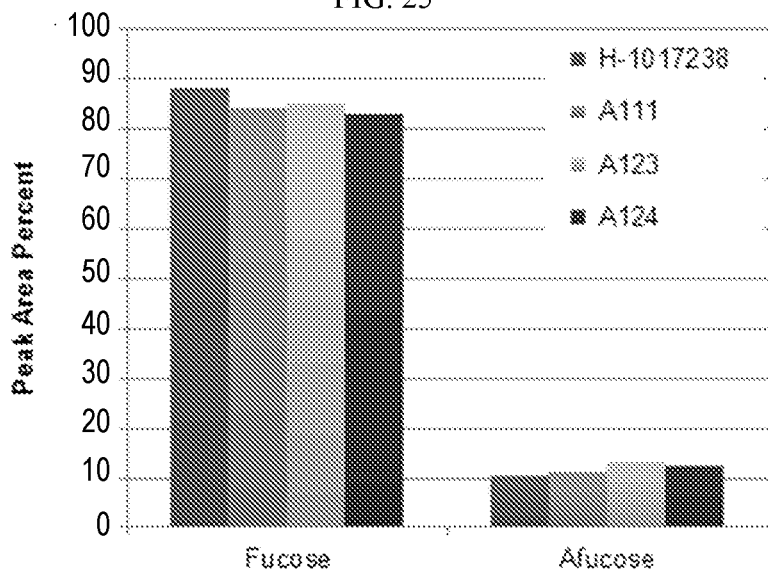

The results of the analysis are shown below in Table 9, and graphically in FIGS. 24 and 25. FIGS. 24 and 25 show the major groups of glycoforms of adalimumab samples from the low glucose production method of Example 11, Experiment #9 compared to Humira® Lot #1017238.

TABLE 9

|  | Fucosylation | Afucosylation | Tgal | TGlcNac | High Man |
|---|---|---|---|---|---|
| SF#A 141 | 84.3 | 11.3 | 27.2 | 82.6 | 6 |
| SF#A 144 | 85 | 13.3 | 23.4 | 84.8 | 7.8 |
| SF#A 147 | 83 | 12.2 | 27.1 | 81.3 | 6.5 |
| Humira ® Lot #1017238 | 88.3 | 10.5 | 21.7 | 87.4 | 6.2 |

Example 12. Experiment #10

Shake Flask 74 (SF74)

Fifty (50) mLs of glucose free BalanCD® Growth A medium (Irvine Scientific, cat #99850), supplemented with 8 mM L-glutamine and 2.5 g/L glucose, was inoculated in order to achieve an initial viable cell density of $0.5 \times 10^6$ cells/mL. L-glutamine was allowed to exhaust, there was no additional feed with glutamine. Glucose was maintained in range between 2.5 g/L and 1 g/L from Day 0 to Day 4. From Day 4, glucose level was maintained as close as possible to 1.8 g/L.

The culture was fed with Feed1 (Irvine Scientific, glucose-free formulation of product Catalog No. 91127). On Day 0, the culture received 10% of Feed1 based on the original culture volume; on Days 3 and 6, feed was decreased to 2.5% of the original culture volume. The culture was maintained at 34° C. from Day 0 until harvest.

Shake Flask 78 (SF78)

Fifty (50) mLs of glucose-free BalanCD® Growth A medium (Irvine Scientific, cat #99850), supplemented with 8 mM L-glutamine and 2.5 g/L glucose, was inoculated in order to achieve an initial viable cell density of $0.5 \times 10^6$ cells/mL. L-glutamine was allowed to exhaust, there was no additional feed with glutamine. Glucose was maintained in ranges between 2.5 g/L and 1 g/L from Day 0 to Day 4. From Day 4, glucose level was maintained as close as possible to 1.8 g/L.

The culture was fed with Feed1 (Irvine Scientific, glucose-free formulation of product Catalog No. 91127). On Day 0, the culture received 10% of Feed1 based on the original culture volume; on Days 3 and 6, feed was decreased to 2.5% of the original culture volume. The culture was maintained at 37° C. from Day 0 until harvest.

Shake Flask 80 (SF80)

Fifty (50) mLs of glucose free BalanCD® Growth A medium (Irvine Scientific, cat #99850), supplemented with 8 mM L-glutamine and 2.5 g/L glucose, was inoculated in order to achieve an initial viable cell density of $0.5 \times 10^6$ cells/mL. L-glutamine was allowed to exhaust, there was no additional feed with glutamine. Glucose was maintained in ranges between 2.5 g/L and 1 g/L from Day 0 to Day 4. From Day 4, glucose level was maintained as close as possible to 1.8 g/L.

The culture was fed with Feed1 (Irvine Scientific, glucose-free formulation of product Catalog No. 91127). On Day 0, the culture received 10% of Feed1 based on the original culture volume; on Days 3 and 6, feed was decreased to 2.5% of the original culture volume. Additionally, the culture received fructose on Days 0, 1, 2 and 3; each addition was made at 2 g/L of the final concentration based on the original culture volume. From Day 4 until Day 8, the culture received daily fructose at 4 g/L based on the original culture volume. The culture was maintained at 34° C. from Day 0 until harvest.

Figure 26:
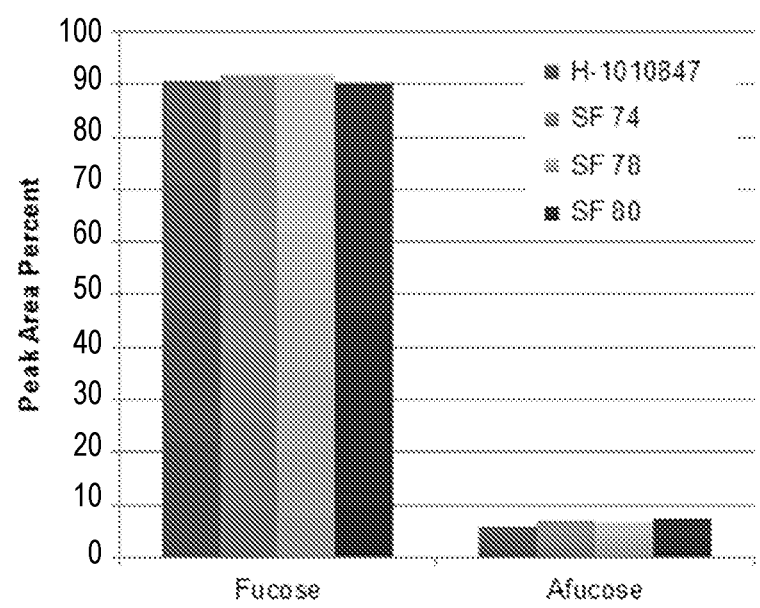
FIGS. 26 and 27 show the major groups of glycoforms of adalimumab samples from the low glucose production method of Example 12, Experiment #10 compared to Humira® Lot #1010847.
Figure 27:
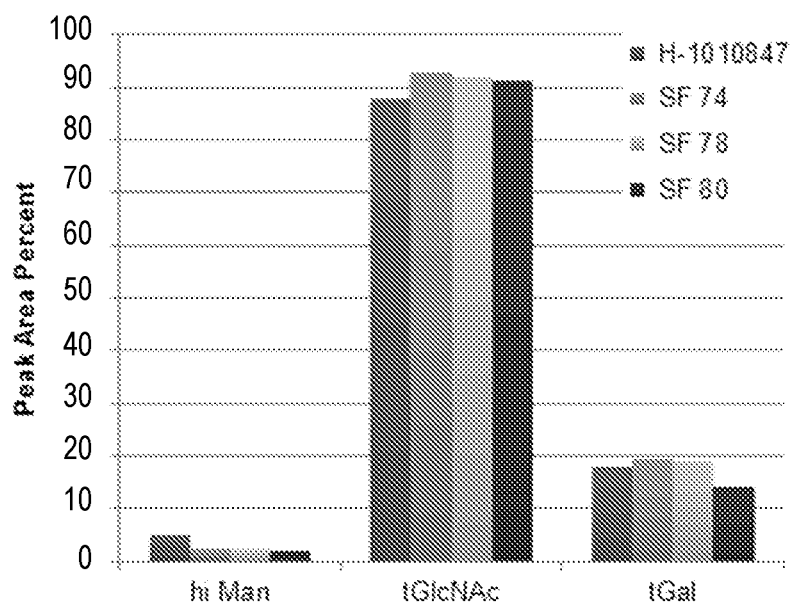

The results of the analysis are shown below in Table 10, and graphically in FIGS. 26 and 27. FIGS. 26 and 27 show the major groups of glycoforms of adalimumab samples from the low glucose production method of Example 12, Experiment #10 compared to Humira® Lot #1010847.

TABLE 10

|  | Fucosylation | Afucosylation | Tgal | TGlcNac | High Man |
|---|---|---|---|---|---|
| SF 74 | 91.6 | 6.9 | 19.6 | 92.8 | 2.2 |
| SF 78 | 91.9 | 6.7 | 19 | 91.9 | 2.3 |
| SF 80 | 90.2 | 7.3 | 14.1 | 91.3 | 1.9 |
| Humira ® Lot #1010847 | 90.5 | 5.7 | 18.1 | 87.6 | 5.1 |

Example 12. Experiment #11

Shake Flask C-83 (SF C-83)

Fifty (50) mLs of glucose free BalanCD® Growth A medium (Irvine Scientific, cat #99850), supplemented with 6 mM L-glutamine, 0.7 g/L glucose and 3 g/L mannose, was inoculated in order to achieve an initial viable cell density of $0.5 \times 10^6$ cells/mL. L-glutamine was maintained at a concentration between 2 mM and 4 mM. Glucose was maintained at 0.7 g/L. The culture was fed with Feed1 (Irvine Scientific, glucose-free formulation of product Catalog No. 91127). On Day 0, the culture received 10% of Feed1 based on the original culture volume; on Days 3, 5 and 7, feed was decreased to 3% of the original culture volume. The culture was maintained at 37° C. from Day 0 until harvest.

Shake Flask C-87 (SF C-87)

Fifty (50) mLs of glucose-free BalanCD® Growth A medium (Irvine Scientific, cat #99850), supplemented with 6 mM L-glutamine, 0.7 g/L glucose and 3 g/L mannose, was inoculated in order to achieve an initial viable cell density of $0.5 \times 10^6$ cells/mL. L-glutamine was maintained at a concentration between 2 mM and 4 mM. Glucose was maintained at 0.7 g/L. The culture was fed with Feed1 (Irvine Scientific, glucose-free formulation of product Catalog No. 91127). On Day 0, the culture received 10% of Feed1 based on the original culture volume; on Days 3, 5 and 7, the feed was decreased to 3% of the original culture volume. Additionally, the culture received 0.5 g/L lactate on Day 4. The culture was maintained at 37° C. from Day 0 until harvest.

Shake Flask C-89 (SF C-89)

Fifty (50) mLs of glucose-free BalanCD® Growth A medium (Irvine Scientific, cat #99850), supplemented with 6 mM L-glutamine, 0.7 g/L glucose and 3 g/L mannose, was inoculated in order to achieve an initial viable cell density of $0.5 \times 10^6$ cells/mL. L-glutamine was allowed to exhaust, there was no additional feeding. Glucose was maintained at 0.7 g/L. The culture was fed with Feed1 (Irvine Scientific, glucose-free formulation of product Catalog No. 91127). On Day 0, the culture received 10% of Feed1 based on the original culture volume; on Day 3, the culture received 5%; on Day 5, the culture received 3.5%; and on Day 7, the culture received 3% of Feed1 based on the original culture volume. Additionally, the culture received maltose feed at 3 g/L on Days 2, 4 and 6 based on the original culture volume. The culture was maintained at 37° C. from Day 0 until harvest.

Shake Flask C-91 (SF C-91)

Fifty (50) mLs of glucose-free BalanCD® Growth A medium (Irvine Scientific, cat #99850), supplemented with 6 mM L-glutamine, 0.7 g/L glucose and 3 g/L mannose, was inoculated in order to achieve an initial viable cell density of $0.5 \times 10^6$ cells/mL. L-glutamine was allowed to exhaust, there was no additional feeding. Glucose was maintained at 0.7 g/L. The culture was fed with Feed1 (Irvine Scientific, glucose-free formulation of product Catalog No. 91127). On Day 0, the culture received 10% of Feed1 based on the original culture volume; on Day 3, the culture received 5%; on Day 5, the culture received 3.5%; and on Day 7, the culture received 3% of Feed1 based on the original culture volume. Additionally, the culture received fructose feed at 3 g/L on Days 2, 4 and 6 based on the original culture volume. The culture was maintained at 37° C. from Day 0 until harvest.

Figure 28:
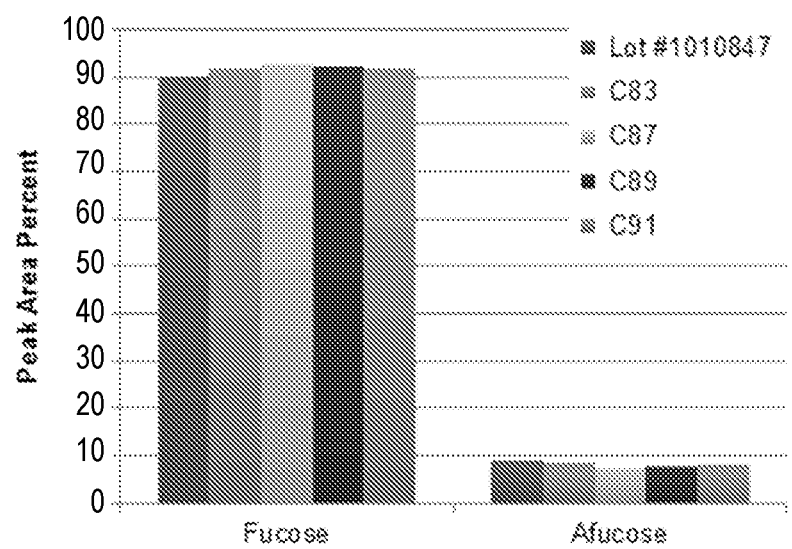
FIGS. 28 and 29 show the major groups of glycoforms of adalimumab samples from the low glucose production method of Example 12, Experiment #10 compared to Humira® Lot #1010847.
Figure 29:
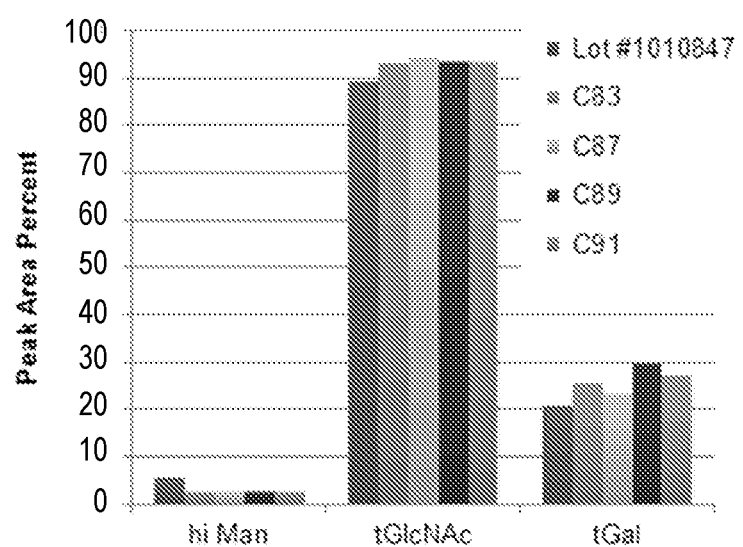

The results of the analysis are shown below in Table 11, and graphically in FIGS. 28 and 29. FIGS. 28 and 29 show the major groups of glycoforms of adalimumab samples from the low glucose production method of Example 12, Experiment #10 compared to Humira® Lot #1010847.

TABLE 11

| | Fucosylation | Afucosylation | Tgal | TGlcNac | High Man |
|---|---|---|---|---|---|
| C83 | 91.6 | 8.4 | 25.6 | 93.1 | 2.7 |
| C87 | 92.6 | 7.5 | 23.2 | 94.1 | 2.7 |
| C89 | 92.2 | 7.8 | 29.5 | 93.5 | 2.5 |
| C91 | 91.8 | 8.2 | 27 | 93.4 | 2.8 |
| Humira ® Lot #1010847 | 89.9 | 9.1 | 20.7 | 89.2 | 5.6 |

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

What is claimed is:

1. A liquid culture medium comprising:
   about 0.1 to about 0.9 grams/liter glucose; and
   at least one hexose selected from the group consisting of galactose, mannose, fructose, maltose, or a combination thereof, each at a concentration of about 0.1 to about 20 grams/liter.

2. The liquid culture medium of claim 1, wherein the liquid culture medium is a chemically-defined liquid culture medium.

3. The liquid culture medium of claim 1, wherein the liquid culture medium is an animal-derived component-free liquid culture medium.

4. The liquid culture medium of claim 1, wherein the liquid culture medium is a serum-free liquid culture medium.

5. The liquid culture medium of claim 1, wherein the liquid culture medium is a serum-containing liquid culture medium.

6. The liquid culture medium of claim 1, wherein the liquid culture medium further comprises L-glutamine.

7. The liquid culture medium of claim 1, wherein the liquid culture medium further comprises insulin growth factor 1 (IGF1).

8. The liquid culture medium of claim 1, wherein the liquid culture medium further comprises L-glutamine and IGF1.

9. The liquid culture medium of claim 1, wherein the liquid culture medium comprises at least one hexose selected from the group consisting of galactose, mannose, fructose, or a combination thereof, each at a concentration of about 0.1 g/L to about 20 g/L.

10. The liquid culture medium of claim 9, wherein the liquid culture medium comprises galactose, mannose, and fructose, each at a concentration of about 0.1 g/L to about 20 g/L.

11. The liquid culture medium of claim 10, wherein the liquid culture medium further comprises L-glutamine.

12. The liquid culture medium of claim 11, wherein the liquid culture medium further comprises IGF1.

13. The liquid culture medium of claim 1, wherein the liquid culture medium comprises mannose at a concentration of about 0.1 g/L to about 20 g/L.

14. The liquid culture medium of claim 13, wherein the liquid culture medium further comprises L-glutamine.

15. The liquid culture medium of claim 14, wherein the liquid culture medium further comprises IGF1.

16. The liquid culture medium of claim 1, wherein the liquid culture medium comprises maltose at a concentration of 0.1 g/L to about 20 g/L.

17. The liquid culture medium of claim 16, wherein the liquid culture medium further comprises L-glutamine.

18. The liquid culture medium of claim 1, wherein the liquid culture medium comprises mannose and maltose, each at a concentration of about 0.1 g/L to about 20 g/L.

19. The liquid culture medium of claim 18, wherein the liquid culture medium further comprises L-glutamine.

20. The liquid culture medium of claim 19, wherein the liquid culture medium further comprises IGF1.

* * * * *